US012570613B2

(12) United States Patent
Lee et al.

(10) Patent No.: US 12,570,613 B2
(45) Date of Patent: Mar. 10, 2026

(54) IMIDAZOQUINOLINE OR BENZOINDAZOLONE COMPOUND AND INTERMEDIATE FOR PREPARING SAME

(71) Applicant: LMITO THERAPEUTICS INC., Yongin-si (KR)

(72) Inventors: Whee Seong Lee, Seongnam-Si (KR); Yong Rae Hong, Yongin-si (KR); In Seok Ko, Pyoungtaek-si (KR); Eun Ju Lee, Suwon-si (KR)

(73) Assignee: LMITO THERAPEUTICS INC., Yongin-si (KR)

( * ) Notice: Subject to any disclaimer, the term of this patent is extended or adjusted under 35 U.S.C. 154(b) by 469 days.

(21) Appl. No.: 18/041,944

(22) PCT Filed: Aug. 13, 2021

(86) PCT No.: PCT/KR2021/010842

§ 371 (c)(1),
(2) Date: Feb. 16, 2023

(87) PCT Pub. No.: WO2022/039460

PCT Pub. Date: Feb. 24, 2022

(65) Prior Publication Data

US 2024/0034719 A1 Feb. 1, 2024

(30) Foreign Application Priority Data

Aug. 17, 2020 (KR) ........................ 10-2020-0102921

(51) Int. Cl.
*C07D 231/56* (2006.01)

(52) U.S. Cl.
CPC .................................. *C07D 231/56* (2013.01)

(58) Field of Classification Search
CPC .................................................... C07D 231/56
See application file for complete search history.

(56) References Cited

U.S. PATENT DOCUMENTS 10,689,342 B2 * 6/2020 Provenzani .......... C07D 209/08
10,766,882 B2 * 9/2020 Lee .......................... A61P 3/10
2019/0241516 A1 8/2019 Provenzani et al.

FOREIGN PATENT DOCUMENTS

KR 10-2008-0099174 A 11/2008
KR 10-2015-0080423 A 7/2015
KR 10-2016-0116296 A 10/2016

OTHER PUBLICATIONS

Geeraerts et al., "Macrophage Metabolism as Therapeutic Target for Cancer, Atherosclerosis, and Obesity", Frontiers in Immunology, 2017, vol. 8, Article 289, 13 pages.
Ginhoux et al., "New insights into the multidimensional concept of macrophage ontogeny, activation and function", Nature Immunology, 2016, vol. 17, No. 1, pp. 34-40.
Isidro et al., "Colonic macrophage polarization in homeostasis, inflammation, and cancer", Am J Physiol Gastrointest Liver Physiol, 2016, vol. 311, pp. G59-G73.
Langston et al., "Metabolism Supports Macrophage Activation", Frontiers in Immunology, 2017, vol. 8, Article 61, 7 pages.
Li et al., "Novel naphtho[2,1-d]oxazole-4,5-diones as NQO1 substrates with improved aqueous solubility: Design, synthesis, and in vivo antitumor evaluation", Bioorganic & Medicinal Chemistry, 2016, vol. 24, pp. 1006-1013.

* cited by examiner

*Primary Examiner* — D Margaret M Seaman
(74) *Attorney, Agent, or Firm* — Vorys, Sater, Seymour and Pease LLP; Mih Suhn Koh

(57) ABSTRACT

Provided are an imidazoquinoline or benzoindazolone compound or a pharmaceutically acceptable salt, hydrate, solvate, enantiomer, diastereomer, tautomer or precursor drug thereof; a use thereof for preventing and treating an inflammatory disease; and an intermediate for preparing same, where the compound is used as a substrate of NQO1 to activate the oxidation-reduction of NQO1, thus making it possible to prevent the expression and activity of inflammatory cytokines, and as such, can be used for preventing or treating diseases associated with NQO1 activity.

12 Claims, No Drawings

IMIDAZOQUINOLINE OR BENZOINDAZOLONE COMPOUND AND INTERMEDIATE FOR PREPARING SAME

TECHNICAL FIELD

The present invention relates to an imidazoquinoline or benzoindazolone compound, a use for preventing or treating inflammatory diseases of the same, and an intermediate for preparing the same.

BACKGROUND ART

Our body's immune system has various defense systems which are able to respond to internal stimuli or exterior pathogens and to protect host against them. This immune system includes an immunity which increase an immune response and an immune tolerance which regulate an excessive immune response. These two immune reactions are tightly regulated and maintain a balance of immunity and immune tolerance, which is called an immune homeostasis and is very important in maintaining optimal health and function.

However, the immune reactions can be dysfunctional due to the various internal or external factors. When the immunity is stronger than the immune tolerance, that is, when there are excessively activated immune cells around, inflammatory disorders or auto-immune diseases may occur. On the other hand, when the immune tolerance is stronger than the immunity, a body would get infectious diseases or cancers. Therefore, an ideal immunotherapy would be to enhance the homeostasis of immune system between immunity and immune tolerance and thereby to cure immune-related disorders.

Ulcerative colitis is one of inflammatory disorders caused by genetic factors or excessive immune reactions resulting in an inflammation or intestinal ulcer in the colon. Inflammatory bowel diseases (IBD) are characterized with diarrhea containing mucus and blood, abdominal pain, weight loss, and blood in stool. In many cases, IBD showed recurrent episodes of remission and induction, and can lead to colon cancer or to other complications. Despite many research in the area of IBD being performed, there is no therapy developed yet to cure the disease completely. Generally, anti-inflammatory or adrenocortical hormone has been used, and depending on the disease condition of patients, immunosuppressive agents, steroids, or antibiotics has been used. There are several surgical treatments available for cure; however, the complications or aftereffects after the surgery lead to suggest therapeutic treatment.

The autoimmune diseases have over-activated immune system resulting in attacking the host healthy cells and disrupt homeostasis. They include rheumatoid arthritis, type 1 diabetes, inflammatory bowel disease, and atopic dermatitis.

Human body possesses various immune suppressive cells to maintain immune homeostasis through reducing the auto-immune-like and overly activated immune responses. Among them, macrophages play an important role in innate immunity and are present in many tissues in the body with various phenotypes.

Macrophages can protect our body from the attack of external pathogens through phagocytosis or secreting anti-microbial mediators. Also, macrophages perform many diverse reactions such as wound healing as well as inflammatory responses. Macrophages can be categorized into two traditional phenotypes, M1 and M2 based on their pathological conditions. Instead of describing macrophage polarization dichotomically with M1 and M2, it has been known to have diverse phenotypes based on their origins, sites, microenvironment, and disease status (Nature Immunology 2016(17), 34; Am J Physiol Gastrointest Liver Physiol 2016(311), G59). Pro-inflammatory macrophages with M1 phenotype are activated by LPS (lipopolysaccharides) or by TNF-α and then release pro-inflammatory cytokines such as IL-1β, IL-6 and TNF-α. The major metabolic pathway of M1-like macrophage metabolism is glycolysis in the cytosol. In contrast, the major metabolic pathway of M2-like macrophages is mitochondrial oxidative phosphorylation, and they are activated by IL-4 or IL-10, and play an important role in reducing inflammation and wound healing (Frontiers in immunology 2017, 61).

When NAD(P)H quinone oxidoreductase 1 (NQO1) enzymes are activated in the body, $NAD^+$ and $NAD^+/NADH$ ratio are increased, resulting in the activation of mitochondria, and therefore, the cell metabolism is converted from glycolysis to mitochondrial oxidative phosphorylation. This metabolic reprogramming induces macrophage polarization into anti-inflammatory M2 macrophages, resulting in decreased pro-inflammatory cytokine expressions and activity (Frontiers in immunology 2017, 289).

DETAILED DESCRIPTION OF THE INVENTION

Technical Problem to be Solved

An object of the prevent invention is to provide a novel imidazoquinoline or benzoindazolone compound, or a pharmaceutically acceptable salt, hydrate, solvate, enantiomer, diastereomer, tautomer or prodrug thereof, exhibiting effects of preventing or treating inflammatory disease; and an intermediate for preparing the same.

Technical Solution

The inventors have experimentally figured out that the novel imidazoquinoline or benzoindazolone compound of the invention is used as a substrate for NQO1 to facilitate a redox reaction of NQO1 so as to increase $NAD^+$ and $NAD^+/NADH$ ratio, thereby activating mitochondria to lead to the conversion of cell metabolism, and thus, it can be used for preventing or treating inflammatory diseases, by which the invention was completed.

Therefore, the first aspect of the invention relates to a compound represented by Chemical Formula 1 below, or a pharmaceutically acceptable salt, hydrate, solvate, enantiomer, diastereomer, tautomer or prodrug thereof:

Chemical Formula 1

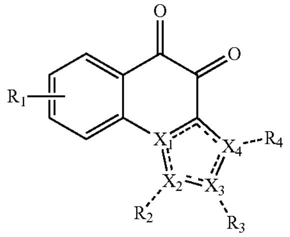

wherein, $R_1$ is selected from the group consisting of H, halo, substituted or unsubstituted $C_{1-6}$ alkyl, substituted or unsubstituted $C_{1-6}$ alkyloxy, substituted or unsubstituted $C_{2-5}$ heterocyclyl, substituted or unsubstituted $C_{6-10}$ aryl, substituted or unsubstituted heteroaryl, nitro, cyano, —C(O)$R_5$, —C(O)O$R_5$, —C(O)N$R_6R_7$ and —N$R_6R_7$;

$R_2$, $R_3$ and $R_4$ are each independently not present, or selected from the group consisting of H, halo, substituted or unsubstituted $C_{1-10}$alkyl, substituted or unsubstituted $C_{2-10}$ alkenyl, substituted or unsubstituted $C_{2-10}$ alkynyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$;

two of $X_1$, $X_2$, $X_3$ and $X_4$ are carbon (C) atoms and remaining two of $X_1$, $X_2$, $X_3$ and $X_4$ are nitrogen (N) atoms, provided that $X_1$ and $X_3$ cannot simultaneously be N and $X_2$ and $X_4$ cannot simultaneously be N;

is a single or double bond depending on $R_1$, $R_2$, $R_3$, $X_1$, $X_2$, $X_3$ and $X_4$; and ▪▪▪ is not present or a single bond depending on $X_1$, $X_2$, $X_3$ and $X_4$;

wherein the alkyl is a linear, branched or cyclic hydrocarbon which may have a double or triple bond in the hydrocarbon chain, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$ and —N$R_6R_7$, when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1 to 3 halos, $R_5$ is selected from the group consisting of H, $C_{1-6}$ alkyl, substituted or unsubstituted $C_{2-5}$ heterocyclyl, substituted or unsubstituted aryl, and substituted or unsubstituted heteroaryl, $R_6$ and $R_7$ are each independently selected from the group consisting of H, $C_{1-6}$ alkyl, heterocyclyl, substituted or unsubstituted aryl, and substituted or unsubstituted heteroaryl, or $R_6$ and $R_7$ may be joined together to form a heterocyclyl containing at least one nitrogen atom, with or without at least one further hetero atom selected from N, O and S, in ring structure, and the aryl is $C_{6-10}$ aromatic ring, the heterocyclyl is 3- to 7-membered cyclic group containing at least one hetero atom selected from N, O and S, and the heteroaryl is 5- to 10-membered hetero aromatic containing at least one hetero atom selected from N, O and S in ring structure.

The second aspect of the invention relates to a compound, which is an intermediate for preparing the compound of Chemical Formula 1 above, represented by Chemical Formula 2 below, or a salt, enantiomer, diastereomer or tautomer thereof:

Chemical Formula 2

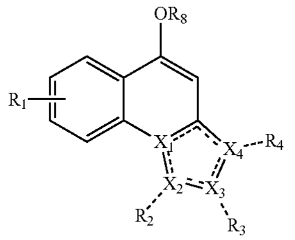

wherein, $R_1$, $R_2$, $R_3$, $R_4$, $X_2$, $X_3$, $X_4$,  and ▪▪▪ are the same as those defined for Chemical Formula 1, and $R_8$ is a typical protecting group for hydroxyl group which has been well known in the art.

Advantageous Effects

According to the prevent invention, a novel imidazoquinoline or benzoindazolone compound and an intermediate for preparing the same were provided.

Through the amount of cytochrome C being reduced, it was found that the compound of the invention was used as an efficient substrate for NQO1. A redox reaction of NQO1 facilitated by the compound of the invention can increase $NAD^+$ and $NAD^+$/NADH ratio, by which mitochondria is activated to lead the conversion of cell metabolism, making it possible to inhibit the expressions and activities of inflammatory cytokines. Thus, the compound of the invention is expected to be developed as a medicine for preventing or treating inflammatory diseases.

DETAILED DESCRIPTION OF THE EMBODIMENTS

Definition of Terms

The terms used in the present disclosure are briefly defined herein.

The term "pharmaceutically acceptable salt" means a salt form of a compound which does not cause any serious stimuli in an organism to which the compound is administered, and does not destroy biological activities and physical properties of the compound.

The terms "hydrate", "solvate", "prodrug", "tautomer", "enantiomer" and "diastereomer" also mean forms of a compound which does not cause any serious stimuli in an organism to which the compound is administered, and does not destroy biological activities and physical properties of the compound.

The pharmaceutically acceptable salt includes an acid-adduct salt which is formed by addition of an inorganic acid, such as hydrochloric acid, sulfuric acid, nitric acid, phosphoric acid, hydrobromic acid, hydriodic acid and the like, or an organic acid, such as tartaric acid, formic acid, citric acid, acetic acid, trichloroacetic acid, fluoroacetic acid, gluconic acid, benzoic acid, lactic acid, fumaric acid, maleic acid, salicylic acid, methanesulfonic acid, ethanesulfonic acid, benzenesulfonic acid, p-toluenesulfonic acid and the like.

In case that a carboxylic acid group is present in the compound of Chemical Formula 1, an example of its pharmaceutically acceptable salt includes an alkali metal or alkaline earth metal salt formed with lithium, sodium, potassium, calcium, magnesium or the like; an amino acid salt formed with lysine, arginine, guanidine or the like; and an organic salt formed with dicyclohexylamine, N-methyl-D-glucamine, tris(hydroxymethyl)methylamine, diethanolamine, choline, trimethylamine or the like. The compound of Chemical Formula 1 of the invention may be converted into its salt in accordance with a conventional method.

The term "hydrate" means a compound according to the present invention containing a stoichiometric or non-stoichiometric amount of water bound through non-covalent intermolecular forces, or a salt thereof.

The term "solvate" means a compound according to the present invention containing a stoichiometric or non-stoichiometric amount of solvent bound through non-covalent intermolecular forces, or a salt thereof. A solvent for the solvate may be any solvent which is volatile, non-toxic and/or suitable for administration to a human.

The term "prodrug" means a substance which can be converted in vivo into the compound of Chemical Formula 1 according to the present invention. In some cases, a prodrug is often used because it may be more easily administered than its parent drug. For example, biological activities can be achieved by oral administration of a prodrug, while it is not possible with its parent drug. In addition, a prodrug may have better solubility compared with its parent drug in a pharmaceutical formulation. For example, a prodrug may be in the form of an ester (a "prodrug"), which is easy to pass through cell membrane and can be hydrolyzed by a metabolism into a carboxylic acid as an active form within a cell where its water solubility is beneficial, although its water solubility is disadvantageous for transportation. Another example of the prodrug may be a short peptide (a poly-amino acid), in which a peptide is linked to an acid group, which is metabolized so that its active site is exposed.

The term "tautomer" means a type of structural isomers having an identical chemical or molecular formula, but different coupling between constituent atoms. For example, its structure is converted into each other between both isomers, such as a keto-enol structure.

The term "enantiomer" or "diastereomer" means an isomer which occurs due to different arrangements of atoms in a molecule even having an identical chemical formula or molecular formula. The term "enantiomer" means an isomer which is not superimposed with its mirror image, like a relation between a right hand and a left hand. In addition, the term "diastereomer" means a stereoisomer which is not in a mirror image relation. All isomers and mixtures thereof are also within the scope of the invention.

The term "alkyl" means a linear, branched and cyclic aliphatic hydrocarbon group, and it includes a "saturated alkyl" and a "unsaturated alkyl" which may contain at least one double or triple bond in the hydrocarbon chain.

The term "aryl" is $C_{6-10}$ aromatic ring, the term "heterocyclyl" means 3- to 7-membered cyclic group containing at least one hetero atom selected from nitrogen (N), oxygen (O) and sulfur (S) in ring structure, and the term "heteroaryl" means 5- to 10-membered hetero aromatic ring containing at least one hetero atom selected from nitrogen (N), oxygen (O) and sulfur (S) in ring structure.

Hereinafter, the present invention will be described in more detail.

The first aspect of the invention relates to a compound represented by Chemical Formula 1 below, or a pharmaceutically acceptable salt, hydrate, solvate, enantiomer, diastereomer, tautomer or prodrug thereof:

Chemical Formula 1

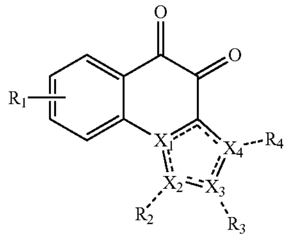

wherein, $R_1$ is selected from the group consisting of H, halo, substituted or unsubstituted $C_{1-6}$ alkyl, substituted or unsubstituted $C_{1-6}$ alkyloxy, substituted or unsubstituted $C_{2-5}$ heterocyclyl, substituted or unsubstituted $C_{6-10}$ aryl, substituted or unsubstituted heteroaryl, nitro, cyano, —C(O)$R_5$, —C(O)O$R_5$, —C(O)N$R_6R_7$ and —N$R_6R_7$;

$R_2$, $R_3$ and $R_4$ are each independently not present, or selected from the group consisting of H, halo, substituted or unsubstituted $C_{1-10}$alkyl, substituted or unsubstituted $C_{2-10}$ alkenyl, substituted or unsubstituted $C_{2-10}$ alkynyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$;

two of $X_1$, $X_2$, $X_3$ and $X_4$ are carton (C) atoms, and remaining two of $X_1$, $X_2$, $X_3$ and $X_4$ are nitrogen (N) atoms, provided that $X_1$ and $X_3$ cannot simultaneously be N and $X_2$ and $X_4$ cannot simultaneously be N;

---- is a single or double bond depending on $R_1$, $R_2$, $R_3$, $X_1$, $X_2$, $X_3$ and $X_4$; and ▪▪▪ is not present or a single bond depending on $X_1$, $X_2$, $X_3$ and $X_4$, wherein the alkyl a linear, branched or cyclic hydrocarbon group which may have a double or triple bond in the hydrocarbon chain, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$ and —N$R_6R_7$, when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1 to 3 halos, $R_5$ is selected from the group consisting of H, $C_{1-6}$ alkyl, substituted or unsubstituted $C_{2-5}$ heterocyclyl, substituted or unsubstituted aryl, and substituted or unsubstituted heteroaryl, $R_6$ and $R_7$ are each independently selected from the group consisting of H, $C_{1-6}$ alkyl, heterocyclyl, substituted or unsubstituted aryl, and substituted or unsubstituted heteroaryl, or $R_6$ and $R_7$ may be joined together to form a heterocyclyl containing at least one nitrogen atom, with or without at least one further hetero atom selected from N, O and S, in ring structure, and the aryl is $C_{6-10}$ aromatic ring, the heterocyclyl is a 3- to 7-membered cyclic group containing at least one hetero atom selected from N, O and S, and the heteroaryl is a 5- to 10-membered hetero aromatic ring containing at least one hetero atom selected from N, O and S in ring structure.

The compound of Chemical Formula 1 of the invention includes a compound wherein $X_2$ and $X_3$ are carton (C) atoms, and $X_1$ and $X_4$ are nitrogen (N) atoms. Herein, $R_1$ is the same as defined above, $R_2$ may be selected from the group consisting of H, unsubstituted $C_{1-10}$ alkyl, and substituted or unsubstituted $C_{6-10}$ aryl, $R_3$ may be selected from the group consisting of H, —C(O)O$R_5$ and —C(O) N$R_6R_7$, $R_4$ is not present, $R_5$ may be $C_{1-6}$ alkyl, and $R_6$ and $R_7$ may be independently H or $C_{1-6}$ alkyl.

The compound of Chemical Formula 1 of the invention includes a compound in which $X_1$ and $X_4$ are carbon (C) atoms, and $X_2$ and $X_3$ are nitrogen (N) atoms.

The first embodiments of the compound of Chemical Formula 1, in which $X_1$ and $X_4$ are carbon (C) atoms, and $X_2$ and $X_3$ are nitrogen (N) atoms, relate to a compound, wherein $R_2$ is not present, or selected from the group consisting of H, halo, substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, —C(O)$R_5$, —C(O)O$R_5$, —C(O) N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O) N$R_6R_7$, —N$R_6R_7$, and $C_{1-6}$ alkyl substituted with 1, 2 or 3 halos;

$R_3$ is not present, or selected from the group consisting of H, halo, substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O)O$R_5$, —C(O) N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O) O$R_5$, —C(O)N$R_6R_7$, —N$R_6R_7$, and $C_{1-6}$ alkyl substituted with 1, 2 or 3 halos;

$R_4$ is selected from the group consisting of H, halo, substituted or unsubstituted $C_{1-10}$ alkyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O)O$R_5$, —C(O)N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1, 2 or 3 halos;

$R_5$ is H or $C_{1-6}$ alkyl; and $R_6$ and $R_7$ are each independently H or $C_{1-6}$ alkyl, or $R_6$ and $R_7$ are joined together to form a heterocyclyl containing at least one nitrogen atom in ring structure.

In the compound of the first embodiments, $R_2$ may be not present, or selected from the group consisting of H, unsubstituted $C_{1-10}$ alkyl, substituted or unsubstituted $C_{2-5}$ heterocyclyl, substituted or unsubstituted $C_{6-10}$ aryl, and substituted or unsubstituted heteroaryl, wherein when the heterocyclyl, aryl or heteroaryl is substituted, its substituent may be independently selected from the group consisting of $C_{1-6}$ alkyl, halo and —C(O)O$R_5$, wherein, $R_5$ may be H or $C_{1-6}$ alkyl;

$R_3$ may be not present, or selected from the group consisting of $C_{1-10}$ alkyl, $C_{2-5}$ heterocyclyl, $C_{6-10}$ aryl and heteroaryl;

$R_4$ may be selected from the group consisting of H, substituted or unsubstituted $C_{1-10}$ alkyl, substituted or unsubstituted $C_{2-5}$ heterocyclyl, substituted or unsubstituted $C_{6-10}$ aryl, substituted or unsubstituted heteroaryl, wherein when the alkyl is substituted, its substituent may be selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, and —N$R_6R_7$, and when the heterocyclyl, aryl or heteroaryl is substituted, its substituent may be independently selected from the group consisting of $C_{1-6}$ alkyl, $C_{1-6}$ alkyloxy, halo, cyano, nitro, and $C_{1-6}$ alkyl substituted with 1, 2 or 3 halos.

The second embodiments of the compound of Chemical Formula 1, in which $X_1$ and $X_4$ are carbon (C) atoms, and $X_2$ and $X_3$ are nitrogen (N) atoms, relate to a compound, wherein $R_2$ is substituted alkyl, and its substituent is independently substituted or unsubstituted $C_{2-5}$ heterocyclyl, substituted or unsubstituted $C_{6-10}$ aryl, or substituted or unsubstituted heteroaryl, wherein when the heterocyclyl, aryl or heteroaryl is substituted, its substituent is independently selected from the group consisting of $C_{1-6}$ alkyl, $C_{1-6}$ alkyloxy and halo;

$R_3$ is not present, or selected from the group consisting of H, halo, substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O) O$R_5$, —C(O)N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O) $R_5$, —C(O)O$R_5$, —C(O)N$R_6R_7$, —N$R_6R_7$, and $C_{1-6}$ alkyl substituted with 1, 2 or 3 halos;

$R_4$ is selected from the group consisting of H, halo, substituted or unsubstituted $C_{1-10}$ alkyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O)O$R_5$, —C(O)N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1, 2 or 3 halos;

$R_5$ is H or $C_{1-6}$ alkyl; and $R_6$ and $R_7$ are each independently H or $C_{1-6}$ alkyl, or $R_6$ and $R_7$ are joined together to form a heterocyclyl containing at least one nitrogen atom in ring structure.

In the compound of the second embodiments, $R_2$ and $R_3$ may be substituted alkyl, and its substituent may be independently substituted or unsubstituted $C_{2-5}$ heterocyclyl, substituted or unsubstituted $C_{6-10}$ aryl, or substituted or unsubstituted heteroaryl, wherein when the heterocyclyl, aryl or heteroaryl is substituted, its substituent may be independently selected from the group consisting of $C_{1-6}$ alkyl, $C_{1-6}$ alkyloxy and halo; and $R_4$ may be H or $C_{1-10}$ alkyl.

The third embodiments of the compound of Chemical Formula 1, in which $X_1$ and $X_4$ are carbon (C) atoms, and $X_2$ and $X_3$ are nitrogen (N) atoms, relate to a compound, wherein $R_2$ is not present, or selected from the group consisting of H, halo, substituted or unsubstituted $C_{1-10}$alkyl, substituted or unsubstituted $C_{2-10}$alkenyl, substituted or unsubstituted $C_{2-10}$ alkynyl, substituted or unsubstituted $C_{2-3}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O)O$R_5$, —C(O)N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1, 2 or 3 halos;

$R_3$ is —S(O)(O)$R_5$ or —S(O)(O)N$R_6R_7$;

$R_4$ is selected from the group consisting of H, halo, substituted or unsubstituted $C_{1-10}$ alkyl, substituted or unsubstituted $C_{2-5}$ heterocyclyl, substituted or unsubstituted $C_{6-10}$ aryl, substituted or unsubstituted heteroaryl, —C(O)$R_5$, —C(O)O$R_5$, —C(O)N$R_6R_7$, —S(O)(O)$R_5$ and —S(O)(O)N$R_6R_7$, wherein when the alkyl is substituted, its substituent is selected from the group consisting of halo, $C_{1-6}$ alkyloxy, cyano, nitro, substituted or unsubstituted $C_{2-5}$ heterocyclyl, substituted or unsubstituted $C_{6-10}$ aryl, heteroaryl, —C(O)$R_5$, —C(O)O$R_5$, —C(O)N$R_6R_7$ and —N$R_6R_7$, and when the heterocyclyl, aryl or heteroaryl is substituted, its substituent is independently selected from the group consisting of $C_{1-6}$ alkyl, $C_{1-6}$ alkyloxy, halo, cyano, nitro, —C(O)$R_5$, —C(O)O$R_5$, —C(O)N$R_6R_7$, —N$R_6R_7$, and $C_{1-6}$ alkyl substituted with 1, 2 or 3 halos;

$R_5$ is selected from the group consisting of H, $C_{1-6}$ alkyl, substituted or unsubstituted $C_{2-5}$ heterocyclyl, substituted or unsubstituted aryl, and substituted or unsubstituted heteroaryl; and $R_6$ and $R_7$ are each independently selected from the group consisting of H, $C_{1-6}$ alkyl, heterocyclyl, substituted or unsubstituted aryl, and substituted or unsubstituted heteroaryl, or $R_6$ and $R_7$ may be joined together to form a heterocyclyl containing at least one nitrogen atom, with or without at least one further hetero atom selected from N, O and S, in ring structure, and when the heterocyclyl, aryl or heteroaryl is substituted, its substituent is independently selected from the group consisting of $C_{1-6}$ alkyl, $C_{1-6}$ alkyloxy, halo, nitro, cyano, —C(O)O$R_9$, and $C_{1-6}$ alkyl substituted with 1, 2 or 3 halos, wherein $R_9$ is H or $C_{1-6}$ alkyl.

In the compound of third embodiments, $R_2$ may not be present; $R_3$ may be —S(O)(O)$R_5$; $R_4$ may be selected from the group consisting of H, halo, substituted or unsubstituted $C_{1-10}$ alkyl, substituted or unsubstituted $C_{2-5}$ heterocyclyl, substituted or unsubstituted $C_{6-10}$ aryl, and substituted or unsubstituted heteroaryl; and $R_5$ may be selected from the group consisting of H, $C_{1-6}$ alkyl, substituted or unsubstituted $C_{2-5}$ heterocyclyl, substituted or unsubstituted aryl, and substituted or unsubstituted heteroaryl, wherein when the alkyl is substituted, its substituent may be selected from the group consisting of halo, $C_{1-6}$ alkyloxy, cyano, nitro, substituted or unsubstituted $C_{2-5}$ heterocyclyl, substituted or unsubstituted $C_{6-10}$ aryl, and heteroaryl, and when the heterocyclyl, aryl or heteroaryl is substituted, its substituent may be independently selected from the group consisting of $C_{1-6}$ alkyl, $C_{1-6}$ alkyloxy, halo, nitro, cyano, —C(O)O$R_9$, and $C_{1-6}$ alkyl substituted with 1, 2 or 3 halos, wherein $R_9$ may be H or $C_{1-6}$ alkyl.

In the present invention, the halo may be at least one selected from fluoro, chloro, bromo and iodo. The aryl is preferably phenyl or naphthyl, and the heteroaryl is 5- to 10-membered hetero aromatic cyclic group containing at least one hetero atom selected from N, O and S in ring structure, examples of which include pyridinyl, pyridazinyl, pyrrolyl, pyrazolyl, imidazolyl, oxazolyl, thiazolyl, furanyl and the like, but not limited thereto. The heterocyclyl is 3- to 7-membered hetero cyclic group containing at least one hetero atom selected from N, O and S in ring structure, examples of which include aziridinyl, azetidinyl, pyrrolidinyl, piperidinyl, piperazinyl, morpholinyl and the like, but not limited thereto.

The compound of Chemical Formula 1 of the invention may include Compounds 1 to 70 as follows:

Compound 1: 1-Phenylimidazo[1,2-a]quinolin-4,5-dione;

Compound 2: 1-(4-Fluorophenyl)imidazo[1,2-a]quinolin-4,5-dione;

Compound 3: 1-Isopropylimidazo[1,2-a]quinolin-4,5-dione;

Compound 4: 1-(4-(Trifluoromethyl)phenyl)imidazo[1,2-a]quinoline-4,5-dione;

Compound 5: Ethyl 4,5-dioxo-4,5-dihydroimidazo[1,2-a]quinolin-2-carboxylate;

Compound 6: Ethyl 4,5-dioxo-1-phenyl-4,5-dihydroimidazo[1,2-a]quinolin-2-carboxylate;

Compound 7: N,N-dimethyl-4,5-dioxo-1-phenyl-4,5-dihydroimidazo[1,2-a]quinolin-2-carboxamide;

Compound 8: N-methyl-4,5-dioxo-1-phenyl-4,5-dihydroimidazo[1,2-a]quinolin-2-carboxamide;

Compound 9: 3-Methyl-1-phenyl-1H-benzo[g]indazol-4,5-dione;

Compound 10: 3-Isopropyl-1-phenyl-1H-benzo[g]indazol-4,5-dione;

Compound 11: 3-Heptyl-1-phenyl-1H-benzo[g]indazol-4,5-dione;

Compound 12: 3-Phenethyl-1-phenyl-1H-benzo[g]indazol-4,5-dione;

Compound 13: 1,3-Diphenyl-1H-benzo[g]indazol-4,5-dione;

Compound 14: 3-(4-Fluorophenyl)-1-phenyl-1H-benzo[g]indazol-4,5-dione;

Compound 15: 3-(3,4-Difluorophenyl)-1-phenyl-1H-benzo[g]indazol-4,5-dione;

Compound 16: 3-(Bromomethyl)-1-phenyl-1H-benzo[g]indazol-4,5-dione;

Compound 17: 3-((Dimethylamino)methyl)-1-phenyl-1H-benzo[g]indazol-4,5-dione;

Compound 18: 3-(Methoxymethyl)-1-phenyl-1H-benzo[g]indazol-4,5-dione;

Compound 19: 3-(Isopropoxymethyl)-1-phenyl-1H-benzo[g]indazol-4,5-dione;

Compound 20: 1-Isopropyl-3-methyl-1H-benzo[g]indazol-4,5-dione;

Compound 21: 2-Isopropyl-3-methyl-2H-benzo[g]indazol-4,5-dione;

Compound 22: 1,3-Dimethyl-1H-benzo[g]indazol-4,5-dione;

Compound 23: 2,3-Dimethyl-2H-benzo[g]indazol-4,5-dione;

Compound 24: 3-((1H-Imidazol-1-yl)methyl)-1-phenyl-1H-benzo[g]indazol-4,5-dione;

Compound 25: 1-(4-Fluorophenyl)-3-methyl-1H-benzo[g]indazol-4,5-dione;

Compound 26: 1-(4-Chlorophenyl)-3-methyl-1H-benzo[g]indazol-4,5-dione;

Compound 27: 1-(3,5-Difluorophenyl)-3-methyl-1H-benzo[g]indazol-4,5-dione;

Compound 28: 1-(2,4-Dichlorophenyl)-3-methyl-1H-benzo[g]indazol-4,5-dione;

Compound 29: 3-Methyl-1-p-tolyl-1H-benzo[g]indazol-4,5-dione;

Compound 30: 3-Methyl-1-(pyridin-2-yl)-1H-benzo[g]indazol-4,5-dione;

Compound 31: 3-Methyl-1-(pyridin-3-yl)-1H-benzo[g]indazol-4,5-dione;

Compound 32: 1-(2,4-Difluorophenyl)-3-methyl-1H-benzo[g]indazol-4,5-dione;

Compound 33: 1-Phenyl-1H-benzo[g]indazol-4,5-dione;

Compound 34: 1-Phenyl-3-(trifluoromethyl)-1H-benzo[g]indazol-4,5-dione;

Compound 35: 7-Fluoro-3-methyl-1-phenyl-1H-benzo[g]indazol-4,5-dione;

Compound 36: 1-(3,5-Dichlorophenyl)-3-methyl-1H-benzo[g]indazol-4,5-dione;

Compound 37: 4-(3-Methyl-4,5-dioxo-4,5-dihydro-1H-benzo[g]indazol-1-yl)benzoic acid;

Compound 38: 3-Methyl-1-(naphthalen-1-yl)-1H-benzo[g]indazol-4,5-dione;

Compound 39: 1-(5-Chloropyridin-3-yl)-3-methyl-1H-benzo[g]indazol-4,5-dione;

Compound 40: 3-Methyl-1-(thiazol-2-yl)-1H-benzo[g]indazol-4,5-dione;

Compound 41: 3-Methyl-1-(pyridin-4-yl)-1H-benzo[g]indazol-4,5-dione;

Compound 42: 3-Methyl-2-(pyridin-4-yl)-2H-benzo[g]indazol-4,5-dione;

Compound 43: 3-Methyl-1H-benzo[g]indazol-4,5-dione;

Compound 44: 3-Methyl-2-(phenylsulfonyl)-2H-benzo[g]indazol-4,5-dione;

Compound 45: 3-Methyl-2-(4-Fluorophenylsulfonyl)-2H-benzo[g]indazol-4,5-dione;

Compound 46: 2-(2-Chlorophenylsulfonyl)-3-methyl-2H-benzo[g]indazol-4,5-dione;

Compound 47: 2-(3-Chlorophenylsulfonyl)-3-methyl-2H-benzo[g]indazol-4,5-dione;

Compound 48: 3-Methyl-2-(pyridin-3-ylsulfonyl)-2H-benzo[g]indazol-4,5-dione;

Compound 49: 2-(4-Chlorophenylsulfonyl)-3-methyl-2H-benzo[g]indazol-4,5-dione;

Compound 50: 3-Methyl-2-tosyl-2H-benzo[g]indazol-4,5-dione;

Compound 51: 2-(4-Methoxyphenylsulfonyl)-3-methyl-2H-benzo[g]indazol-4,5-dione;

Compound 52: Methyl 4-(3-methyl-4,5-dioxo-4,5-dihydro-2H-benzo[g]indazol-2-ylsulfonyl)benzoate;

Compound 53: 2-(Cyclopropylsulfonyl)-3-methyl-2H-benzo[g]indazol-4,5-dione;

Compound 54: 2-(Cyclopentylsulfonyl)-3-methyl-2H-benzo[g]indazol-4,5-dione;

Compound 55: 4-(3-Methyl-4,5-dioxo-4,5-dihydro-2H-benzo[g]indazol-2-ylsulfonyl)benzonitrile;

Compound 56: 3-Methyl-2-(4-nitrophenylsulfonyl)-2H-benzo[g]indazol-4,5-dione;

Compound 57: 3-Methyl-2-(4-(trifluoromethyl)phenylsulfonyl)-2H-benzo[g]indazol-4,5-dione;

Compound 58: 2-(3,4-Difluorophenylsulfonyl)-3-methyl-2H-benzo[g]indazol-4,5-dione;

Compound 59: 2-(2,4-Difluorophenylsulfonyl)-3-methyl-2H-benzo[g]indazol-4,5-dione;

Compound 60: 3-Methyl-2-(quinolin-8-ylsulfonyl)-2H-benzo[g]indazol-4,5-dione;

Compound 61: 3-Methyl-2-(1-methyl-1H-imidazol-2-ylsulfonyl)-2H-benzo[g]indazol-4,5-dione;

Compound 62: 3-Methyl-2-(morpholinosulfonyl)-2H-benzo[g]indazol-4,5-dione;

Compound 63: 1-Benzyl-3-methyl-1H-benzo[g]indazol-4,5-dione;

Compound 64: 3-Methyl-1-phenethyl-1H-benzo[g]indazol-4,5-dione;

Compound 65: 1-(4-Fluorophenethyl)-3-methyl-1H-benzo[g]indazol-4,5-dione;

Compound 66: 2-(4-Fluorophenethyl)-3-methyl-2H-benzo[g]indazol-4,5-dione;

Compound 67: 3-Methyl-1-(3-phenylpropyl)-1H-benzo[g]indazol-4,5-dione;

Compound 68: 3-Methyl-1-(4-methylphenethyl)-1H-benzo[g]indazol-4,5-dione;

Compound 69: 3-Methyl-2-(4-methylphenethyl)-2H-benzo[g]indazol-4,5-dione; and

Compound 70: 2-(2-Fluorophenethyl)-3-methyl-2H-benzo[g]indazol-4,5-dione.

The second aspect of the invention relates to a compound represented by Chemical Formula 2 below, or a salt, enantiomer, diastereomer or tautomer thereof, which is an intermediate for preparing the compound of Chemical Formula 1:

Chemical Formula 2

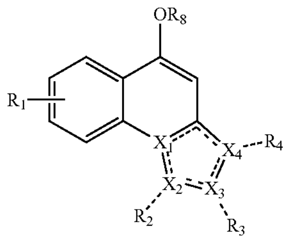

wherein, $R_1$, $R_2$, $R_3$, $R_4$, $X_2$, $X_3$, $X_4$, and are the same as those defined for Chemical Formula 1, and $R_8$ is a protecting group for hydroxyl group which has been well known in the art. Examples of the protecting group may include $C_{1-6}$ alkyl; $C_{1-6}$ alkyl substituted with $C_{6-10}$ aryl, for example, benzyl, trityl, methoxybenzyl, etc.; $C_{1-6}$ alkyl substituted with $C_{1-6}$ alkoxy, for example, methoxymethyl, methoxyethoxymethyl, etc.;

a carbonyl, for example, acetyl, pivaloyl, etc.; heterocyclyl, for example, tetrahydropyranyl, tetrahydrofuranyl, etc.; silyl substituted with $C_{1-6}$ alkyl, for example, trimethylsilyl, triisopropylsilyl, t-butylmethylsilyl, etc.; $C_{1-6}$ alkyl carbonyl, for example, acetyl, pivaloyl, etc.; but not limited thereto.

The compound of Chemical Formula 2 may be one selected from the group consisting of the following:

5-(Benzyloxy)-1-phenylimidazo[1,2-a]quinoline;
Ethyl 5-(benzyloxy)imidazo[1,2-a]quinoline-2-carboxylate;
5-(Benzyloxy)-1-(4-fluorophenyl)imidazo[1,2-a]quinoline;
5-(Benzyloxy)-1-isopropylimidazo[1,2-a]quinoline;
5-(Benzyloxy)-1-(4-(trifluoromethyl)phenyl)imidazo[1,2-a]quinoline;
5-Methoxy-3-methyl-1-phenyl-1H-benzo[g]indazole;
(5-Methoxy-1-phenyl-1H-benzo[g]indazol-3-yl)methanol;
3-(Bromomethyl)-5-(methoxymethoxy)-1-phenyl-1H-benzo[g]indazole;
5-Methoxy-3-methyl-1H-benzo[g]indazole;
1-(4-Fluorophenyl)-5-methoxy-3-methyl-1H-benzo[g]indazole;
1-(4-Chlorophenyl)-5-methoxy-3-methyl-1H-benzo[g]indazole;
1-(3,5-Difluorophenyl)-5-methoxy-3-methyl-1H-benzo[g]indazole;
1-(2,4-Dichlorophenyl)-5-methoxy-3-methyl-1H-benzo[g]indazole;
5-Methoxy-3-methyl-1-p-tolyl-1H-benzo[g]indazole;
5-Methoxy-3-methyl-1-(pyridin-2-yl)-1H-benzo[g]indazole;
5-Methoxy-3-methyl-1-(pyridin-3-yl)-1H-benzo[g]indazole;
1-(2,4-Difluorophenyl)-5-methoxy-3-methyl-1H-benzo[g]indazole;
5-Methoxy-1-phenyl-1H-benzo[g]indazole;
5-Methoxy-1-phenyl-3-(trifluoromethyl)-1H-benzo[g]indazole;
7-Fluoro-5-methoxy-3-methyl-1-phenyl-1H-benzo[g]indazole;
1-(3,5-Dichlorophenyl)-5-methoxy-3-methyl-1H-benzo[g]indazole;
Methyl 4-(5-methoxy-3-methyl-1H-benzo[g]indazol-1-yl)benzoate;
5-Methoxy-3-methyl-1-(naphthalen-1-yl)-1H-benzo[g]indazole; and
1-(5-Chloropyridin-3-yl)-5-methoxy-3-methyl-1H-benzo[g]indazole.

The third aspect of the invention relates to a pharmaceutical composition comprising as an effective ingredient the compound of Chemical Formula 1, or a pharmaceutically acceptable salt, hydrate, solvate, enantiomer, diastereomer, tautomer or prodrug thereof.

The pharmaceutical composition may further comprise at least one component selected from the group consisting of a carrier, an excipient and a diluent, which have been well known in the art.

The compound of Chemical Formula 1 of the invention is used as a substrate for NQO1, by which it can inhibit expressions and activities of inflammatory cytokines, and thus, it can be used for prevention or treatment of diseases associated with NQO1 activities.

EXAMPLES

Hereinafter, the present invention will be described in more detail with reference to examples. However, the examples are provided only for illustration of the invention, and should not be construed as limiting the scope of the invention.

Preparation Example 1: Synthesis of Intermediate 1 (4-(Benzyloxy)quinolin-2-amine)

2-Amino-4-hydroxyquinoline hydrate (5 mmol) and sodium hydride (10 mmol) were dissolved in dimethylformamide (20 mL) at 0° C. After stirred for 5 minutes, reaction solution was warmed up to room temperature, to which benzyl bromide (5.5 mmol) was added, and then stirred for 17 hrs. A mixture of ethyl acetate and n-hexane (1:1) was slowly added to the reaction solution with stirring. After filtered out the resulting solid, filtrate was washed with sat. aq. sodium hydrogen carbonate and dried to obtain the title compound without further purification.

Yield: 44%, White solid.

$^1H$ NMR (300 MHz, DMSO-$d_6$) δ: 7.85-7.82 (d, J=8.0 Hz, 1H), 7.53-7.51 (m, 2H), 7.46-7.33 (m, 5H), 7.11-7.06 (m, 1H), 6.30 (br s, 2H), 6.28 (s, 1H), 5.23 (s, 2H).

Preparation Example 2: Synthesis of Intermediate 2 (Ethyl 5-(benzyloxy)imidazo[1,2-a]quinolin-2-carboxylate)

(1) Synthesis of 1-(4-(benzyloxy)-2-iminoquinolin-1(2H)-yl)pentan-2,3-dione hydrobromide 4-(Benzyloxy)quinolin-2-amine (1 mmol, Intermediate 1) was dissolved in THF (10 mL) at room temperature. Ethyl 3-bromo-2-oxopropanoate (2 mmol) was added to the reaction solution and stirred for 12 hrs. When the reaction was completed, the resulting solid was washed with THF and filtered, to obtain the title compound without further purification.

(2) Synthesis of Intermediate 2 (Ethyl 5-(benzyloxy)imidazo[1,2-a]quinolin-2-carboxylate)

The previously prepared 1-(4-(benzyloxy)-2-iminoquinolin-1(2H)-pentan-2,3-dione hydrobromide (1 mmol) was dissolved in ethanol (10 mL) and reacted under reflux for 10 hrs. When the reaction was completed, reaction mixture was concentrated under reduced pressure, and obtained product was purified by column chromatography.

Yield: 57%, Yellowish solid.

$^1H$ NMR (300 MHz, DMSO-$d_6$) δ: 8.54 (s, 1H), 8.29-8.26 (m, 1H), 7.89 (d, J=8.3 Hz, 1H), 7.73-7.67 (m, 1H), 7.55-7.39 (m, 6H), 6.88 (s, 1H), 5.27 (s, 2H), 4.46 (q, J=7.2 Hz, 2H), 1.45 (t, J=7.2 Hz, 3H).

Preparation Example 3: Synthesis of Intermediate 3 (1-Bromo-4-methoxy-2-naphthoic acid)

(1) Synthesis of methyl 1-hydroxy-3-naphthoate

Benzaldehyde (282 mmol) and dimethyl succinate (310.2 mmol) were dissolved in methanol (100 mL). Then 25% Sodium methoxide solution (366.6 mmol) was slowly added and reaction mixture was stirred under reflux for 12 hours. When the reaction was completed, the reaction mixture was acidified with 3M HCl to pH 1 and extracted with dichloromethane. Organic layer was dried over $MgSO_4$ and concentrated under reduced pressure to give crude product. Crude product was dissolved in THF (80 mL), to which trifluoroacetic anhydride (282 mmol) was then slowly added with stirring at room temperature, and resulting mixture was stirred under reflux. When the reaction was completed, the reaction mixture was cooled to room temperature and neutralized with aq. $NaHCO_3$ at 0° C. The reaction mixture was extracted with ethyl acetate, and organic layer was dried over $MgSO_4$ and concentrated under reduced pressure. Obtained product was purified by column chromatography.

Yield: 30%, Yellowish solid.

$^1H$ NMR (300 MHz, $CDCl_3$) δ: 8.26-8.21 (m, 2H), 7.93-7.90 (m, 1H), 7.63-7.51 (m, 3H), 5.95 (s, 1H), 3.98 (s, 3H).

(2) Synthesis of methyl 4-methoxy-2-naphthoate

Methyl 1-hydroxy-3-naphthoate (4.54 mmol) and $K_2CO_3$ (9.08 mmol) were dissolved in DMF (15 mL), to which methyl iodide (9.54 mmol) was added, and then stirred for 2 hours at room temperature. When the reaction was completed, the reaction was quenched by adding water, the reaction mixture was extracted with dichloromethane, and organic layer was dried over $MgSO_4$ and concentrated under reduced pressure. Obtained product was used for the next step without further purification.

(3) Synthesis of methyl 1-bromo-4-methoxy-2-naphthoate

Methyl-1-methoxy-3-naphthoate (24.7 mmol) was dissolved in acetonitrile (60 mL). N-bromosuccinimide (26 mmol) was added to the reaction solution. Reaction mixture was stirred at reflux. When the reaction was completed, the reaction mixture was concentrated under reduced pressure and obtained solid was purified by column chromatography.

Yield: 90%, Yellowish solid.

$^1H$ NMR (300 MHz, $CDCl_3$) δ: 8.42 (d, J=8.3 Hz, 1H), 8.30 (d, J=7.7 Hz, 1H), 7.70-7.59 (m, 2H), 7.05 (s, 1H), 4.05 (s, 3H), 4.03 (s, 3H).

(4) Synthesis of Intermediate 3 (1-bromo-4-methoxy-2-naphthoic acid)

Methyl 1-bromo-4-methoxy-2-naphthoate (17.8 mmol) was dissolved in THF, methanol and water (1:1:1 v/v), to which KOH (53.4 mmol) was added, and then stirred under reflux for 3 hours. Reaction mixture was cooled to room temperature, acidified with 1M HCl and then extracted with ethyl acetate, and organic layer was dried over $MgSO_4$ and concentrated under reduced pressure. Obtained product was recrystallized from dichloromethane to yield the title compound.

Yield: 99%, White solid.

$^1H$ NMR (300 MHz, $CDCl_3$) δ: 8.48 (d, J=7.9 Hz, 1H), 8.31 (d, J=8.0 Hz, 1H), 7.72-7.60 (m, 2H), 7.25 (s, 1H), 4.06 (s, 3H).

Preparation Example 4: Intermediate 4 (1-(1-bromo-4-methoxynaphthalen-2-yl)ethan-1-one)

(1) Synthesis of 1-bromo-N,4-dimethoxy-N-methyl-2-naphthamide

1-Bromo-4-methoxy-2-naphthoic acid (10 mmol, intermediate 3) was suspended in methylene chloride (100 ml), to which N,O-dimethylhydroxylamine hydrochloride (11 mmol) was added. Triethylamine (40 mmol) was added, and the resulting mixture was stirred at room temperature for 5 minutes. Bis(2-oxo-3-oxazolidinyl)phosphinic chloride (11 mmol) was added, and the reaction solution was then stirred at room temperature for 12 hours. When the reaction was completed, 100 ml of 1M aq. HCl was added and then stirred for 10 minutes. The reaction mixture was extracted with methylene chloride. Extract was washed with sat. aq. $NaHCO_3$ and water, dried over $MgSO_4$, and concentrated under reduced pressure. Obtained product was used for the next step without further purification.

(2) Synthesis of Intermediate 4 (1-(1-bromo-4-methoxynaphthalen-2-yl)ethan-1-one)

1-Bromo-N,4-dimethoxy-N-methyl-2-naphthamide (10 mmol) was dissolved in THF (100 ml) and cooled to 0° C., to which methylmagnesium bromide (30 mmol) was slowly added, and then stirred for 10 minutes. The reaction solution was warmed up to room temperature and stirred for 5 hours. When the reaction was completed, the reaction mixture was cooled to 0° C., to which 1M aq. $NH_4Cl$ solution (100 ml) was slowly added, and then stirred for 10 minutes. Organic layer was separated, and aqueous layer was extracted with ethyl acetate. Combined organic layer was washed with brine, dried over $MgSO_4$ and concentrated under reduced pressure, and obtained product was purified by column chromatography.

Yield: 80%, White solid.

$^1H$ NMR (300 MHz, $CDCl_3$) δ: 8.33-8.27 (m, 2H), 7.70-7.59 (m, 2H), 6.73 (s, 1H), 4.02 (s, 3H), 2.74 (s, 3H).

Preparation Example 5: Synthesis of Intermediate 5 (5-methoxy-3-methyl-1-phenyl-1H-benzo[g]indazole)

(1) Synthesis of 1-(1-(1-bromo-4-methoxynaphthalen-2-yl)ethylidene)-2-phenylhydrazine 1-(1-Bromo-4-methoxynaphthalen-2-yl)ethan-1-one (7.2 mmol, Intermediate 4), phenylhydrazine (10.8 mmol) and p-toluenesulfonic acid monohydrate (1.4 mmol) were dissolved in ethanol (45 ml). The reaction solution was stirred at reflux for 3 hours. When the reaction was completed, the reaction mixture was cooled to 0° C. and stirred for 3 hours. The resulting solid was filtered, washed with cold ethanol, and dried under vacuum to obtain a white solid. The white solid was used for next step without further purification.

(2) Synthesis of Intermediate 5 (5-methoxy-3-methyl-1-phenyl-1H-benzo[g]indazole)

1-(1-(1-Bromo-4-methoxynaphthalen-2-yl)ethylidene)-2-phenylhydrazine (5 mmol) was dissolved in 1,4-dioxane (12.5 mL), to which CuI (5 mol %), trans-4-hydroxy-L-proline (5 mol %) and KOH (10 mmol) were added. The reaction mixture was then stirred at reflux for 10 hours. The reaction mixture was cooled to room temperature, to which water was added, and then extracted with ethyl acetate. Organic layer was dried over $MgSO_4$. The reaction mixture was concentrated under reduced pressure, and obtained product was purified by column chromatography.

Yield: 35%, Light brown solid.

$^1H$ NMR (300 MHz, DMSO-$d_6$) δ: 8.30 (m, 1H), 7.67-7.39 (m, 8H), 7.18 (s, 1H), 4.05 (s, 3H), 2.58 (s, 3H).

Preparation Example 6: Synthesis of Intermediate 6 ((5-methoxy-1-phenyl-1H-benzo[g]indazol-3-yl)methanol)

(1) Synthesis of 1-(1-bromo-4-methoxynaphthalen-2-yl)-2-hydroxyethan-1-one 1-(1-Bromo-4-methoxynaphthalen-2-yl)ethan-1-one (62.44 mmol, Intermediate 4), KOH (343.42 mmol) and $PhI(OAc)_2$ (78.05 mmol) were dissolved in methanol (400 ml). After stirring for 5 hours, methanol was removed under reduced pressure, water was added, and reaction mixture was extracted with ethyl acetate. Organic layer was dried over $MgSO_4$ and concentrated under reduced pressure. The residue was dissolved in methanol, to which 2N HCl was added, and resulting mixture was stirred for overnight. When the reaction was completed, methanol was removed under reduced pressure. The aqueous layer was extracted with ethyl acetate and organic layer was dried over $MgSO_4$. The reaction mixture was concentrated under reduced pressure and purified by column chromatography.

Yield: 60%, White solid.

$^1$H NMR (300 MHz, $CDCl_3$) δ: 8.35-8.29 (m, 2H), 7.72-7.60 (m, 2H), 6.79 (s, 1H), 4.89 (d, J=4.7 Hz, 2H), 4.03 (s, 3H), 3.36 (br s, 1H).

(2) Synthesis of 2-(1-bromo-4-methoxynaphthalen-2-yl)-2-(2-phenylhydrazono)ethan-1-ol Using 1-(1-bromo-4-methoxynaphthalen-2-yl)-2-hydroxyethan-1-one (37.46 mmol) as a starting material, the title compound was synthesized according to the procedure described in (1) of Preparation Example 5.

(3) Synthesis of Intermediate 6 (5-methoxy-1-phenyl-1H-benzo[g]indazol-3-yl)methanol Using 2-(1-bromo-4-methoxynaphthalen-2-yl)-2-(2-phenylhydrazono)ethan-1-ol (25.98 mmol) as a starting material, the title compound was synthesized according to the procedure described in (2) of Preparation Example 5.

Yield: 56%, Light brown solid $^1$H NMR (300 MHz, $CDCl_3$) δ: 8.27 (d, J=8.2 Hz, 1H), 7.44-7.39 (m, 7H), 7.22 (t, J=7.5 Hz, 1H), 6.96 (s, 1H), 5.00 (s, 2H), 3.96 (s, 3H).

Preparation Example 7: Synthesis of Intermediate 7 (3-(bromomethyl)-5-(methoxy)-1-phenyl-1H-benzo[g]indazole)

(1) Synthesis of 3-(bromomethyl)-5-methoxy-1-phenyl-1H-benzo[g]indazole

5-Methoxy-1-phenyl-1H-benzo[g]indazol-3-yl)methanol (14.5 mmol, Intermediate 6) was dissolved in methylene chloride (100 mL). While stirring at room temperature, $PBr_3$ was added, and reaction mixture was stirred for 5 hours. When the reaction was completed, water was added, and the reaction mixture was then extracted with methylene chloride. Extract was washed with brine and dried over $MgSO_4$. Obtained product was purified by column chromatography.

Yield: 67%, Brown solid.

$^1$H NMR (300 MHz, $CDCl_3$) δ: 8.40 (d, J=8.8 Hz, 1H), 7.64-7.56 (m, 5H), 7.55-7.51 (m, 2H), 7.35 (t, J=8.2 Hz, 1H), 7.05 (s, 1H), 4.95 (s, 2H), 4.12 (s, 3H).

(2) Synthesis of 3-(bromomethyl)-1-phenyl-1H-benzo[g]indazol-5-ol 3-(Bromomethyl)-5-methoxy-1-phenyl-1H-benzo[g]indazole (5 mmol) was dissolved in methylene chloride (30 mL). Reaction mixture was cooled to 0° C., to which $BBr_3$ (15 mmol) was slowly added, and then warmed to room temperature and stirred for 1 hour. After adding water, the reaction mixture was extracted with ethyl acetate. Crude product was recrystallized from methylene chloride and n-hexane, and the resulting brown solid was used for next step without further purification.

(3) Synthesis of Intermediate 7 (3-(bromomethyl)-5-(methoxymethoxy)-1-phenyl-1H-benzo[g]indazole)

3-(Bromomethyl)-1-phenyl-1H-benzo[g]indazol-5-ol (7.60 mmol) was dissolved in DMF (30 mL). After cooling to 0° C., chloromethyl methyl ether (19.0 mmol) and N,N-diisopropylethylamine (19.0 mmol) were added, and resulting mixture was slowly warmed to room temperature and stirred. When the reaction was completed, water was added, and the reaction mixture was then extracted with ethyl acetate. The extract was washed with brine, dried over $MgSO_4$ and concentrated under reduced pressure, and obtained product was purified by column chromatography.

Yield: 32%, White solid.

$^1$H NMR (300 MHz, $CDCl_3$) δ: 8.40 (d, J=7.6 Hz, 1H), 7.62-7.54 (m, 7H), 7.38-7.35 (m, 2H), 5.48 (s, 2H), 5.05 (s, 2H), 3.61 (s, 3H).

Preparation Example 8: Synthesis of Intermediate 8 (5-methoxy-3-methyl-1H-benzo[g]indazole)

(1) Synthesis of (1-(1-bromo-4-methoxynaphthalen-2-yl)ethylidene)hydrazine

Using 1-(1-Bromo-4-methoxynaphthalen-2-yl)ethan-1-one (11.0 mmol, Intermediate 4) and hydrazine monohydrate (12.1 mmol) as a starting material and a reactant, the title compound was synthesized according to the procedure described in (1) of Preparation Example 5 and used for next step without further purification.

(2) Synthesis of Intermediate 8 (5-methoxy-3-methyl-1H-benzo[g]indazole)

Using (1-(1-bromo-4-methoxynaphthalen-2-yl)ethylidene)hydrazine as a starting material, the title compound was synthesized according to the procedure described in (2) of Preparation Example 5.

Yield: 31%, Light brown solid.

$^1$H NMR (300 MHz, $CDCl_3$) δ: 13.2 (s, 1H), 8.34 (d, J=7.7 Hz, 1H), 8.20 (d, J=7.7 Hz, 1H), 7.66-7.53 (m, 2H), 7.03 (s, 1H), 3.97 (s, 3H), 2.57 (s, 3H).

Preparation Example 9: Synthesis of Intermediate 9 (1-(4-fluorophenyl)-5-methoxy-3-methyl-1H-benzo[g]indazole)

(1) Synthesis of 1-(1-(1-bromo-4-methoxynaphthalen-2-yl)ethylidene)-2-(4-fluorophenyl)hydrazine Using 1-(1-bromo-4-methoxynaphthalen-2-yl)ethan-1-one (7.2 mmol, Intermediate 4) and 4-fluorophenylhydrazine (10.8 mmol) as a starting material and a reactant, the title compound was synthesized according to the procedure described in (1) of Preparation Example 5, and obtained product was used for next step without further purification.

(2) Synthesis of Intermediate 9 (1-(4-fluorophenyl)-5-methoxy-3-methyl-1H-benzo[g]indazole)

Using 1-(1-(1-bromo-4-methoxynaphthalen-2-yl)ethylidene)-2-(4-fluorophenyl)hydrazine (5 mmol) as a starting material, the title compound was synthesized according to the procedure described in (2) of Preparation Example 5.

Yield: 32%, Light brown color.

$^1$H NMR (300 MHz, DMSO-$d_6$) δ: 8.41-8.38 (m, 1H), 7.57-7.52 (m, 4H), 7.36-7.33 (m, 1H), 7.28-7.25 (m, 2H), 6.92-6.90 (m, 1H), 4.10 (s, 3H), 2.66 (s, 3H).

Preparation Example 10: Synthesis of Intermediate 10 (1-(4-chlorophenyl)-5-methoxy-3-methyl-1H-benzo[g]indazole)

(1) Synthesis of 1-(1-(1-bromo-4-methoxynaphthalen-2-yl)ethylidene)-2-(4-chlorophenyl)hydrazine Using 1-(1-bromo-4-methoxynaphthalen-2-yl)ethan-1-one (7.2 mmol, Intermediate 4) and 4-chlorophenylhydrazine as a starting material and a reactant, the title compound was synthesized according to the procedure described in (1) of Preparation Example 5, and obtained product was used for next step without further purification.

(2) Synthesis of Intermediate 10 (1-(4-chlorophenyl)-5-methoxy-3-methyl-1H-benzo[g]indazole)

Using 1-(1-(1-bromo-4-methoxynaphthalen-2-yl)ethylidene)-2-(4-chlorophenyl)hydrazine (5 mmol) as a starting material, the title compound was synthesized according to the procedure described in (2) of Preparation Example 5.

Yield: 36%, Light brown solid.

$^1$H NMR (300 MHz, DMSO-$d_6$) δ: 8.37-8.31 (m, 1H), 7.61-7.58 (m, 1H), 7.55-7.50 (m, 5H), 7.37-7.30 (m, 1H), 6.89 (s, 1H), 4.08 (s, 3H), 2.64 (s, 3H).

Preparation Example 11: Synthesis of Intermediate 11 (1-(3,5-difluorophenyl)-5-methoxy-3-methyl-1H-benzo[g]indazole)

(1) Synthesis of 1-(1-(1-bromo-4-methoxynaphthalen-2-yl)ethylidene)-2-(3,5-difluorophenyl)hydrazine Using 1-(1-bromo-4-methoxynaphthalen-2-yl)ethan-1-one (7.2 mmol, Intermediate 4) and 3,5-difluorophenylhydrazine (10.8 mmol) as a starting material and a reactant, the title compound was synthesized according to the procedure described in (1) of Preparation Example 5, and obtained product was used for next step without further purification.

(2) Synthesis of Intermediate 11 (1-(3,5-difluorophenyl)-5-methoxy-3-methyl-1H-benzo[g]indazole)

Using 1-(1-(1-bromo-4-methoxynaphthalen-2-yl)ethylidene)-2-(3,5-difluorophenyl)hydrazine (5 mmol) as a starting material, the title compound was synthesized according to the procedure described in (2) of Preparation Example 5.

Yield: 41%, Light brown solid.

$^1$H NMR (300 MHz, DMSO-$d_6$) δ: 8.40-8.37 (m, 1H), 7.75-7.71 (m, 1H), 7.57-7.51 (m, 1H), 7.44-7.39 (m, 1H), 7.17-7.12 (m, 2H), 6.96-6.91 (m, 1H), 6.89 (s, 1H), 4.09 (s, 3H), 2.64 (s, 3H).

Preparation Example 12: Synthesis of Intermediate 12 (1-(2,4-dichlorophenyl)-5-methoxy-3-methyl-1H-benzo[g]indazole)

(1) Synthesis of 1-(1-(1-bromo-4-methoxynaphthalen-2-yl)ethylidene)-2-(2,4-dichlorophenyl)hydrazine Using 1-(1-bromo-4-methoxynaphthalen-2-yl)ethan-1-one (7.2 mmol, Intermediate 4) and 2,4-dichlorophenylhydrazine (10.8 mmol) as a starting material and a reactant, the title compound was synthesized according to the procedure described in (1) of Preparation Example 5, and obtained product was used for next step without further purification.

(2) Synthesis of Intermediate 12 (1-(2,4-dichlorophenyl)-5-methoxy-3-methyl-1H-benzo[g]indazole)

Using 1-(1-(1-bromo-4-methoxynaphthalen-2-yl)ethylidene)-2-(2,4-dichlorophenyl)hydrazine (5 mmol) as a starting material, the title compound was synthesized according to the procedure described in (2) of Preparation Example 5.

Yield: 53%, Light brown solid.

$^1$H NMR (300 MHz, DMSO-$d_6$) δ: 8.37-8.34 (m, 1H), 7.65 (s, 1H), 7.55-7.46 (m, 3H), 7.35-7.30 (m, 1H), 7.24-7.19 (m, 1H), 6.91 (s, 1H), 4.08 (s, 3H), 2.66 (s, 3H).

Preparation Example 13: Synthesis of Intermediate 13 (5-methoxy-3-methyl-1-p-tolyl-1H-benzo[g]indazole)

(1) Synthesis of 1-(1-(1-bromo-4-methoxynaphthalen-2-yl)ethylidene)-2-p-tolylhydrazine Using 1-(1-bromo-4-methoxynaphthalen-2-yl)ethan-1-one (7.2 mmol, Intermediate 4) and p-tolylhydrazine (10.8 mmol) as a starting material and a reactant, the title compound was synthesized according to the procedure described in (1) of Preparation Example 5, and obtained product was used for next step without further purification.

(2) Synthesis of Intermediate 13 (5-methoxy-3-methyl-1-p-tolyl-1H-benzo[g]indazole)

Using 1-(1-(1-bromo-4-methoxynaphthalen-2-yl)ethylidene)-2-p-tolylhydrazine (5 mmol) as a starting material, the title compound was synthesized according to the procedure described in (2) of Preparation Example 5.

Yield: 26%, Light brown color.

$^1$H NMR (300 MHz, DMSO-$d_6$) δ: 8.36-8.30 (m, 1H), 7.61-7.56 (m, 1H), 7.53-7.43 (m, 3H), 7.36-7.33 (m, 3H), 6.90 (s, 1H), 4.08 (s, 3H), 2.64 (s, 3H), 2.49 (s, 3H).

Preparation Example 14: Synthesis of Intermediate 14 (5-methoxy-3-methyl-1-(pyridin-2-yl)-1H-benzo[g]indazole)

(1) Synthesis of 2-(2-(1-(1-bromo-4-methoxynaphthalen-2-yl)ethylidene)hydrazinyl)pyridine Using 1-(1-bromo-4-methoxynaphthalen-2-yl)ethan-1-one (7.2 mmol, Intermediate 4) and 2-hydrazinopyridine (10.8 mmol) as a starting material and a reactant, the title compound was synthesized according to the procedure described in (1) of Preparation Example 5, and obtained product was used for next step without further purification.

(2) Synthesis of Intermediate 14 (5-methoxy-3-methyl-1-(pyridin-2-yl)-1H-benzo[g]indazole)

2-(2-(1-(1-bromo-4-methoxynaphthalen-2-yl)ethylidene)hydrazinyl)pyridine (5 mmol) as a starting material, the title compound was synthesized according to the procedure described in (2) of Preparation Example 5.

Yield: 30%, Light brown solid.

$^1$H NMR (300 MHz, DMSO-$d_6$) δ: 8.65-8.62 (m, 1H), 8.39-8.36 (m, 1H), 8.05-7.89 (m, 2H), 7.83-7.71 (m, 1H), 7.61-7.49 (m, 1H), 7.47-7.33 (m, 2H), 6.90-6.87 (m, 1H), 4.08 (s, 3H), 2.65 (s, 3H).

Preparation Example 15: Synthesis of Intermediate 15 (5-methoxy-3-methyl-1-(pyridin-3-yl)-1H-benzo[g]indazole)

(1) Synthesis of 3-(2-(1-(1-bromo-4-methoxynaphthalen-2-yl)ethylidene)hydrazinyl)pyridine Using 1-(1-bromo-4-methoxynaphthalen-2-yl)ethan-1-one (7.2 mmol, Intermediate 4) and 3-hydrazinopyridine (10.8 mmol) as a starting material and a reactant, the title compound was synthesized according to the procedure described in (1) of Preparation Example 5, and obtained product was used for next step without further purification.

(2) Synthesis of Intermediate 15 (5-methoxy-3-methyl-1-(pyridin-3-yl)-1H-benzo[g]indazole)

Using 3-(2-(1-(1-bromo-4-methoxynaphthalen-2-yl)ethylidene)hydrazinyl)pyridine (5 mmol) as a starting material, the title compound was synthesized according to the procedure described in (2) of Preparation Example 5.

Yield: 22%, Light brown solid.

$^1$H NMR (300 MHz, DMSO-$d_6$) δ: 8.93-8.85 (m, 1H), 8.80-8.71 (m, 1H), 8.44-8.36 (m, 1H), 7.97-7.89 (m, 1H), 7.61-7.48 (m, 3H), 7.41-7.32 (m, 1H), 6.92-6.87 (m, 1H), 4.09 (s, 3H), 2.67 (s, 3H).

Preparation Example 16: Synthesis of Intermediate 16 (1-(2,4-difluorophenyl)-5-methoxy-3-methyl-1H-benzo[g]indazole)

(1) Synthesis of 1-(1-(1-bromo-4-methoxynaphthalen-2-yl)ethylidene-2-(2,4-difluorophenyl)hydrazine Using 1-(1-bromo-4-methoxynaphthalen-2-yl)ethan-1-one (7.2 mmol, Intermediate 4) and 2,4-difluorophenylhydrazine (10.8 mmol) as a starting material and a reactant, the title compound was synthesized according to the procedure described in (1) of Preparation Example 5, and obtained product was used for next step without further purification.

(2) Synthesis of Intermediate 16 (1-(2,4-difluorophenyl)-5-methoxy-3-methyl-1H-benzo[g]indazole)

Using 1-(1-(1-bromo-4-methoxynaphthalen-2-yl)ethylidene)-2-(2,4-difluorophenyl)hydrazine (5 mmol) as a starting material, the title compound was synthesized according to the procedure described in (2) of Preparation Example 5.

Yield: 37%, Light brown solid.

$^1$H NMR (300 MHz, DMSO-$d_6$) δ: 8.42-8.39 (m, 1H), 7.69 (s, 1H), 7.56-7.47 (m, 3H), 7.39-7.33 (m, 1H), 7.30-7.26 (m, 1H), 6.96 (s, 1H), 4.09 (s, 3H), 2.68 (s, 3H).

Preparation Example 17: Synthesis of Intermediate 17 (5-methoxy-1-phenyl-1H-benzo[g]indazole)

(1) Synthesis of 1-bromo-4-methoxy-2-naphthaldehyde 1-bromo-N,4-dimethoxy-N-methyl-2-naphthamide (35.6 mmol, the product of step (1) in Preparation Example 4) was dissolved in THF (200 ml), and reaction mixture was cooled to 0° C. Diisobutylaluminum hydride solution (71.3 mmol) was slowly added and reaction mixture was stirred for 10 minutes. The reaction mixture was warmed to room temperature and stirred for 10 hours. When the reaction was completed, the reaction mixture was cooled to 0° C., to which 1M aq. $NH_4Cl$ (100 ml) was added, and then stirred for 10 minutes. Organic layer was separated. Aqueous layer was extracted with ethyl acetate, and combined organic layer was washed with brine and dried over $MgSO_4$. The reaction mixture was concentrated under reduced pressure and obtained product was purified by column chromatography.

Yield: 42%, White solid.

$^1$H NMR (300 MHz, $CDCl_3$) δ: 10.66 (s, 1H), 8.50-8.47 (m, 1H), 8.33-8.31 (m, 1H), 7.71-7.68 (m, 2H), 7.30 (s, 1H), 4.07 (s, 3H).

(2) Synthesis of 1-((1-bromo-4-methoxynaphthalen-2-yl)methylene)-2-phenylhydrazine Using 1-bromo-4-methoxy-2-naphthaldehyde (7.5 mmol) as a starting material, the title compound was synthesized according to the procedure described in (1) of Preparation Example 5, and obtained product was used for next step without further purification.

(3) Synthesis of Intermediate 17 (5-methoxy-1-phenyl-1H-benzo[g]indazole)

Using 1-((1-bromo-4-methoxynaphthalen-2-yl)methylene)-2-phenylhydrazine (5 mmol) as a starting material, the title compound was synthesized according to the procedure described in (2) of Preparation Example 5.

Yield: 27%, Brown solid.

$^1$H NMR (300 MHz, $CDCl_3$) δ: 8.34-8.36 (m, 1H), 8.14 (s, 1H), 7.58-7.49 (m, 7H), 7.35-7.30 (m, 1H), 7.00 (s, 1H), 4.06 (s, 3H).

Preparation Example 18: Synthesis of Intermediate 18 (5-methoxy-1-phenyl-3-(trifluoromethyl)-1H-benzo[g]indazole)

(1) Synthesis of 1-(1-bromo-4-methoxynaphthalen-2-yl)-2,2,2-trifluoroethanol

1-Bromo-4-methoxy-2-naphthaldehyde (6.04 mmol) was dissolved in THF (7.5 mL). Reaction mixture was cooled to 0° C., to which TMS-$CF_3$ (15.08 mmol) and TBAF solution (1M in THF, 0.6 mmol) were added, and then stirred for 8 hours. After adding water (1 mL), reaction mixture was stirred for 10 hours, to which water was added additionally, and then extracted with ethyl acetate. Organic layer was washed with $MgSO_4$ and concentrated under reduced pressure. Obtained product was purified by column chromatography.

Yield: 90%, opaquely yellowish oil.

$^1$H NMR (300 MHz, $CDCl_3$) δ: 8.32-8.27 (m, 2H), 7.64-7.55 (m, 2H), 7.10 (s, 1H), 6.00-5.98 (m, 1H), 4.04 (s, 3H).

(2) Synthesis of 1-(1-bromo-4-methoxynaphthalen-2-yl)-2,2,2-trifluoroethanone 1-(1-Bromo-4-methoxynaphthalen-2-yl)-2,2,2-trifluoroethanol (6 mmol) and IBX (18 mmol) were suspended in ethyl acetate (100 mL). Resulting mixture was warmed up and stirred at reflux for 3 hours. When the reaction was completed, the reaction mixture was filtered and filtrate was concentrated under reduced pressure. Obtained product was purified by column chromatography.

Yield: 89%, Yellow solid.

$^1$H NMR (300 MHz, $CDCl_3$) δ: 8.37-8.31 (m, 2H), 7.74-7.63 (m, 2H), 6.80 (s, 1H), 4.04 (s, 3H).

(3) Synthesis of 1-(1-(1-bromo-4-methoxynaphthalen-2-yl)-2,2,2-trifluoroethylidene)-2-phenylhydrazine Using 1-(1-bromo-4-methoxynaphthalen-2-yl)-2,2,2-trifluoroethanone (5.88 mmol) as a starting material, the title compound was synthesized according to the procedure described in (1) of Preparation Example 5 and used for next step without further purification.

(4) Synthesis of Intermediate 18 (5-methoxy-1-phenyl-3-(trifluoromethyl)-1H-benzo[g]indazole)

Using 1-(1-(1-bromo-4-methoxynaphthalen-2-yl)-2,2,2-trifluoroethylidene)-2-phenylhydrazine (4.13 mmol) as a starting material, the title compound was synthesized according to the procedure described in (2) of Preparation Example 5.

Yield: 44%, Light yellow solid.

$^1$H NMR (300 MHz, $CDCl_3$) δ: 8.47-8.39 (m, 1H), 8.31-8.28 (m, 1H), 7.72-7.48 (m, 5H), 7.39-7.34 (m, 1H), 7.21-7.03 (m, 1H), 4.02 (s, 3H).

Preparation Example 19: Synthesis of Intermediate 19 (7-fluoro-5-methoxy-3-methyl-1-phenyl-1H-benzo[g]indazole (1) Synthesis of methyl 6-fluoro-4-hydroxy-2-naphthoate Using 4-fluorobenzaldehyde (16.3 mmol) as a starting material, the title compound was synthesized according to the procedure described in (1) of Preparation Example 3.

Yield: overall 26%, White solid.

$^1$H NMR (300 MHz, $CDCl_3$) δ: 8.18 (s, 1H), 7.91-7.79 (m, 1H), 7.42 (s, 1H), 7.33-7.27 (m, 1H), 5.68 (br s, 1H), 3.94 (s, 3H).

(2) Synthesis of methyl 6-fluoro-4-methoxy-2-naphthoate

Using methyl 6-fluoro-1-hydroxy-3-naphthoate as a starting material, the title compound was synthesized according to the procedure described in (2) of Preparation Example 3, and obtained light brown product was used for next step without purification.

(3) Synthesis of methyl 1-bromo-6-fluoro-4-methoxy-2-naphthoate

Using methyl 6-fluoro-4-methoxy-2-naphthoate as a starting material, the title compound was synthesized according to the procedure described in (3) of Preparation Example 3.

Yield: 92%, Light orange solid.

$^1$H NMR (300 MHz, $CDCl_3$) δ: 8.46-8.41 (m, 1H), 7.92-7.87 (m, 1H), 7.44-7.39 (m, 1H), 7.06 (s, 1H), 4.03 (s, 3H), 4.01 (s, 3H).

(4) Synthesis of 1-bromo-6-fluoro-4-methoxy-2-naphthoic acid

Using methyl 1-bromo-6-fluoro-4-methoxy-2-naphthoate as a starting material, the title compound was synthesized according to the procedure described in (4) of Preparation Example 3.

Yield: 96%, White solid.

$^1$H NMR (300 MHz, $CDCl_3$) δ: 8.54-8.49 (m, 1H), 7.94-7.91 (m, 1H), 7.47-7.41 (m, 1H), 7.25 (s, 1H), 4.06 (s, 3H).

(5) Synthesis of 1-Bromo-6-fluoro-N,4-dimethoxy-N-methyl-2-naphthamide

Using 1-bromo-6-fluoro-4-methoxy-2-naphthoic acid (3.34 mmol) as a starting material, the title compound was synthesized according to the procedure described in (1) of Preparation Example 4, and obtained product was used for next step without further purification.

Yield: 90%, Yellow oil.

(6) Synthesis of 1-(1-Bromo-6-fluoro-4-methoxynaphthalen-2-yl)ethanone

Using 1-Bromo-6-fluoro-N,4-dimethoxy-N-methyl-2-naphthamide (13.3 mmol) as a starting material, the title compound was synthesized according to the procedure described in (2) of Preparation Example 2.

Yield: 46%, White solid.

$^1$H NMR (300 MHz, $CDCl_3$) δ: 8.35-8.30 (m, 1H), 7.90-7.87 (m, 1H), 7.44-7.39 (m, 1H), 6.75 (s, 1H), 4.01 (s, 3H), 2.73 (s, 3H).

(7) Synthesis of 1-(1-(1-bromo-6-fluoro-4-methoxynaphthalen-2-yl)ethylidene)-2-phenylhydrazine Using 1-(1-bromo-6-fluoro-4-methoxynaphthalen-2-yl)ethanone (6.15 mmol) as a starting material, the title compound was synthesized according to the procedure described in (1) of Preparation Example 5, and obtained product was used for next step without further purification.

(8) Synthesis of Intermediate 19 (7-fluoro-5-methoxy-3-methyl-1-phenyl-1H-benzo[g]indazole)

Using 1-(1-(1-bromo-6-fluoro-4-methoxynaphthalen-2-yl)ethylidene)-2-phenylhydrazine (1.81 mmol) as a starting material, the title compound was synthesized according to the procedure described in (2) of Preparation Example 5.

Yield: 25%, Brown solid.

$^1$H NMR (300 MHz, $CDCl_3$) δ: 8.08-7.90 (m, 1H), 7.62-7.48 (m, 6H), 7.17-7.03 (m, 1H), 6.85 (s, 1H), 4.07 (s, 3H), 2.64 (s, 3H).

Preparation Example 20: Synthesis of Intermediate 20 (1-(3,5-dichlorophenyl)-5-methoxy-3-methyl-1H-benzo[g]indazole)

(1) Synthesis of 1-(1-(1-bromo-4-methoxynaphthalen-2-yl)ethylidene)-2-(3,5-dichlorophenyl)hydrazine Using 1-(1-bromo-4-methoxynaphthalen-2-yl)ethan-1-one (3.6 mmol, Intermediate 4) and 3,5-dichlorophenylhydrazine hydrochloride (3.96 mmol) as a starting material and a reactant, the title compound was synthesized according to the procedure described in (1) of Preparation Example 5, and obtained product was used for next step without further purification.

(2) Synthesis of Intermediate 20 (1-(3,5-dichlorophenyl)-5-methoxy-3-methyl-1H-benzo[g]indazole)

Using 1-(1-(1-bromo-4-methoxynaphthalen-2-yl)ethylidene)-2-(3,5-dichlorophenyl)hydrazine (3.2 mmol) as a starting material, the title compound was synthesized according to the procedure described in (2) of Preparation Example 5.

Yield: 24%, Brown solid.

$^1$H NMR (300 MHz, DMSO-$d_6$) δ: 8.34 (d, 1H), 7.63 (d, 1H), 7.50 (t, 1H), 7.45 (d, 2H), 7.41 (t, 1H), 7.37 (t, 1H), 6.81 (s, 1H), 3.97 (s, 3H), 2.56 (s, 3H).

Preparation Example 21: Synthesis of Intermediate 21 (methyl 4-(5-methoxy-3-methyl-1H-benzo[g]indazol-1-yl)benzoate)

(1) Synthesis of methyl 4-(2-(1-(1-bromo-4-methoxynaphthalen-2-yl)ethylidene)hydrazinyl)benzoate Using 1-(1-bromo-4-methoxynaphthalen-2-yl)ethan-1-one (7.2 mmol, Intermediate 4) and methyl 4-hydrazinylbenzoate hydrochloride (7.92 mmol) as a starting material and a reactant, the title compound was synthesized according to the procedure described in (1) of Preparation Example 5, and obtained product was used for next step without further purification.

(2) Synthesis of Intermediate 21 (Methyl 4-(5-methoxy-3-methyl-1H-benzo[g]indazol-1-yl)benzoate)

Using methyl 4-(2-(1-(1-bromo-4-methoxynaphthalen-2-yl)ethylidene)hydrazinyl)benzoate (3.99 mmol) as a starting material, the title compound was synthesized according to the procedure described in (2) of Preparation Example 5, and obtained product was used for next step without further purification.

Yield: 22%, Light brown solid.

Preparation Example 22: Synthesis of Intermediate 22 (5-methoxy-3-methyl-1-(naphthalen-1-yl)-1H-benzo[g]indazole)

(1) Synthesis of 1-(1-(1-bromo-4-methoxynaphthalen-2-yl)ethylidene)-2-(naphthalen-1-yl)hydrazine Using 1-(1-bromo-4-methoxynaphthalen-2-yl)ethan-1-one (2.1 mmol, Intermediate 4) and 1-naphthylhydrazine hydrochloride (2.31 mmol) as a starting material and a reactant, the title compound was synthesized according to the procedure described in (1) of Preparation Example 5, and obtained product was used for next step without further purification.

(2) Synthesis of Intermediate 22 (5-methoxy-3-methyl-1-(naphthalen-1-yl)-1H-benzo[g]indazole)

Using 1-(1-(1-bromo-4-methoxynaphthalen-2-yl)ethylidene)-2-(naphthalen-1-yl)hydrazine (1.82 mmol) as a starting material, the title compound was synthesized according to the procedure described in (2) of Preparation Example 5, and obtained product was used for next step without further purification.

Yield: 51%, Light brown solid.

Preparation Example 23: Synthesis of Intermediate 23 (1-(5-chloropyridin-3-yl)-5-methoxy-3-methyl-1H-benzo[g]indazole)

(1) Synthesis of 3-(2-(1-(1-bromo-4-methoxynaphthalen-2-yl)ethylidene)hydrazinyl)-5-chloropyridine Using 1-(1-bromo-4-methoxynaphthalen-2-yl)ethan-1-one (10.75 mmol, Intermediate 4) and 5-chloro-3-hydrazinopyridine hydrochloride (11.83 mmol) as a starting material and a reactant, the title compound was synthesized according to the procedure described in (1) of Preparation Example 5, and obtained product was used for next step without further purification.

(2) Synthesis of Intermediate 23 (1-(5-chloropyridin-3-yl)-5-methoxy-3-methyl-1H-benzo[g]indazole)

Using 3-(2-(1-(1-bromo-4-methoxynaphthalen-2-yl)ethylidene)hydrazinyl)-5-chloropyridine (8.12 mmol) as a starting material, the title compound was synthesized according to the procedure described in (2) of Preparation Example 5.

Yield: 40%, brown solid.

$^1$H NMR (300 MHz, DMSO-$d_6$) δ: 8.60-8.58 (m, 1H), 8.39-8.36 (m, 1H), 8.05-7.90 (m, 1H), 7.80-7.71 (m, 1H), 7.60-7.53 (m, 1H), 7.40-7.31 (m, 2H), 6.88 (s, 1H), 4.08 (s, 3H), 2.65 (s, 3H).

Example 1: Synthesis of Compound 1 (1-phenylimidazo[1,2-a]quinolin-4,5-dione)

(1) Synthesis of 5-(benzyloxy)-1-phenylimidazo[1,2-a]quinoline 4-(Benzyloxy)quinolin-2-amine (2 mmol) and Sulfur (Sa, 4 mmol) were dissolved in cyclohexane (2 mL) and DMSO (4 mL). 2-Phenylacetaldehyde (4 mmol) was added, and resulting mixture was stirred at 120° C. for 30 minutes. When the reaction was completed, $H_2O$ was added, and the reaction mixture was extracted with ethyl acetate. Combined organic layer was dried over $MgSO_4$ and concentrated under reduced pressure, and obtained product was purified by column chromatography.

Yield: 31%, Yellow solid.

$^1$H NMR (300 MHz, DMSO-$d_6$) δ: 8.27-8.24 (m, 1H), 7.55-7.27 (m, 12H), 6.95 (s, 1H), 5.28 (s, 2H).

(2) Synthesis of 1-phenylimidazo[1,2-a]quinolin-5-ol 5-(Benzyloxy)-1-phenylimidazo[1,2-a]quinoline (0.8 mmol) was dissolved in methylene chloride (2 mL). The resulting mixture was cooled to 0° C., to which $BBr_3$ (1.68 mmol) was slowly added dropwise, and then slowly warmed to room temperature. The reaction mixture was stirred for 1 hour. After adding water, the reaction mixture was extracted with ethyl acetate. Crude product was purified by recrystallization from methylene chloride and n-hexane.

Yield: 66%, Brown solid.

$^1H$ NMR (300 MHz, DMSO-$d_6$) δ: 8.14-8.12 (d, J=7.0 Hz, 1H), 7.51-7.34 (m, 8H), 7.26 (s, 1H), 6.75 (br s, 1H).

(3) Synthesis of Compound 1 (1-phenylimidazo[1,2-a]quinolin-4,5-dione)

1-Phenylimidazo[1,2-a]quinolin-5-ol (0.38 mmol) was dissolved in DMF (10 mL). IBX (0.38 mmol) was added in one-portion, and the resulting mixture was stirred for 2 hours. When the reaction was completed, the reaction was quenched by adding sat. $NaHCO_3$. The reaction mixture was extracted with ethyl acetate, and combined organic layer was dried over $MgSO_4$ and concentrated under reduced pressure, and obtained product was purified by column chromatography.

Yield: 65%, Yellow solid.

$^1H$ NMR (300 MHz, DMSO-$d_6$) δ: 8.20-8.17 (m, 1H), 7.60-7.50 (m, 5H), 7.46 (s, 1H), 7.44-7.33 (m, 2H), 7.11-7.08 (m, 1H).

Example 2: Synthesis of Compound 2 (1-(4-fluorophenyl)imidazo[1,2-a]quinolin-4,5-dione)

(1) Synthesis of 5-(benzyloxy)-1-(4-fluorophenyl)imidazo[1,2-a]quinoline 4-(Benzyloxy)quinolin-2-amine (0.3 mmol, Intermediate 1) and sulfur (Sa, 0.6 mmol) were dissolved in cyclohexane (0.3 mL) and DMSO (0.6 mL). 2-(4-fluorophenyl)acetaldehyde (0.6 mmol) was added, and resulting mixture was stirred at 120° C. for 30 minutes. When the reaction was completed, $H_2O$ was added, and the reaction mixture was extracted with ethyl acetate. Combined organic layer was dried over $MgSO_4$ and concentrated under reduced pressure.

Obtained product was purified by column chromatography.

Yield: 35%, Light yellow solid.

$^1H$ NMR (300 MHz, $CDCl_3$) δ: 8.28-8.26 (m, 1H), 7.64-7.20 (m, 13H), 6.94 (s, 1H), 5.28 (s, 2H).

(2) Synthesis of 1-(4-fluorophenyl)imidazo[1,2-a]quinolin-5-ol 5-(Benzyloxy)-1-(4-fluorophenyl)imidazo[1,2-a]quinoline (0.14 mmol) was dissolved in methylene chloride (3 mL) and the resulting mixture was cooled to 0° C. $BBr_3$ (1.68 mmol) was slowly added dropwise, and reaction mixture was slowly warmed to room temperature and stirred for 1 hours. The reaction was quenched by adding water, and the reaction mixture was extracted with ethyl acetate. Crude product was purified by recrystallization from methylene chloride and n-hexane, and obtained product was used for next step without further purification.

(3) Synthesis of Compound 2 (1-(4-fluorophenyl)imidazo[1,2-a]quinolin-4,5-dione)

1-(4-Fluorophenyl)imidazo[1,2-a]quinolin-5-ol (0.38 mmol) was dissolved in DMF (10 mL), to which IBX (0.38 mmol) was added in one-portion, and resulting mixture was stirred for 2 hours. When the reaction was completed, the reaction was quenched by adding sat. $NaHCO_3$. The reaction mixture was extracted with ethyl acetate, and combined organic layer was dried over $MgSO_4$ and concentrated under reduced pressure. Obtained product was purified by column chromatography.

Yield: 49%, Orange solid.

$^1H$ NMR (300 MHz, DMSO-$d_6$) δ: 8.02-7.99 (m, 1H), 7.60-7.55 (m, 2H), 7.50-7.37 (m, 5H), 6.94-6.92 (m, 1H).

Example 3: Synthesis of Compound 3 (1-isopropylimidazo[1,2-a]quinolin-4,5-dione)

(1) Synthesis of 5-(benzyloxy)-1-isopropylimidazo[1,2-a]quinoline

Using 4-(benzyloxy)quinolin-2-amine (0.3 mmol, Intermediate 1) and 3-methylbutanal (0.6 mmol) as a starting material and a reactant, the title compound was synthesized according to the procedure described in (1) of Example 1.

Yield: 41%, Yellow solid.

$^1H$ NMR (300 MHz, $CDCl_3$) δ: 8.31-8.22 (m, 2H), 7.65-7.60 (m, 1H), 7.52-7.28 (m, 7H) 6.90 (s, 1H), 5.28 (s, 2H), 3.78-3.69 (m, 1H), 1.48 (d, J=6.6 Hz, 6H).

(2) Synthesis of 1-isopropylimidazo[1,2-a]quinolin-5-ol

Using 5-(benzyloxy)-1-isopropylimidazo[1,2-a]quinoline (0.8 mmol) as a starting material, the title compound was synthesized according to the procedure described in (2) of Example 1, and obtained product was used for next step without further purification.

(3) Synthesis of Compound 3 (1-isopropylimidazo[1,2-a]quinolin-4,5-dione)

Using 1-isopropylimidazo[1,2-a]quinolin-5-ol as a starting material, the title compound was synthesized according to the procedure described in (3) of Example 1.

Yield: 17%, Orange solid.

$^1H$ NMR (300 MHz, $CDCl_3$) δ: 8.23-8.21 (m, 1H), 7.84-7.76 (m, 2H), 7.48-7.39 (m, 2H), 3.63-3.56 (m, 1H), 1.51 (d, J=6.6 Hz, 1H).

Example 4: Synthesis of Compound 4 (1-(4-(trifluoromethyl)phenyl)imidazo[1,2-a]quinolin-4,5-dione)

(1) Synthesis of 5-(benzyloxy)-1-(4-(trifluoromethyl)phenyl)imidazo[1,2-a]quinoline Using 4-(benzyloxy)quinolin-2-amine (0.3 mmol, Intermediate 1) and 2-(4-(trifluoromethyl)phenyl)acetaldehyde (0.6 mmol) as a starting material and a reactant, the title compound was synthesized according to the procedure described in (1) of Example 1.

Yield: 20%, Light yellow solid.

$^1H$ NMR (300 MHz, $CDCl_3$) δ: 8.30 (dd, J=7.9, 1.3 Hz, 1H), 7.75 (d, J=8.4 Hz, 2H), 7.64 (d, J=8.4 Hz, 2H), 7.55-7.36 (m, 9H), 6.95 (s, 1H), 5.30 (s, 2H).

(2) Synthesis of 1-(4-(trifluoromethyl)phenyl)imidazo[1,2-a]quinolin-5-ol

Using 5-(benzyloxy)-1-(4-(trifluoromethyl)phenyl)imidazo[1,2-a]quinoline (0.8 mmol) as a starting material, the title compound was synthesized according to the procedure described in (2) of Example 1. Obtained light brown solid was used for next step without further purification.

(3) Synthesis of Compound 4 (1-(4-(trifluoromethyl)phenyl)imidazo[1,2-a]quinoline-4,5-dione)

Using 1-(4-(trifluoromethyl)phenyl)imidazo[1,2-a]quinolin-5-ol as a starting material, the title compound was synthesized according to the procedure described in (3) of Example 1.

Yield: 43%, Orange solid.

$^{1}$H NMR (300 MHz, $CDCl_3$) δ: 8.23-8.20 (m, 1H), 7.84 (d, J=8.2 Hz, 2H), 7.68 (d, J=8.2 Hz, 2H), 7.50-7.37 (m, 3H), 7.05-7.02 (m, 1H).

Example 5: Synthesis of Compound 5 (ethyl 4,5-dioxo-4,5-dihydroimidazo[1,2-a]quinolin-2-carboxylate)

(1) Synthesis of ethyl 5-hydroxyimidazo[1,2-a]quinolin-2-carboxylate

Using ethyl 5-(benzyloxy)imidazo[1,2-a]quinolin-2-carboxylate (0.5 mmol, Intermediate 2) as a starting material, the title compound was synthesized according to the procedure described in (2) of Example 1, and obtained solid was used for next step without further purification.

(2) Synthesis of Compound 5 (ethyl 4,5-dioxo-4,5-dihydroimidazo[1,2-a]quinolin-2-carboxylate)

Using ethyl 5-hydroxyimidazo[1,2-a]quinolin-2-carboxylate (0.5 mmol) as a starting material, the title compound was synthesized according to the procedure described in (3) of Example 1.

Yield: 57%, Yellow solid.

$^{1}$H NMR (300 MHz, $CDCl_3$) δ: 8.37 (s, 1H), 8.29-8.26 (m, 1H), 7.88-7.86 (m, 1H), 7.66-7.55 (m, 2H), 4.46 (q, J=7.1 Hz, 2H), 1.44 (t, J=7.1 Hz, 3H).

Example 6: Synthesis of Compound 6 (ethyl 4,5-dioxo-1-phenyl-4,5-dihydroimidazo[1,2-a]quinolin-2-carboxylate)

(1) Synthesis of ethyl 5-(benzyloxy)-1-bromoimidazo[1,2-a]quinolin-2-carboxylate Ethyl 5-(benzyloxy)imidazo[1,2-a]quinolin-2-carboxylate (1 mmol, Intermediate 2) was dissolved in acetonitrile (10 mL). After stirring for 5 minutes, N-bromosuccinimide (1.1 mmol) was added, and resulting mixture was stirred at room temperature for 12 hours. When the reaction was completed, the reaction mixture was concentrated under reduced pressure and obtained product was purified by column chromatography.

Yield: 59%, Dark brown solid.

$^{1}$H NMR (300 MHz, DMSO-$d_6$) δ: 9.50 (d, J=8.6 Hz, 1H), 8.32 (d, J=8.2 Hz, 1H), 7.71-7.68 (m, 1H), 7.58-7.34 (m, 6H), 6.60 (s, 1H), 5.26 (s, 2H), 4.48 (q, J=7.2 Hz, 2H), 1.47 (t, J=7.2 Hz, 3H).

(2) Synthesis of ethyl 5-(benzyloxy)-1-phenylimidazo[1,2-a]quinolin-2-carboxylate Ethyl 5-(benzyloxy)-1-bromoimidazo[1,2-a]quinolin-2-carboxylate (1 mmol), $Pd(PPh_3)_4$ (5 mol %), $K_2CO_3$ (2.5 mmol) and phenylboronic acid (2 mmol) were dissolved in 1,4-dioxane (9.5 mL) and $H_2O$ (0.5 mL). Reaction mixture was stirred at 100° C. When the reaction was completed, water (50 mL) was added, and the reaction mixture was extracted with ethyl acetate. Combined organic layer was dried over $MgSO_4$ and concentrated under reduced pressure. Obtained product was purified by column chromatography.

Yield: 92%, Yellow solid.

$^{1}$H NMR (300 MHz, $CDCl_3$) δ: 8.27-8.25 (m, 1H), 7.58-7.39 (m, 10H), 7.25-7.16 (m, 2H), 6.95 (s, 1H), 5.29 (s, 2H), 4.27 (q, J=7.1 Hz, 2H), 1.23 (t, J=7.1 Hz, 3H).

(3) Synthesis of ethyl 5-hydroxy-1-phenylimidazo[1,2-a]quinolin-2-carboxylate

Using ethyl 5-(benzyloxy)-1-phenylimidazo[1,2-a]quinolin-2-carboxylate as a starting material, the title compound was synthesized according to the procedure described in (2) of Example 1, and obtained light brown product was used for next step without further purification.

(4) Synthesis of Compound 6 (ethyl 4,5-dioxo-1-phenyl-4,5-dihydroimidazo[1,2-a]quinolin-2-carboxylate)

Using ethyl 5-hydroxy-1-phenylimidazo[1,2-a]quinolin-2-carboxylate (0.5 mmol) as a starting material, the title compound was synthesized according to the procedure described in (3) of Example 1.

Yield: 54%, Dark yellow solid.

$^{1}$H NMR (300 MHz, $CDCl_3$) δ: 8.23-8.21 (m, 1H), 7.65-7.57 (m, 3H), 7.51-7.48 (m, 2H), 7.40-7.33 (m, 2H), 6.81-6.78 (m, 1H), 4.28 (q, J=7.1 Hz, 2H) 1.25 (t, J=7.1 Hz, 3H).

Example 7: Synthesis of Compound 7 (N,N-dimethyl-4,5-dioxo-1-phenyl-4,5-dihydroimidazo[1,2-a]quinolin-2-carboxamide)

(1) Synthesis of 4,5-dioxo-1-phenyl-4,5-dihydroimidazo[1,2-a]quinolin-2-carboxylic acid Ethyl 4,5-dioxo-1-phenyl-4,5-dihydroimidazo[1,2-a]quinolin-2-carboxylate (2 mmol, Compound 5) and LiOH (4 mmol) were dissolved in 1,4-dioxane (10 mL) and $H_2O$ (10 mL), and reaction mixture was stirred at 0° C. for 12 hours. When the reaction was completed, the reaction mixture was acidified with 3M aq. HCl to adjust pH 1. After adding water (100 mL), the resulting mixture was filtered to obtain white solid, which was dried and used for next step without further purification.

(2) Synthesis of Compound 7 (N,N-dimethyl-4,5-dioxo-1-phenyl-4,5-dihydroimidazo[1,2-a]quinolin-2-carboxamide)

4,5-Dioxo-1-phenyl-4,5-dihydroimidazo[1,2-a]quinolin-2-carboxylic acid (1 mmol), HATU (1.1 mmol), diisopropylethylamine (1.2 mmol) and dimethylamine (1.3 mmol) were dissolved in DMF (10 mL). After stirring at room temperature for 12 hours, water was added, and reaction mixture was then extracted with ethyl acetate. Organic layer was dried over $MgSO_4$ and concentrated under reduced pressure. Obtained product was purified by column chromatography.

Yield: 90%, Dark yellow solid.

$^1H$ NMR (300 MHz, $CDCl_3$) δ: 7.69-7.52 (m, 7H), 7.39-7.34 (m, 1H), 7.24-7.22 (m, 1H), 6.81-6.79 (m, 1H), 3.21 (s, 3H), 3.03 (s, 3H).

Example 8: Synthesis of Compound 8 (N-methyl-4,5-dioxo-1-phenyl-4,5-dihydroimidazo[1,2-a]quinolin-2-carboxamide)

Using 4,5-Dioxo-1-phenyl-4,5-dihydroimidazo[1,2-a]quinolin-2-carboxylic acid (1 mmol) prepared in (1) of Example 7 and methylamine in ethanol solution (1.3 mmol) as a starting material and a reactant, the title compound was synthesized according to the procedure described in (2) of Example 6.

Yield: 50%, Dark yellow solid.

$^1H$ NMR (300 MHz, $CDCl_3$) δ: 7.69-7.65 (m, 3H), 7.56-7.50 (m, 3H), 7.38-7.33 (m, 1H), 7.27-7.22 (m, 1H), 6.76-6.73 (m, 1H) 2.92 (s, 3H).

Example 9: Synthesis of Compound 9 (3-methyl-1-phenyl-1H-benzo[g]indazol-4,5-dione)

(1) 3-methyl-1-phenyl-1H-benzo[g]indazol-5-ol

Using intermediate 5 as a starting material, the title compound was synthesized according to the procedure described in (2) of Example 1.

Yield: 80%, Light brown solid.

$^1H$ NMR (300 MHz, $CDCl_3$) δ: 8.33-8.31 (m, 1H), 7.63-7.51 (m, 7H), 7.37-7.32 (m, 1H), 6.96 (s, 3H), 5.33 (br s, 1H), 2.61 (s, 3H).

(2) Synthesis of Compound 9 (3-methyl-1-phenyl-1H-benzo[g]indazol-4,5-dione)

Using 3-methyl-1-phenyl-1H-benzo[g]indazol-5-ol as a starting material, the title compound was synthesized according to the procedure described in (3) of Example 1.

Yield: 70%, Yellow solid.

$^1H$ NMR (300 MHz, $CDCl_3$) δ: 8.19-8.16 (m, 1H), 7.64-7.62 (m, 3H), 7.56-7.51 (m, 2H), 7.46-7.31 (m, 2H), 6.89-6.86 (m, 1H), 2.63 (s, 3H).

Example 10: Synthesis of Compound 10 (3-isopropyl-1-phenyl-1H-benzo[g]indazol-4,5-dione)

(1) Synthesis of 5-methoxy-1-phenyl-1H-benzo[g]indazol-3-carbaldehyde (5-Methoxy-1-phenyl-1H-benzo[g]indazol-3-yl)methanol (26.17 mmol, Intermediate 6) was dissolved in methylene chloride (100 mL). PCC (26.17 mmol) and Celite (5.64 g) were added, and then resulting mixture was stirred for 30 minutes. When the reaction was completed, water was added, and the reaction mixture was then extracted with methylene chloride. Extract was washed with brine, dried over $MgSO_4$ and concentrated under reduced pressure.

Obtained product was purified by column chromatography.

Yield: 66%, Light brown solid.

$^1H$ NMR (300 MHz, $CDCl_3$) δ: 10.22 (s, 1H), 8.28 (d, J=8.2 Hz, 1H), 7.49-7.46 (m, 5H), 7.44-7.36 (m, 2H), 7.25 (t, J=7.8 Hz, 1H), 6.96 (s, 1H), 4.02 (s, 3H).

(2) Synthesis of 1-(5-methoxy-1-phenyl-1H-benzo[g]indazol-3-yl)ethan-1-ol

5-Methoxy-1-phenyl-1H-benzo[g]indazol-3-carbaldehyde (9.59 mmol) was dissolved in THF. The reaction solution was cooled to below 0° C., methylmagnesium bromide solution (24 mmol, 3M solution in THF) was slowly added, and resulting mixture was stirred for 5 hours. When the reaction was completed, the reaction was quenched by adding sat. aq. ammonium chloride, and the reaction mixture was extracted with ethyl acetate. The extract was washed with brine, dried over $MgSO_4$, and concentrated under reduced pressure, and obtained product was purified by column chromatography.

Yield: 92%, Light yellow solid.

$^1H$ NMR (300 MHz, $CDCl_3$) δ: 8.36 (d, J=8.2 Hz, 1H), 7.53-7.48 (m, 7H), 7.31-7.28 (m, 1H), 7.12 (m, 1H), 5.41-5.39 (m, 1H), 4.05 (s, 3H), 1.78 (d, J=6.4 Hz, 3H).

(3) Synthesis of 1-(5-methoxy-1-phenyl-1H-benzo[g]indazol-3-yl)ethan-1-one

Using 1-(5-methoxy-1-phenyl-1H-benzo[g]indazol-3-yl)ethan-1-ol as a starting material, the title compound was synthesized according to the procedure described in (1) of Example 10.

Yield: 80%, Light yellow solid.

$^1H$ NMR (300 MHz, $CDCl_3$) δ: 8.40 (d, J=2.8 Hz, 1H), 7.73 (s, 1H), 7.63-7.57 (m, 5H), 7.56-7.51 (m, 1H), 7.48-7.44 (m, 1H), 7.36-7.34 (m, 1H), 4.05 (s, 3H), 2.77 (s, 3H).

(4) Synthesis of 5-methoxy-1-phenyl-3-(prop-1-en-2-yl)-1H-benzo[g]indazole

Methyltriphenylphosphonium bromide (35.3 mmol) was dissolved in THF (50 mL). After cooling to −78° C., n-butyllithium solution (35.3 mmol, 2.5M solution in hexane) was added dropwise and resulting mixture was stirred for 2 hours. 1-(5-Methoxy-1-phenyl-1H-benzo[g]indazol-3-yl)ethan-1-one (7.06 mmol) in THF (20 mL) was added at the same temperature, and the resulting mixture was slowly warmed to room temperature with stirring. When the reaction was completed, sat. aq. $NH_4Cl$ was added, and the reaction mixture was then extracted with ethyl acetate. The extract was washed with brine, dried over $MgSO_4$ and concentrated under reduced pressure, and obtained product was purified by column chromatography.

Yield: 95%, Yellow solid.

$^1H$ NMR (300 MHz, $CDCl_3$) δ: 8.38 (d, J=2.9 Hz, 1H), 7.57-7.50 (m, 6H), 7.35-7.30 (m, 1H), 7.22 (s, 1H), 5.76 (s, 1H), 5.47 (s, 1H), 4.09 (s, 3H), 2.39 (s, 3H).

(5) Synthesis of 3-isopropyl-5-methoxy-1-phenyl-1H-benzo[g]indazole

5-Methoxy-1-phenyl-3-(prop-1-en-2-yl)-1H-benzo[g]indazole (6.71 mmol) and Pd/C (5 mol %) were dissolved in methanol (50 mL). The resulting mixture was stirred under hydrogen atmosphere for overnight at room temperature. When the reaction was completed, the reaction mixture was filtered through Celite pad, filtrate was concentrated under reduced pressure, and obtained product was purified by column chromatography.

Yield: 40%, White solid.

$^1H$ NMR (300 MHz, $CDCl_3$) δ: 8.37 (d, J=2.8 Hz, 1H), 7.62-7.48 (m, 7H), 7.35-7.30 (m, 1H), 6.86 (s, 1H), 4.09 (s, 3H) 3.54-3.43 (m, 1H), 1.56-1.53 (d, J=6.5 Hz, 6H).

(6) Synthesis of 3-isopropyl-1-phenyl-1H-benzo[g]indazol-5-ol

Using 3-isopropyl-5-methoxy-1-phenyl-1H-benzo[g]indazole as a starting material, the title compound was synthesized according to the procedure described in (2) of Example 1.

Yield: 95%, Light brown solid.

$^1$H NMR (300 MHz, $CDCl_3$) δ: 8.21 (d, J=8.2 Hz, 1H), 7.60-7.49 (m, 7H), 7.33-7.29 (m, 1H), 6.97 (s, 1H), 6.67 (s, 1H), 3.39-3.32 (m, 1H), 1.46-1.44 (d, J=6.5 Hz, 6H).

(7) Synthesis of Compound 10 (3-isopropyl-1-phenyl-1H-benzo[g]indazol-4,5-dione)

Using 3-isopropyl-1-phenyl-1H-benzo[g]indazol-5-ol as a starting material, the title compound was synthesized according to the procedure described in (3) of Example 1.

Yield: 96%, Yellow solid.

$^1$H NMR (300 MHz, $CDCl_3$) δ: 8.15 (d, J=7.7 Hz, 1H), 7.62-7.61 (m, 3H), 7.55-7.53 (m, 2H), 7.40 (t, J=7.6 Hz, 1H), 7.32 (m, 1H), 6.82 (d, J=2.6 Hz, 1H), 3.57 (m, 1H), 1.39 (d, J=2.2 Hz, 6H).

Example 11: Synthesis of Compound 11 (3-heptyl-1-phenyl-1H-benzo[g]indazol-4,5-dione)

(1) Synthesis of 3-(hept-1-en-1-yl)-5-methoxy-1-phenyl-1H-benzo[g]indazole

Using 1-(5-methoxy-1-phenyl-1H-benzo[g]indazol-3-yl) ethan-1-one (7.06 mmol) prepared in (1) of Example 10 and n-hexyltriphenylphosphonium bromide (35.3 mmol) as a starting material and a reactant, the title compound was synthesized according to the procedure described in (4) of Example 9.

Yield: 95%, Yellow solid.

$^1$H NMR (300 MHz, $CDCl_3$) δ: 8.39 (d, J=8.2 Hz, 1H), 7.66-7.50 (m, 7H), 7.35 (t, J=7.6 Hz, 1H), 6.97 (s, 1H), 6.69 (d, J=11.2 Hz, 1H), 6.00 (m, 1H), 4.09 (s, 3H), 2.67 (m, 2H), 1.53 (m, 2H), 1.48-1.28 (m, 4H), 0.88 (t, J=5.5 Hz, 3H).

(2) Synthesis of 3-heptyl-5-methoxy-1-phenyl-1H-benzo[g]indazole

Using 3-(hept-1-en-1-yl)-5-methoxy-1-phenyl-1H-benzo [g]indazole (9.11 mmol) as a starting material, the title compound was synthesized according to the procedure described in (5) of Example 10.

Yield: 96%, White solid.

$^1$H NMR (300 MHz, $CDCl_3$) δ: 8.37 (d, J=8.2 Hz, 1H), 7.62-7.49 (m, 7H), 7.33 (t, J=7.6 Hz, 1H), 6.94 (s, 1H), 4.09 (s, 3H), 3.03 (t, J=7.6 Hz, 2H), 1.88 (m, 2H), 1.48-1.27 (m, 8H), 0.87 (t, J=5.5 Hz, 3H).

(3) Synthesis of 3-heptyl-1-phenyl-1H-benzo[g]indazol-5-ol

Using 3-heptyl-5-methoxy-1-phenyl-1H-benzo[g]indazole as a starting material, the title compound was synthesized according to the procedure described in (2) of Example 1, and obtained product was used for next step without further purification.

(4) Synthesis of Compound 11 (3-heptyl-1-phenyl-1H-benzo[g]indazol-4,5-dione)

Using 3-heptyl-1-phenyl-1H-benzo[g]indazol-5-ol as a starting material, the title compound was synthesized according to the procedure described in (3) of Example 1.

Yield: 86%, Yellow solid.

$^1$H NMR (300 MHz, $CDCl_3$) δ: 8.16 (d, J=7.6 Hz, 1H), 7.64-7.62 (m, 3H), 7.55-7.53 (m, 2H), 7.43 (t, J=7.6 Hz, 1H), 7.33 (t, J=7.6 Hz, 1H), 6.86 (d, J=7.6 Hz, 1H), 2.99 (t, J=7.6 Hz, 2H), 1.77 (m, 2H), 1.43-1.11 (m, 8H), 0.86 (t, J=5.9 Hz, 3H).

Example 12: Synthesis of Compound 12 (3-phenethyl-1-phenyl-1H-benzo[g]indazol-4,5-dione)

(1) Synthesis of 5-methoxy-1-phenyl-3-styryl-1H-benzo[g]indazole

Using 1-(5-methoxy-1-phenyl-1H-benzo[g]indazol-3-yl) ethan-1-one (9.6 mmol) prepared in (1) of Example 10 and benzyltriphenylphosphonium bromide (47.9 mmol), the title compound was synthesized according to the procedure described in (4) of Example 9.

Yield: 96%, Yellow solid.

$^1$H NMR (300 MHz, $CDCl_3$) δ: 8.39 (d, J=7.7 Hz, 1H), 7.62-7.51 (m, 10H), 7.42-7.34 (m, 3H), 7.32-7.24 (m, 2H), 7.20 (s, 1H), 4.14 (s, 3H).

(2) Synthesis of 5-methoxy-3-phenethyl-1-phenyl-1H-benzo[g]indazole

Using 5-methoxy-1-phenyl-3-styryl-1H-benzo[g]indazole (9.21 mmol) as a starting material, the title compound was synthesized according to the procedure described in (5) of Example 10.

Yield: 98%, White solid $^1$H NMR (300 MHz, $CDCl_3$) δ: 8.35 (d, J=8.2 Hz, 1H), 7.60-7.58 (m, 6H), 7.51 (t, J=7.6 Hz, 1H), 7.35-7.30 (m, 1H), 7.31-7.29 (m, 5H), 6.71 (s, 1H), 4.00 (s, 3H), 3.36 (t, J=7.4 Hz, 2H), 3.20 (t, J=7.4 Hz, 2H).

(3) Synthesis of 3-phenethyl-1-phenyl-1H-benzo[g]indazol-5-ol

Using 5-methoxy-3-phenethyl-1-phenyl-1H-benzo[g]indazole as a starting material, the title compound was synthesized according to the procedure described in (2) of Example 1, and obtained product was used for next step without further purification.

(4) Synthesis of Compound 12 (3-phenethyl-1-phenyl-1H-benzo[g]indazol-4,5-dione)

Using 3-isopropyl-1-phenyl-1H-benzo[g]indazol-5-ol as a starting material, the title compound was synthesized according to the procedure described in (3) of Example 1.

Yield: 66%, Yellow solid.

$^1$H NMR (300 MHz, $CDCl_3$) δ: 8.17 (d, J=7.6 Hz, 1H), 7.64-7.62 (m, 3H), 7.53-7.52 (m, 2H), 7.45 (t, J=7.6 Hz, 1H), 7.37-7.29 (m, 5H), 7.24 (t, J=7.6 Hz, 1H), 6.87 (d, J=7.6 Hz, 1H), 3.30 (t, J=7.0 Hz, 2H), 3.11 (t, J=7.0 Hz, 2H).

Example 13: Synthesis of Compound 13 (1,3-diphenyl-1H-benzo[g]indazol-4,5-dione)

(1) Synthesis of (1-bromo-4-methoxynaphthalen-2-yl) (phenyl) methanone

Using 1-bromo-N,4-dimethoxy-N-methyl-2-naphthamide prepared in (1) of Preparation Example 4 and phenylmagnesium bromide, the title compound was synthesized according to the procedure described in (2) of Preparation Example 4.

Yield: 80%, White solid $^1$H NMR (300 MHz, DMSO-$d_6$) δ: 8.35-8.29 (m, 2H), 7.79-7.67 (m, 5H), 7.57-7.54 (m, 2H), 7.05 (s, 1H), 3.97 (s, 3H).

(2) Synthesis of 1-((1-bromo-4-methoxynaphthalen-2-yl) (phenyl)methylene)-2-phenylhydrazine Using (1-bromo-4-methoxynaphthalen-2-yl) (phenyl) methanone as a starting material, the title compound was synthesized according to the procedure described in (1) of Preparation Example 5.

(3) Synthesis of 5-methoxy-1,3-diphenyl-1H-benzo [g]indazole)

Using 1-((1-bromo-4-methoxynaphthalen-2-yl) (phenyl) methylene)-2-phenylhydrazine as a starting material, the title compound was synthesized according to the procedure described in (2) of Preparation Example 5.

Yield: 50%, Light brown solid.

$^1$H NMR (300 MHz, DMSO-$d_6$) δ: 8.29 (d, J=2.8 Hz, 1H), 7.91-7.88 (m, 2H), 7.55-7.36 (m, 9H), 7.34-7.28 (m, 1H), 7.25-7.19 (m, 1H), 6.89 (s, 1H), 3.98 (s, 3H).

(4) Synthesis of 1,3-diphenyl-1H-benzo[g]indazol-5-ol

Using 5-methoxy-1,3-diphenyl-1H-benzo[g]indazole as a starting material, the title compound was synthesized according to the procedure described in (2) of Example 1.

Yield: 90%, Light brown solid $^1$H NMR (300 MHz, DMSO-$d_6$) δ: 8.20 (d, J=2.9 Hz, 1H), 7.89-7.85 (m, 2H), 7.52-7.38 (m, 9H), 7.30-7.28 (m, 1H), 7.23-7.16 (m, 1H), 6.85 (br s, 1H).

(5) Synthesis of Compound 13 (1,3-diphenyl-1H-benzo[g]indazol-4,5-dione)

Using 1,3-diphenyl-1H-benzo[g]indazol-5-ol as a starting material, the title compound was synthesized according to the procedure described in (3) of Example 1.

Yield: 94%, Yellow solid.

$^1$H NMR (300 MHz, DMSO-$d_6$) δ: 8.21-8.15 (m, 3H), 7.68-7.61 (m, 5H), 7.48-7.44 (m, 4H), 7.39-7.34 (m, 1H), 6.82 (d, J=1.8 Hz, 1H).

Example 14: Synthesis of Compound 14 (3-(4-fluorophenyl)-1-phenyl-1H-benzo[g]indazol-4,5-dione)

(1) Synthesis of (1-bromo-4-methoxynaphthalen-2-yl) (4-fluorophenyl)methanone

Using 1-bromo-N,4-dimethoxy-N-methyl-2-naphthamide prepared in (1) of Preparation Example 4 and 4-fluorophenylmagnesium bromide, the title compound was synthesized according to the procedure described in (2) of Preparation Example 4.

Yield: 80%, White solid.

$^1$H NMR (300 MHz, DMSO-$d_6$) δ: 8.34-8.29 (m, 2H), 7.79-7.65 (m, 5H), 7.56-7.54 (m, 1H), 7.03 (s, 1H), 3.97 (s, 3H).

(2) Synthesis of 1-((1-bromo-4-methoxynaphthalen-2-yl) (4-fluorophenyl)methylene)-2-phenylhydrazine Using (1-bromo-4-methoxynaphthalen-2-yl) (4-fluorophenyl)methanone as a starting material, the title compound was synthesized according to the procedure described in (1) of Preparation Example 5.

(3) Synthesis of 3-(4-fluorophenyl)-5-methoxy-1-phenyl-1H-benzo[g]indazole

Using 1-((1-bromo-4-methoxynaphthalen-2-yl) (4-fluorophenyl)methylene)-2-phenylhydrazine as a starting material, the title compound was synthesized according to the procedure described in (2) of Preparation Example 5.

Yield: 45%, Light gray solid.

$^1$H NMR (300 MHz, DMSO-$d_6$) δ: 8.27 (d, J=2.8 Hz, 1H), 7.87-7.84 (m, 2H), 7.56-7.39 (m, 8H), 7.33-7.28 (m, 1H), 7.23-7.21 (m, 1H), 6.72 (s, 1H), 3.98 (s, 3H).

(4) Synthesis of 3-(4-fluorophenyl)-1-phenyl-1H-benzo[g]indazol-5-ol

Using 3-(4-fluorophenyl)-5-methoxy-1-phenyl-1H-benzo [g]indazole as a starting material, the title compound was synthesized according to the procedure described in (2) of Example 1.

Yield: 89%, Light brown solid.

$^1$H NMR (300 MHz, DMSO-$d_6$) δ: 8.23 (d, J=2.8 Hz, 1H), 7.86-7.82 (m, 2H), 7.54-7.34 (m, 8H), 7.31-7.28 (m, 1H), 7.20-7.18 (m, 1H), 6.70 (br s, 1H).

(5) Synthesis of Compound 14 (3-(4-fluorophenyl)-1-phenyl-1H-benzo[g]indazol-4,5-dione)

Using 3-(4-fluorophenyl)-1-phenyl-1H-benzo[g]indazol-5-ol as a starting material, the title compound was synthesized according to the procedure described in (3) of Example 1.

Yield: 90%, Yellow solid.

$^1$H NMR (300 MHz, DMSO-$d_6$) δ: 8.19-8.17 (m, 3H, 7.78-7.60 (m, 5H), 7.48-7.43 (m, 1H), 7.37-7.33 (m, 1H), 7.16-7.11 (m, 2H), 6.87 (d, J=7.7 Hz, 1H).

Example 15: Synthesis of Compound 15 (3-(3,4-difluorophenyl)-1-phenyl-1H-benzo[g]indazol-4,5-dione)

(1) Synthesis of (1-bromo-4-methoxynaphthalen-2-yl) (3,4-difluorophenyl)methanone Using 1-bromo-N,4-dimethoxy-N-methyl-2-naphthamide prepared in (1) of Preparation Example 4 and 3,4-difluorophenylmagnesium bromide, the title compound was synthesized according to the procedure described in (2) of Preparation Example 4.

Yield: 75%, White solid.

$^1$H NMR (300 MHz, DMSO-$d_6$) δ: 8.30-8.26 (m, 2H), 7.76-7.62 (m, 4H), 7.53-7.50 (m, 1H), 7.01 (s, 1H), 3.96 (s, 3H).

(2) Synthesis of 1-((1-bromo-4-methoxynaphthalen-2-yl) (3,4-difluorophenyl)methylene)-2-phenylhydrazine Using (1-bromo-4-methoxynaphthalen-2-yl) (3,4-difluorophenyl)methanone as a starting material, the title compound was synthesized according to the procedure described in (1) of Preparation Example 5.

(3) Synthesis of 3-(3,4-difluorophenyl)-5-methoxy-1-phenyl-1H-benzo[g]indazole

Using 1-((1-bromo-4-methoxynaphthalen-2-yl) (3,4-difluorophenyl)methylene)-2-phenylhydrazine as a starting material, the title compound was synthesized according to the procedure described in (2) of Preparation Example 5.

Yield: 40%, Light gray solid.

$^1$H NMR (300 MHz, DMSO-$d_6$) δ: 8.22 (d, J=2.8 Hz, 1H), 7.84-7.81 (m, 2H), 7.52-7.34 (m, 7H), 7.30-7.28 (m, 1H), 7.20-7.17 (m, 1H), 6.68 (s, 1H), 3.96 (s, 3H).

(4) Synthesis of 3-(3,4-difluorophenyl)-1-phenyl-1H-benzo[g]indazole-5-ol

Using 3-(3,4-difluorophenyl)-5-methoxy-1-phenyl-1H-benzo[g]indazole as a starting material, the title compound was synthesized according to the procedure described in (2) of Example 1.

Yield: 92%, Light brown solid.

$^1$H NMR (300 MHz, DMSO-$d_6$) δ: 8.20 (d, J=2.8 Hz, 1H), 7.84-7.80 (m, 2H), 7.50-7.30 (m, 7H), 7.29-7.28 (m, 1H), 7.19-7.16 (m, 1H), 6.63 (br s, 1H).

(5) Synthesis of Compound 15 (3-(3,4-difluorophenyl)-1-phenyl-1H-benzo[g]indazol-4,5-dione)

Using 3-(3,4-difluorophenyl)-1-phenyl-1H-benzo[g]indazol-5-ol as a starting material, the title compound was synthesized according to the procedure described in (3) of Example 1.

Yield: 94%, Yellow solid.

$^1$H NMR (300 MHz, DMSO-$d_6$) δ: 8.19-8.04 (m, 3H), 7.68-7.66 (m, 3H), 7.66-7.60 (m, 2H), 7.47-7.44 (m, 1H), 7.39-7.33 (m, 1H), 7.25-7.22 (m, 1H), 6.88-6.86 (m, 1H).

Example 16: Synthesis of Compound 16 (3-(bromomethyl)-1-phenyl-1H-benzo[g]indazol-4,5-dione)

Using 3-(bromomethyl)-1-phenyl-1H-benzo[g]indazol-5-ol prepared in (2) of Preparation Example 7 as a starting material, the title compound was synthesized according to the procedure described in (3) of Example 1 Yield: 46%, Yellow solid.

$^1$H NMR (300 MHz, $CDCl_3$) δ: 8.20 (d, J=7.6 Hz, 1H), 7.66-7.62 (m, 3H), 7.58-7.55 (m, 2H), 7.48 (t, J=7.2 Hz, 1H), 7.37 (t, J=7.6 Hz, 1H), 6.89 (d, J=8.2 Hz, 1H), 4.80 (s, 2H)

Example 17: Synthesis of Compound 17 (3-((dimethylamino)methyl)-1-phenyl-1H-benzo[g]indazol-4,5-dione)

3-(bromomethyl)-1-phenyl-1H-benzo[g]indazol-4,5-dione (3.50 mmol, Compound 16) was dissolved in THF (30 mL). After cooling to 0° C., dimethylamine (35.0 mmol) was added, and reaction mixture was warmed up to room temperature and stirred. When the reaction was completed, the reaction was quenched by adding water. The reaction mixture was extracted with ethyl acetate, and extract was washed with brine, dried over $MgSO_4$ and concentrated under reduced pressure. Obtained product was purified by column chromatography.

Yield: 58%, Yellow solid.

$^1$H NMR (300 MHz, $CDCl_3$) δ: 8.16 (d, J=7.6 Hz, 1H), 7.63-7.61 (m, 3H), 7.55-7.52 (m, 2H), 7.43 (t, J=7.6 Hz, 1H), 7.34 (t, J=7.6 Hz, 1H), 6.86 (d, J=7.6 Hz, 1H), 3.91 (s, 2H), 2.44 (s, 6H).

Example 18: Synthesis of Compound 18 (3-(methoxymethyl)-1-phenyl-1H-benzo[g]indazol-4,5-dione)

(1) Synthesis of 5-(methoxymethoxy)-3-(methoxymethyl)-1-phenyl-1H-benzo[g]indazole NaH (3.65 mmol) was dissolved in methanol (4.86 mmol) and DMF (20 mL) mixture, and resulting mixture was stirred at 0° C. for 30 minutes. 3-(Bromomethyl)-5-(methoxymethoxy)-1-phenyl-1H-benzo[g]indazole (2.43 mmol, Intermediate 7) was added, and reaction mixture was stirred at room temperature. When the reaction was completed, the reaction was quenched by adding water, and the reaction mixture was extracted with ethyl acetate. Extract was washed with brine, dried over $MgSO_4$ and concentrated under reduced pressure, and obtained product was purified by column chromatography.

Yield: 95%, Light yellow solid.

$^1$H NMR (300 MHz, $CDCl_3$) δ: 8.40 (d, J=8.2 Hz, 1H), 7.62-7.56 (m, 6H), 7.55-7.52 (m, 1H), 7.41-7.37 (m, 1H), 7.35 (t, J=8.4 Hz, 1H), 5.48 (s, 2H), 4.91 (s, 2H), 3.61 (s, 3H), 3.50 (s, 3H).

(2) Synthesis of 3-(methoxymethyl)-1-phenyl-1H-benzo[g]indazol-5-ol 5-(Methoxymethoxy)-3-(methoxymethyl)-1-phenyl-1H-benzo[g]indazole (2.31 mmol) was dissolved in methanol (20 mL). While stirring at room temperature, conc. HCl (2 drops) was added, and reaction mixture was stirred at reflux. When the reaction was completed, the reaction mixture was concentrated under reduced pressure, to which water was added, and then extracted with ethyl acetate. Organic layer was dried over $MgSO_4$ and concentrated under reduced pressure, and obtained product was used for next step without further purification.

(3) Synthesis of Compound 18 (3-(methoxymethyl)-1-phenyl-1H-benzo[g]indazol-4,5-dione)

Using 3-(methoxymethyl)-1-phenyl-1H-benzo[g]indazol-5-ol as a starting material, the title compound was synthesized according to the procedure described in (3) of Example 1.

Yield: 75%, Yellow solid.

$^1$H NMR (300 MHz, $CDCl_3$) δ: 8.16 (d, J=7.6 Hz, 1H), 7.63-7.61 (m, 3H), 7.55-7.52 (m, 2H), 7.44 (t, J=7.6 Hz, 1H), 7.34 (t, J=7.6 Hz, 1H), 6.87 (d, J=7.6 Hz, 1H), 4.86 (s, 2H), 3.57 (s, 3H).

Example 19: Synthesis of Compound 19 (3-(isopropoxy)-1-phenyl-1H-benzo[g]indazol-4,5-dione)

(1) Synthesis of 3-(isopropoxymethyl)-5-(methoxymethoxy)-1-phenyl-1H-benzo[g]indazole Using isopropanol (0.37 mL) and 3-(bromomethyl)-5-(methoxymethoxy)-1-phenyl-1H-benzo[g]indazole (2.43 mmol, Intermediate 7, the title compound was synthesized according to the procedure described in (1) of Example 18.

Yield: 39%, Light yellow solid.

$^1$H NMR (300 MHz, $CDCl_3$) δ: 8.40 (d, J=8.2 Hz, 1H), 7.62-7.58 (m, 6H), 7.54-7.49 (m, 2H), 7.32 (t, J=7.4 Hz, 1H), 5.46 (s, 2H), 4.97 (s, 2H), 3.87-3.84 (m, 1H), 3.60 (s, 3H), 1.29 (d, J=5.9 Hz, 6H).

(2) Synthesis of 3-(isopropoxymethyl)-1-phenyl-1H-benzo[g]indazol-5-ol

Using 3-(isopropoxymethyl)-5-(methoxymethoxy)-1-phenyl-1H-benzo[g]indazole as a starting material, the title compound was synthesized according to the procedure described in (2) of Example 18, and obtained product was used for next step without further purification.

(3) Synthesis of Compound 19 (3-(isopropoxymethyl)-1-phenyl-1H-benzo[g]indazol-4,5-dione)

Using 3-(isopropoxymethyl)-1-phenyl-1H-benzo[g]indazol-5-ol as a starting material, the title compound was synthesized according to the procedure described in (3) of Example 1.

Yield: 53%, Yellow solid.

$^1$H NMR (300 MHz, $CDCl_3$) δ: 8.16 (d, J=7.6 Hz, 1H), 7.62-7.60 (m, 3H), 7.54-7.53 (m, 2H), 7.43 (t, J=7.6 Hz, 1H), 7.33 (t, J=7.6 Hz, 1H), 6.84 (d, J=7.6 Hz, 1H), 4.84 (s, 2H), 3.90 (m, 1H), 1.27 (d, J=6.4 Hz, 6H).

Example 20: Synthesis of Compound 20 (1-isopropyl-3-methyl-1H-benzo[g]indazol-4,5-dione) and Compound 21 (2-isopropyl-3-methyl-2H-benzo[g]indazol-4,5-dione)

(1) Synthesis of a mixture of 1-isopropyl-5-methoxy-3-methyl-1H-benzo[g]indazole and 2-isopropyl-5-methoxy-3-methyl-2H-benzo[g]indazole 5-Methoxy-3-methyl-1H-benzo[g]indazole (2.1 mmol, Intermediate 8) was dissolved in DMF. After cooling to 0° C., NaH (3.18 mmol) was added, and the resulting mixture was warmed up to room temperature and stirred. 2-Bromopropane (4.24 mmol) was added, and reaction mixture was stirred for 8 hours. The reaction was quenched by adding $H_2O$ and the reaction mixture was extracted with ethyl acetate. Organic layer was dried over $MgSO_4$ and concentrated under reduced pressure, to obtain a mixture of 1-isopropyl-5-methoxy-3-methyl-1H-benzo[g]indazole and 2-isopropyl-5-methoxy-3-methyl-2H-benzo[g]indazole, which was used for next step without further purification.

(2) Synthesis of a mixture of 1-isopropyl-3-methyl-1H-benzo[g]indazol-5-ol and 2-isopropyl-3-methyl-2H-benzo[g]indazol-5-ol Using the mixture of 1-isopropyl-5-methoxy-3-methyl-1H-benzo[g]indazole and 2-isopropyl-5-methoxy-3-methyl-2H-benzo[g]indazole as a starting material, a mixture of the title compounds was synthesized according to the procedure described in (2) of Example 1 and the mixture was used for next step without further purification.

(3) Synthesis of Compound 20 (1-isopropyl-3-methyl-1H-benzo[g]indazol-4,5-dione) and Compound 21 (2-isopropyl-3-methyl-2H-benzo[g]indaxol-4,5-dione)

Using the mixture of 1-isopropyl-3-methyl-1H-benzo[g]indazol-5-ol and 2-isopropyl-3-methyl-2H-benzo[g]indazol-5-ol as a starting material, a mixture of the title compounds was synthesized according to the procedure described in (3) of Example 1, from which Compound 20 and compound 21 were separated.

(Compound 20) Yield: 7%, Yellow solid.

$^1$H NMR (300 MHz, $CDCl_3$) δ: 8.04-8.01 (m, 2H), 7.82-7.77 (m, 1H), 7.61-7.56 (m, 1H), 5.22-5.14 (m, 1H), 2.39 (s, 3H), 1.51 (d, J=5.9 Hz, 6H).

(Compound 21) Yield: 6%, Yellow solid.

$^1$H NMR (300 MHz, $CDCl_3$) δ: 8.11-8.03 (m, 2H), 7.66-7.62 (m, 1H), 7.45-7.40 (m, 1H), 4.54-4.50 (m, 1H), 2.65 (s, 3H), 1.56 (d, J=6.5 Hz, 6H).

Example 21: Synthesis of Compound 22 (1,3-dimethyl-1H-benzo[g]indazol-4,5-dione) and compound 23 (2,3-dimethyl-2H-benzo[g]indazol-4,5-dione)

(1) Synthesis of a mixture of 5-methoxy-1,3-dimethyl-1H-benzo[g]indazole and 5-methoxy-2,3-dimethyl-2H-benzo[g]indazole Using 5-methoxy-3-methyl-1H-benzo[g]indazole (2.1 mmol, Intermediate 8) and iodomethane (4.24 mmol), a mixture of the title compounds was synthesized according to the procedure described in (1) of Example 20, and the mixture was used for next step without further purification.

(2) Synthesis of a mixture of 1,3-dimethyl-1H-benzo[g]indazol-5-ol and 2,3-dimethyl-2H-benzo[g]indazol-5-ol Using the mixture of 5-methoxy-1,3-dimethyl-1H-benzo[g]indazole and 5-methoxy-2,3-dimethyl-2H-benzo[g]indazole as a starting material, a mixture of the title compounds was synthesized according to the procedure described in (2) of Example 1, and the mixture was used for next step without further purification.

(3) Synthesis of Compound 22 (1,3-dimethyl-1H-benzo[g]indazol-4,5-dione) and Compound 23 (2,3-dimethyl-2H-benzo[g]indazol-4,5-dione)

Using the mixture of 1,3-dimethyl-1H-benzo[g]indazol-5-ol and 2,3-dimethyl-2H-benzo[g]indazol-5-ol as a starting material, a mixture of the title compounds was synthesized according to the procedure described in (3) of Example 1, from which Compound 22 and Compound 23 were separated.

(Compound 22) Yield: 2%, Yellow solid $^1$H NMR (300 MHz, $CDCl_3$) δ: 8.25-8.20 (m, 1H), 7.83-7.79 (m, 1H), 7.76-7.72 (m, 1H), 7.56-7.52 (m, 1H), 4.26 (s, 3H), 2.55 (s, 3H).

(Compound 23) Yield: 1.5%, Yellow solid.

$^1$H NMR (300 MHz, $CDCl_3$) δ: 8.14-8.10 (m, 1H), 7.98-7.93 (m, 1H), 7.68-7.64 (m, 1H), 7.49-7.46 (m, 1H), 3.89 (s, 3H), 2.66 (s, 3H).

Example 22: Synthesis of Compound 24 (3-((1H-imidazol-1-yl)methyl)-1-phenyl-1H-benzo[g]indazol-4,5-dione)

(1) Synthesis of 3-((1H-imidazol-1-yl)methyl)-5-methoxy-1-phenyl-1H-benzo[g]indazole 3-(Bromomethyl)-5-methoxy-1-phenyl-1H-benzo[g]indazole (0.33 mmol) prepared in (1) of Preparation Example 7 and imidazole (0.66 mmol) were dissolved in DMF. After cooling to 0° C., NaH (3.18 mmol) was added, and reaction mixture was warmed up to room temperature and stirred for 12 hours. The reaction was quenched by adding $H_2O$ and the reaction mixture was extracted with ethyl acetate. Organic layer was dried over $MgSO_4$ and concentrated under reduced pressure, and obtained product was purified by column chromatography.

$^1$H NMR (300 MHz, $CDCl_3$) δ: 8.34 (m, 1H), 7.75 (s, 1H), 7.60-7.50 (m, 7H), 7.34 (m, 1H), 7.10 (m, 2H), 6.45 (m, 1H), 5.55 (s, 2H), 3.95 (s, 3H).

(2) Synthesis of 3-((1H-imidazol-1-yl)methyl)-1-phenyl-1H-benzo[g]indazol-5-ol Using 3-((1H-imidazol-1-yl)methyl)-5-methoxy-1-phenyl-1H-benzo[g]indazole as a starting material, the title compound was synthesized according to the procedure described in (2) of Example 1, and obtained product was used for next step without further purification.

(3) Synthesis of Compound 24 (3-((1H-imidazol-1-yl)methyl)-1-phenyl-1H-benzo[g]indazol-4,5-dione)

Using 3-((1H-imidazol-1-yl)methyl)-1-phenyl-1H-benzo[g]indazol-5-ol as a starting material, the title compound was synthesized according to the procedure described in (3) of Example 1.

Yield: 60%, Yellow solid.

$^1$H NMR (300 MHz, $CDCl_3$) δ: 8.15 (m, 1H), 7.78 (s, 1H), 7.66-7.64 (m, 3H), 7.52-7.50 (m, 2H), 7.44 (m, 1H), 7.34 (m, 1H), 7.22 (m, 1H), 7.02 (m, 1H), 6.84 (m, 1H), 5.44 (s, 2H).

Example 23: Synthesis of Compound 25 (1-(4-fluorophenyl)-3-methyl-1H-benzo[g]indazol-4,5-dione)

(1) Synthesis of 1-(4-fluorophenyl)-3-methyl-1H-benzo[g]indazol-5-ol

Using 1-(4-fluorophenyl)-5-methoxy-3-methyl-1H-benzo[g]indazole as a starting material, the title compound was synthesized according to the procedure described in (2) of Example 1, and obtained product was used for next step without further purification.

(2) Synthesis of Compound 25 (1-(4-fluorophenyl)-3-methyl-1H-benzo[g]indazol-4,5-dione)

Using 1-(4-fluorophenyl)-3-methyl-1H-benzo[g]indazol-5-ol as a starting material, the title compound was synthesized according to the procedure described in (3) of Example 1.

Yield: 40%, Yellow solid.

$^1$H NMR (300 MHz, $CDCl_3$) δ: 8.03-7.98 (m, 1H), 7.72-7.68 (m, 2H), 7.55-7.50 (m, 4H), 6.78-6.75 (m, 1H), 2.45 (s, 3H).

Example 24: Synthesis of 26 (1-(4-chlorophenyl)-3-methyl-1H-benzo[g]indazol-4,5-dione)

(1) Synthesis of 1-(4-chlorophenyl)-3-methyl-1H-benzo[g]indazol-5-ol

Using 1-(4-chlorophenyl)-5-methoxy-3-methyl-1H-benzo[g]indazole as a starting material, the title compound was synthesized according to the procedure described in (2) of Example 1, and obtained product was used for next step without further purification.

(2) Synthesis of Compound 26 (1-(4-chlorophenyl)-3-methyl-1H-benzo[g]indazol-4,5-dione)

Using 1-(4-chlorophenyl)-3-methyl-1H-benzo[g]indazol-5-ol as a starting material, the title compound was synthesized according to the procedure described in (3) of Example 1.

Yield: 44%, Yellow solid.

$^1$H NMR (300 MHz, $CDCl_3$) δ: 8.12-8.10 (m, 1H), 7.58-7.53 (m, 2H), 7.48-7.45 (m, 2H), 7.44-7.36 (m, 2H), 6.90 (s, 1H), 2.56 (s, 3H).

Example 25: Synthesis of Compound 27 (1-(3,5-difluorophenyl)-3-methyl-1H-benzo[g]indazol-4,5-dione)

(1) Synthesis of 1-(3,5-difluorophenyl)-3-methyl-1H-benzo[g]indazol-5-ol

Using 1-(3,5-difluorophenyl)-5-methoxy-3-methyl-1H-benzo[g]indazole as a starting material, the title compound was synthesized according to the procedure described in (2) of Example 1, and obtained product was used for next step without further purification.

(2) Synthesis of Compound 27 (1-(3,5-difluorophenyl)-3-methyl-1H-benzo[g]indazol-4,5-dione)

Using 1-(3,5-difluorophenyl)-3-methyl-1H-benzo[g]indazol-5-ol as a starting material, the title compound was synthesized according to the procedure described in (3) of Example 1.

Yield: 12%, Yellow solid.

$^1$H NMR (300 MHz, $CDCl_3$) δ: 8.17-8.15 (m, 1H), 7.51-7.44 (m, 2H), 7.13-7.08 (m, 3H), 6.99-6.97 (m, 1H), 2.59 (s, 3H).

Example 26: Synthesis of Compound 28 (1-(2,4-dichlorophenyl)-3-methyl-1H-benzo[g]indazol-4,5-dione)

(1) Synthesis of 1-(2,4-dichlorophenyl)-3-methyl-1H-benzo[g]indazol-5-ol

Using 1-(2,4-dichlorophenyl)-5-methoxy-3-methyl-1H-benzo[g]indazole as a starting material, the title compound was synthesized according to the procedure described in (2) of Example 1, and obtained product was used for next step without further purification.

(2) Synthesis of Compound 28 (1-(2,4-dichlorophenyl)-3-methyl-1H-benzo[g]indazol-4,5-dione)

Using 1-(2,4-dichlorophenyl)-3-methyl-1H-benzo[g]indazol-5-ol as a starting material, the title compound was synthesized according to the procedure described in (3) of Example 1.

Yield: 32%, Yellow solid.

$^1$H NMR (300 MHz, $CDCl_3$) δ: 8.17-8.15 (m, 1H), 7.69 (s, 1H), 7.60-7.54 (m, 2H), 7.50-7.40 (m, 2H), 6.72-6.70 (m, 1H), 2.61 (s, 3H).

Example 27: Synthesis of Compound 29 (3-methyl-1-p-tolyl-1H-benzo[g]indazol-4,5-dione)

(1) Synthesis of 3-methyl-1-p-tolyl-1H-benzo[g]indazol-5-ol

Using 5-methoxy-3-methyl-1-p-tolyl-1H-benzo[g]indazole as a starting material, the title compound was synthesized according to the procedure described in (2) of Example 1, and obtained product was used for next step without further purification.

(2) Synthesis of Compound 29 (3-methyl-1-p-tolyl-1H-benzo[g]indazol-4,5-dione)

Using 3-methyl-1-p-tolyl-1H-benzo[g]indazol-5-ol as a starting material, the title compound was synthesized according to the procedure described in (3) of Example 1.

Yield: 27%, Yellow solid.

$^1$H NMR (300 MHz, $CDCl_3$) δ: 8.12-8.10 (m, 1H), 7.40-7.32 (m, 6H), 6.90-6.88 (m, 1H), 2.58 (s, 3H), 2.51 (s, 3H).

Example 28: Synthesis of 30 (3-methyl-1-(pyridin-2-yl)-1H-benzo[g]indazol-4,5-dione)

(1) Synthesis of 3-methyl-1-(pyridin-2-yl)-1H-benzo[g]indazol-5-ol

Using 5-methoxy-3-methyl-1-(pyridin-2-yl)-1H-benzo[g]indazole as a starting material, the title compound was synthesized according to the procedure described in (2) of Example 1, and obtained product was used for next step without further purification.

(2) Synthesis of Compound 30 (3-methyl-1-(pyridin-2-yl)-1H-benzo[g]indazol-4,5-dione)

Using 3-methyl-1-(pyridin-2-yl)-1H-benzo[g]indazol-5-ol as a starting material, the title compound was synthesized according to the procedure described in (3) of Example 1.

Yield: 21%, Yellow solid.

$^1$H NMR (300 MHz, $CDCl_3$) δ: 8.69-8.66 (m, 1H), 8.20-8.14 (m, 1H), 8.09-8.06 (m, 1H), 7.78-7.74 (m, 1H), 7.59-7.56 (m, 1H), 7.46-7.42 (m, 2H), 7.08-6.94 (m, 1H), 2.66-2.63 (s, 3H).

Example 29: Synthesis of Compound 31 (3-methyl-1-(pyridin-3-yl)-1H-benzo[g]indazol-4,5-dione)

(1) Synthesis of 3-methyl-1-(pyridin-3-yl)-1H-benzo[g]indazol-5-ol

Using 5-methoxy-3-methyl-1-(pyridin-3-yl)-1H-benzo[g]indazole as a starting material, the title compound was synthesized according to the procedure described in (2) of Example 1, and obtained product was used for next step without further purification.

(2) Synthesis of Compound 31 (3-methyl-1-(pyridin-3-yl)-1H-benzo[g]indazol-4,5-dione)

Using 3-methyl-1-(pyridin-3-yl)-1H-benzo[g]indazol-5-ol as a starting material, the title compound was synthesized according to the procedure described in (3) of Example 1.

Yield: 27%, Yellow solid.

$^1$H NMR (300 MHz, $CDCl_3$) δ: 8.90-8.86 (m, 2H), 8.25-8.21 (m, 1H), 7.97-7.94 (m, 1H), 7.66-7.62 (m, 1H), 7.52-7.49 (m, 1H), 7.43-7.40 (m, 1H), 6.90-6.88 (m, 1H), 2.65 (s, 3H).

Example 30: Synthesis of Compound 32 (1-(2,4-difluorophenyl)-3-methyl-1H-benzo[g]indazol-4,5-dione)

(1) Synthesis of 1-(2,4-difluorophenyl)-3-methyl-1H-benzo[g]indazol-5-ol

Using 1-(2,4-difluorophenyl)-5-methoxy-3-methyl-1H-benzo[g]indazole as a starting material, the title compound was synthesized according to the procedure described in (2) of Example 1, and obtained product was used for next step without further purification.

(2) Synthesis of Compound 32 (1-(2,4-difluorophenyl)-3-methyl-1H-benzo[g]indazol-4,5-dione)

Using 1-(2,4-difluorophenyl)-3-methyl-1H-benzo[g]indazol-5-ol as a starting material, the title compound was synthesized according to the procedure described in (3) of Example 1.

Yield: 27%, Yellow solid.

$^1$H NMR (300 MHz, $CDCl_3$) δ: 8.14-8.12 (m, 1H), 7.67-7.60 (m, 1H), 7.48-7.41 (m, 2H), 7.19-7.12 (m, 2H), 6.85-6.83 (m, 1H), 2.58 (s, 3H).

Example 31: Synthesis of Compound 33 (1-phenyl-1H-benzo[g]indazol-4,5-dione)

(1) Synthesis of 1-phenyl-1H-benzo[g]indazol-5-ol

Using 5-methoxy-1-phenyl-1H-benzo[g]indazole as a starting material, the title compound was synthesized according to the procedure described in (2) of Example 1, and obtained product was used for next step without further purification.

(2) Synthesis of Compound 33 (1-phenyl-1H-benzo[g]indazol-4,5-dione)

Using 1-phenyl-1H-benzo[g]indazol-5-ol as a starting material, the title compound was synthesized according to the procedure described in (3) of Example 1.

Yield: 30%, Yellow solid.

$^1$H NMR (300 MHz, $CDCl_3$) δ: 8.23 (s, 1H), 8.20-8.17 (m, 1H), 7.64-7.63 (m, 3H), 7.54-7.50 (m, 2H), 7.47-7.42 (m, 1H), 7.37-7.32 (m, 1H), 6.90-6.87 (m, 1H).

Example 32: Compound 34 (1-phenyl-3-(trifluoromethyl)-1H-benzo[g]indazol-4,5-dione)

(1) Synthesis of 1-phenyl-3-(trifluoromethyl)-1H-benzo[g]indazol-5-ol

Using 5-methoxy-1-phenyl-3-(trifluoromethyl)-1H-benzo[g]indazole as a starting material, the title compound was synthesized according to the procedure described in (2) of Example 1, and obtained product was used for next step without further purification.

(2) Synthesis of Compound 34 (1-phenyl-3-(trifluoromethyl)-1H-benzo[g]indazol-4,5-dione)

Using 1-phenyl-3-(trifluoromethyl)-1H-benzo[g]indazol-5-ol as a starting material, the title compound was synthesized according to the procedure described in (3) of Example 1.

Yield: 19%, Yellow solid.

$^{1}$H NMR (300 MHz, $CDCl_3$) δ: 8.23-8.20 (m, 1H), 7.68-7.66 (m, 3H), 7.56-7.48 (m, 3H), 7.41-7.36 (m, 1H), 6.89-6.87 (m, 1H).

Example 33: Synthesis of 35 (7-fluoro-3-methyl-1-phenyl-1H-benzo[g]indazol-4,5-dione (1) Synthesis of 7-fluoro-3-methyl-1-phenyl-1H-benzo[g]indazol-5-ol Using 7-fluoro-5-methoxy-3-methyl-1-phenyl-1H-benzo[g]indazole as a starting material, the title compound was synthesized according to the procedure described in (2) of Example 1, and obtained product was used for next step without further purification.

(2) Synthesis of Compound 35 (7-fluoro-3-methyl-1-phenyl-1H-benzo[g]indazol-4,5-dione)

Using 7-fluoro-3-methyl-1-phenyl-1H-benzo[g]indazol-5-ol as a starting material, the title compound was synthesized according to the procedure described in (3) of Example 1.

Yield: 29%, Yellow solid.

$^{1}$H NMR (300 MHz, $CDCl_3$) δ: 7.85-7.82 (m, 1H), 7.63-7.59 (m, 3H), 7.58-7.46 (m, 2H), 7.26-7.25 (m, 1H), 7.09-7.04 (m, 1H), 6.88-6.82 (m, 1H), 2.61 (s, 3H).

Example 34: Synthesis of Compound 36 (1-(3,5-dichlorophenyl)-3-methyl-1H-benzo[g]indazol-4,5-dione)

(1) Synthesis of 1-(4-chlorophenyl)-3-methyl-1H-benzo[g]indazol-5-ol

Using 1-(3,5-dichlorophenyl)-5-methoxy-3-methyl-1H-benzo[g]indazol (Intermediate 20) as a starting material, the title compound was synthesized according to the procedure described in (2) of Example 1, and obtained product was used for next step without further purification.

(2) Synthesis of Compound 36 (1-(3,5-dichlorophenyl)-3-methyl-1H-benzo[g]indazol-4,5-dione Using 1-(3,5-dichlorophenyl)-3-methyl-1H-benzo[g]indazol-5-ol as a starting material, the title compound was synthesized according to the procedure described in (3) of Example 1.

Yield: 59%, Yellow solid.

$^{1}$H NMR (300 MHz, $CDCl_3$) δ: 8.16 (d, 1H), 7.62 (s, 1H), 7.49 (m, 4H), 6.98 (d, 1H), 2.62 (s, 3H).

Example 35: Synthesis of Compound 37 (4-(3-methyl-4,5-dioxo-4,5-dihydro-1H-benzo[g]indazol-1-yl)benzoic acid)

(1) Synthesis of 4-(5-hydroxy-3-methyl-1H-benzo[g]indazol-1-yl)benzoic acid

Using methyl 4-(5-methoxy-3-methyl-1H-benzo[g]indazol-1-yl)benzoate as a starting material, the title compound was synthesized according to the procedure described in (2) of Example 1, and obtained product was used for next step without further purification.

(2) Synthesis of Compound 37 (4-(3-methyl-4,5-dioxo-4,5-dihydro-1H-benzo[g]indazol-1-yl)benzoic acid)

Using 4-(5-hydroxy-3-methyl-1H-benzo[g]indazol-1-yl)benzoic acid as a starting material, the title compound was synthesized according to the procedure described in (3) of Example 1.

Yield: 48%, Yellow solid.

$^{1}$H NMR (300 MHz, $CDCl_3$) δ: 13.40 (s, 1H), 8.19-8.17 (m, 2H), 7.97-7.95 (m, 1H), 7.73-7.72 (m, 2H), 7.49-7.48 (m, 2H), 6.80 (s, 1H), 2.43 (s, 3H).

Example 36: Synthesis of Compound 38 (3-methyl-1-(naphthalen-1-yl)-1H-benzo[g]indazol-4,5-dione)

(1) Synthesis of 3-methyl-1-(naphthalen-1-yl)-1H-benzo[g]indazol-5-ol

Using 5-methoxy-3-methyl-1-(naphthalen-1-yl)-1H-benzo[g]indazole as a starting material, the title compound was synthesized according to the procedure described in (2) of Example 1, and obtained product was used for next step without further purification.

(2) Synthesis of Compound 38 (3-methyl-1-(naphthalen-1-yl)-1H-benzo[g]indazol-4,5-dione)

Using 3-methyl-1-(naphthalen-1-yl)-1H-benzo[g]indazol-5-ol as a starting material, the title compound was synthesized according to the procedure described in (3) of Example 1.

Yield: 43%, Yellow solid.

$^{1}$H NMR (300 MHz, $CDCl_3$) δ: 8.14-8.13 (m, 2H), 8.03-8.01 (m, 1H), 7.68-7.66 (m, 2H), 7.60-7.59 (m, 1H), 7.52-7.50 (m, 1H), 7.41-7.31 (m, 2H), 7.12-7.10 (m, 1H), 6.44 (s, 1H), 2.70 (s, 3H).

Example 37: Synthesis of Compound 39 (1-(5-chloropyridin-3-yl)-3-methyl-1H-benzo[g]indazol-4,5-dione)

(1) Synthesis of 1-(5-chloropyridin-3-yl)-3-methyl-1H-benzo[g]indazol-5-ol

Using 1-(5-chloropyridin-3-yl)-5-methoxy-3-methyl-1H-benzo[g]indazole as a starting material, the title compound was synthesized according to the procedure described in (2) of Example 1, and obtained product was used for next step without further purification.

(2) Synthesis of Compound 39 (3-methyl-1-(naphthalen-1-yl)-1H-benzo[g]indazol-4,5-dione)

Using 3-methyl-1-(naphthalen-1-yl)-1H-benzo[g]indazol-5-ol as a starting material, the title compound was synthesized according to the procedure described in (3) of Example 1.

Yield: 38%, Yellow solid.

$^1$H NMR (300 MHz, $CDCl_3$) δ: 8.93-8.91 (m, 1H), 8.71-8.69 (m, 1H), 8.20-8.15 (m, 2H), 7.50-7.45 (m, 1H), 7.40-7.32 (m, 1H), 6.85 (s, 1H), 2.56 (s, 3H).

Example 38: Synthesis of Compound 40 (3-methyl-1-(thiazol-2-yl)-1H-benzo[g]indazol-4,5-dione)

(1) Synthesis of 2-(5-methoxy-3-methyl-1H-benzo[g]indazol-1-yl)thiazole

5-Methoxy-3-methyl-1H-benzo[g]indazole (1 mmol, Intermediate 8), CuI (5 mol %), N,N'-dimethylethylenediamine (10 mol %) and $K_3PO_4$ (2 mmol) were dissolved in DMF. After temperature was raised up to 110° C., 2-Bromothiazole (1.2 mmol) was added, and resulting mixture was stirred at 110° C. Reaction was quenched by adding $H_2O$, the reaction mixture was extracted with ethyl acetate, and extract was dried over $MgSO_4$ and concentrated under reduced pressure, to obtain the title compound, and obtained product was used for next step without further purification.

(2) Synthesis of 3-methyl-1-(thiazol-2-yl)-1H-benzo[g]indazol-5-ol

Using 2-(5-methoxy-3-methyl-1H-benzo[g]indazol-1-yl) thiazole as a starting material, the title compound was synthesized according to the procedure described in (2) of Example 1, and obtained product was used for next step without further purification.

(3) Synthesis of Compound 40 (3-methyl-1-(thiazol-2-yl)-1H-benzo[g]indazol-4,5-dione)

Using 3-methyl-1-(thiazol-2-yl)-1H-benzo[g]indazol-5-ol as a starting material, the title compound was synthesized according to the procedure described in (3) of Example 1.

Yield: 38%, Yellow solid.

$^1$H NMR (300 MHz, $CDCl_3$) δ: 8.15-8.13 (m, 1H), 8.06-8.04 (m, 1H), 7.76-7.75 (m, 1H), 7.53-7.44 (m, 3H), 2.56 (s, 3H).

Example 39: Synthesis of Compound 41 (3-methyl-1-(pyridin-4-yl)-1H-benzo[g]indazol-4,5-dione) and Compound 42 (3-methyl-2-(pyridin-4-yl)-2H-benzo[g]indazol-4,5-dione)

(1) Synthesis of a mixture of 5-methoxy-3-methyl-1-(pyridin-4-yl)-1H-benzo[g]indazole and 5-methoxy-3-methyl-2-(pyridin-4-yl)-2H-benzo[g]indazole 5-Methoxy-3-methyl-1H-benzo[g]indazole (2 mmol, Intermediate 8), CuI (5 mol %), N,N'-dimethylethylenediamine (10 mol %), $K_3PO_4$ (4 mmol) and 4-iodopyridine (2.4 mmol) were dissolved in DMF. The resulting mixture was stirred at below 80° C. for 8 hours. Reaction was quenched by adding $H_2O$, the reaction mixture was extracted with ethyl acetate, and organic layer was dried over $MgSO_4$ and concentrated under reduced pressure, to obtain a mixture of 5-methoxy-3-methyl-1-(pyridin-4-yl)-1H-benzo[g]indazole and 5-methoxy-3-methyl-2-(pyridin-4-yl)-2H-benzo[g]indazole, and obtained mixture was used for next step without further purification.

(2) Synthesis of a mixture of 3-methyl-1-(pyridin-4-yl)-1H-benzo[g]indazol-5-ol and 3-methyl-2-(pyridin-4-yl)-2H-benzo[g]indazol-5-ol Using the mixture of 5-methoxy-3-methyl-1-(pyridin-4-yl)-1H-benzo[g]indazole and 5-methoxy-3-methyl-2-(pyridin-4-yl)-2H-benzo[g]indazole as a starting material, a mixture of the title compound was synthesized according to the procedure described in (2) of Example 1, and obtained mixture was used for next step without further purification.

(3) Synthesis of Compound 41 (3-methyl-1-(pyridin-4-yl)-1H-benzo[g]indazol-4,5-dione) and Compound 42 (3-methyl-2-(pyridin-4-yl)-2H-benzo[g]indazol-4,5-dione)

Using the mixture of 3-methyl-1-(pyridin-4-yl)-1H-benzo[g]indazol-5-ol and 3-methyl-2-(pyridin-4-yl)-2H-benzo[g]indazol-5-ol as a starting material, a mixture of the title compound was synthesized according to the procedure described in (3) of Example 1, from which Compound 41 and Compound 42 were separated.

(Compound 41) Yield: overall 6%, Yellow solid.

$^1$H NMR (300 MHz, $CDCl_3$) δ: 9.01-9.00 (m, 1H), 8.21-8.20 (m, 1H), 7.66-7.65 (m, 1H), 7.25-7.23 (m, 1H), 7.21-7.17 (m, 4H), 2.38 (s, 3H).

(Compound 42) Yield: overall 4%, Yellow solid.

$^1$H NMR (300 MHz, $CDCl_3$) δ: 8.87-8.85 (m, 1H), 8.19-8.17 (m, 1H), 8.12-8.10 (m, 1H), 7.73-7.69 (m, 1H), 7.60-7.59 (m, 2H), 7.55-7.51 (m, 1H), 2.85 (s, 3H).

Example 40: Synthesis of Compound 43 (3-methyl-1H-benzo[g]indazol-4,5-dione)

(1) Synthesis of 3-methyl-1H-benzo[g]indazol-5-ol

Using 5-methoxy-3-methyl-1H-benzo[g]indazole (Intermediate 8) as a starting material, the title compound was synthesized according to the procedure described in (2) of Example 1, and obtained product was used for next step without further purification.

(2) Synthesis of Compound 43 (3-methyl-1H-benzo[g]indazol-4,5-dione

Using 3-methyl-1H-benzo[g]indazol-5-ol as a starting material, the title compound was synthesized according to the procedure described in (3) of Example 1.

Yield: 80%, Yellow solid.

$^1$H NMR (300 MHz, DMSO-$d_6$) δ: 13.65 (br s, 1H), 7.98-7.95 (m, 2H), 7.76-7.73 (m, 1H), 7.54-7.50 (m, 1H), 2.54 (s, 3H).

Example 41: Synthesis of Compound 44 (3-methyl-2-(phenylsulfonyl)-2H-benzo[g]indazol-4,5-dione)

(1) Synthesis of Compound 44 (3-methyl-2-(phenylsulfonyl)-2H-benzo[g]indazol-4,5-dione)

3-Methyl-1H-benzo[g]indazol-4,5-dione (0.95 mmol, Compound 43) and dimethylaminopyridine (10 mol %) were dissolved in dichloromethane (10 mL). Triethylamine (1.5 mmol) and benzenesulfonyl chloride (1.2 mmol) were added while stirring, and the resulting mixture was stirred at room temperature. When the reaction was completed, the reaction was quenched by adding water, and the reaction mixture was extracted with ethyl acetate. Organic layer was dried over $MgSO_4$ and concentrated under reduced pressure. Obtained product was purified by column chromatography.

Yield: 28%, Yellow solid.

$^1$H NMR (300 MHz, DMSO-$d_6$) δ: 8.17-8.12 (m, 4H), 7.74-7.70 (m, 2H), 7.65-7.61 (m, 2H), 7.57-7.53 (m, 1H), 3.02 (s, 3H).

Example 42: Synthesis of Compound 45 (3-methyl-2-(4-fluorophenylsulfonyl)-2H-benzo[g]indazol-4,5-dione)

(1) Synthesis of Compound 44 (3-methyl-2-(4-fluorophenylsulfonyl)-2H-benzo[g]indazol-4,5-dione)

Using 3-methyl-1H-benzo[g]indazol-4,5-dione (0.95 mmol, Compound 43) and 4-fluorobenzenesulfonyl chloride (1.2 mmol) as a starting material and a reactant, the title compound was synthesized according to the procedure described in (1) of Example 41.

Yield: 35.2%, Yellow solid.

$^1$H NMR (300 MHz, $CDCl_3$) δ: 8.19-8.11 (m, 4H), 7.73-7.69 (m, 1H), 7.56-7.52 (m, 1H), 7.33-7.30 (m, 2H), 3.02 (s, 3H).

Example 43: Synthesis of 46 (2-(2-chlorophenylsulfonyl)-3-methyl-2H-benzo[g]indazol-4,5-dione)

Using 3-methyl-1H-benzo[g]indazol-4,5-dione (0.95 mmol, Compound 43) and 2-chlorobenzenesulfonyl chloride (1.2 mmol) as a starting material and a reactant, the title compound was synthesized according to the procedure described in (1) of Example 41.

Yield: 42.3%, Yellow solid $^1$H NMR (300 MHz, $CDCl_3$) δ: 8.43-8.41 (m, 1H), 8.16-8.14 (m, 1H), 7.95-7.93 (m, 1H), 7.68-7.51 (m, 5H), 3.11 (s, 3H).

Example 44: Synthesis of Compound 47 (2-(3-chlorophenylsulfonyl)-3-methyl-2H-benzo[g]indazol-4,5-dione)

Using 3-methyl-1H-benzo[g]indazol-4,5-dione (0.71 mmol, Compound 43) and 3-chlorobenzenesulfonyl chloride (0.85 mmol) as a starting material and a reactant, the title compound was synthesized according to the procedure described in (1) of Example 41.

Yield: 36.6%, Yellow solid.

$^1$H NMR (300 MHz, $CDCl_3$) δ: 8.17-8.14 (m, 2H), 8.11-8.10 (m, 1H), 8.02-8.00 (m, 1H), 7.75-7.68 (m, 2H), 7.59-7.53 (m, 2H), 3.02 (s, 3H).

Example 45: Synthesis of Compound 48 (3-methyl-2-(pyridin-3-ylsulfonyl)-2H-benzo[g]indazol-4,5-dione)

Using 3-methyl-1H-benzo[g]indazol-4,5-dione (0.71 mmol, Compound 43) and pyridine-3-sulfonyl chloride (0.85 mmol) as a starting material and a reactant, the title compound was synthesized according to the procedure described in (1) of Example 41.

Yield: 28%, Yellow solid.

$^1$H NMR (300 MHz, $CDCl_3$) δ: 8.35-8.34 (m, 1H), 8.95-8.93 (m, 1H), 8.42-8.39 (m, 1H), 8.17-8.11 (m, 2H), 7.74-7.70 (m, 1H), 7.60-7.56 (m, 2H), 3.05 (s, 3H).

Example 46: Synthesis of Compound 49 (2-(4-chlorophenylsulfonyl)-3-methyl-2H-benzo[g]indazol-4,5-dione)

Using 3-methyl-1H-benzo[g]indazol-4,5-dione (0.95 mmol, Compound 43) and 4-chlorobenzenesulfonyl chloride (1.2 mmol) as a starting material and a reactant, the title compound was synthesized according to the procedure described in (1) of Example 41.

Yield: 41%, Yellow solid.

$^1$H NMR (300 MHz, $CDCl_3$) δ: 8.16-8.12 (m, 2H), 8.08-8.05 (m, 2H), 7.73-7.69 (m, 1H), 7.61-7.55 (m, 3H), 3.01 (s, 3H).

Example 47: Synthesis of Compound 50 (3-methyl-2-tosyl-2H-benzo[g]indazol-4,5-dione)

Using 3-methyl-1H-benzo[g]indazol-4,5-dione (0.95 mmol, Compound 43) and 4-toluenesulfonyl chloride (1.2 mmol) as a starting material and a reactant, the title compound was synthesized according to the procedure described in (1) of Example 41.

Yield: 41%, Yellow solid.

$^1$H NMR (300 MHz, $CDCl_3$) δ: 8.15-8.13 (m, 2H), 8.01-7.98 (m, 2H), 7.72-7.68 (m, 1H), 7.55-7.51 (m, 1H), 7.41-7.39 (m, 2H), 3.00 (s, 3H), 2.45 (s, 3H).

Example 48: Synthesis of Compound 51 (2-(4-methoxyphenylsulfonyl)-3-methyl-2H-benzo[g]indazol-4,5-dione)

Using 3-methyl-1H-benzo[g]indazol-4,5-dione (0.71 mmol, Compound 43) and 4-methoxybenzenesulfonyl chloride (0.85 mmol) as a starting material and a reactant, the title compound was synthesized according to the procedure described in (1) of Example 41.

Yield: 64%, Yellow solid.

$^1$H NMR (300 MHz, $CDCl_3$) δ: 8.15-8.13 (m, 2H), 8.06-8.03 (m, 2H), 7.72-7.68 (m, 1H), 7.54-7.50 (m, 1H), 7.07-7.03 (m, 2H), 3.89 (s, 3H), 3.00 (s, 3H).

Example 49: Synthesis of Compound 52 (methyl 4-(3-methyl-4,5-dioxo-4,5-dihydro-2H-benzo[g]indazol-2-ylsulfonyl)benzoate)

Using 3-methyl-1H-benzo[g]indazol-4,5-dione (0.71 mmol, Compound 43) and methyl 4-(chlorosulfonyl)benzoate (0.85 mmol) as a starting material and a reactant, the title compound was synthesized according to the procedure described in (1) of Example 41.

Yield: 44.8%, Yellow solid.

$^1$H NMR (300 MHz, $CDCl_3$) δ: 8.27-8.18 (m, 4H), 8.16-8.12 (m, 2H), 7.73-7.69 (m, 1H), 7.57-7.53 (m, 1H), 3.96 (s, 3H), 3.02 (s, 3H).

Example 50: Synthesis of Compound 53 (2-(cyclopropylsulfonyl)-3-methyl-2H-benzo[g]indazol-4,5-dione)

Using 3-methyl-1H-benzo[g]indazol-4,5-dione (0.71 mmol, Compound 43) and cyclopropylsulfonyl chloride (0.85 mmol) as a starting material and a reactant, the title compound was synthesized according to the procedure described in (1) of Example 41.

Yield: 74%, Yellow solid.

$^1$H NMR (300 MHz, $CDCl_3$) δ: 8.20-8.16 (m, 2H), 7.75-7.71 (m, 1H), 7.59-7.55 (m, 1H), 3.07-3.01 (m, 1H), 2.97 (s, 3H), 1.61-1.58 (m, 2H), 1.32-1.26 (m, 2H).

Example 51: Synthesis of Compound 54 (2-(cyclopentyl)-3-methyl-2H-benzo[g]indazol-4,5-dione)

Using 3-methyl-1H-benzo[g]indazol-4,5-dione (0.71 mmol, Compound 43) and cyclopentylsulfonyl chloride (0.85 mmol) as a starting material and a reactant, the title compound was synthesized according to the procedure described in (1) of Example 41.

Yield: 26.7%, Yellow solid.

$^1$H NMR (300 MHz, $CDCl_3$) δ: 8.20-8.16 (m, 2H), 7.75-7.71 (m, 1H), 7.59-7.55 (m, 1H), 4.27-4.19 (m, 1H), 2.99 (s, 3H), 2.22-2.13 (m, 2H), 2.10-2.01 (m, 2H), 1.94-1.84 (m, 2H), 1.77-1.68 (m, 2H).

Example 52: Synthesis of Compound 55 (4-(3-methyl-4,5-dioxo-4,5-dihydro-2H-benzo[g]indazol-2-ylsulfonyl)benzonitrile)

Using 3-methyl-1H-benzo[g]indazol-4,5-dione (0.71 mmol, Compound 43) and 4-cyanobenzenesulfonyl chloride (0.85 mmol) as a starting material and a reactant, the title compound was synthesized according to the procedure described in (1) of Example 41.

Yield: 22.5%, Yellow solid.

$^1$H NMR (300 MHz, $CDCl_3$) δ: 8.27-8.25 (m, 2H), 8.17-8.15 (m, 1H), 8.12-8.10 (m, 1H), 7.93-7.91 (m, 2H), 7.74-7.71 (m, 1H), 7.59-7.55 (m, 1H), 3.03 (s, 3H).

Example 53: Synthesis of Compound 56 (3-methyl-2-(4-nitrophenylsulfonyl)-2H-benzo[g]indazol-4,5-dione)

Using 3-methyl-1H-benzo[g]indazol-4,5-dione (0.94 mmol, Compound 43) and 4-nitrobenzenesulfonyl chloride (1.13 mmol) as a starting material and a reactant, the title compound was synthesized according to the procedure described in (1) of Example 41.

Yield: 32%, Yellow solid.

$^1$H NMR (300 MHz, $CDCl_3$) δ: 8.47-8.45 (m, 2H), 8.36-8.33 (m, 2H), 8.17-8.15 (m, 1H), 8.12-8.10 (m, 1H), 7.75-7.71 (m, 1H), 7.59-7.55 (m, 1H), 3.05 (s, 3H).

Example 54: Synthesis of Compound 57 (3-methyl-2-(4-(trifluoromethyl)phenylsulfonyl)-2H-benzo[g]indazol-4,5-dione)

Using 3-methyl-1H-benzo[g]indazol-4,5-dione (0.71 mmol, Compound 43) and 4-(trifluoromethyl)benzenesulfonyl chloride (0.85 mmol) as a starting material and a reactant, the title compound was synthesized according to the procedure described in (1) of Example 41.

Yield: 54.8%, Yellow solid.

$^1$H NMR (300 MHz, $CDCl_3$) δ: 8.28-8.26 (m, 2H), 8.17-8.12 (m, 2H), 7.90-7.88 (m, 2H), 7.74-7.70 (m, 1H), 7.58-7.54 (m, 1H), 3.03 (s, 3H).

Example 55: Synthesis of Compound 58 (2-(3,4-difluorophenylsulfonyl)-3-methyl-2H-benzo[g]indazol-4,5-dione)

Using 3-methyl-1H-benzo[g]indazol-4,5-dione (0.5 mmol, Compound 43) and 3,4-difluorobenzenesulfonyl chloride (0.6 mmol) as a starting material and a reactant, the title compound was synthesized according to the procedure described in (1) of Example 41.

Yield: 20.6%, Reddish yellow solid.

$^1$H NMR (300 MHz, $CDCl_3$) δ: 8.19-8.12 (m, 2H), 8.02-7.94 (m, 2H), 7.77-7.71 (m, 1H), 7.60-7.52 (m, 1H), 7.46-7.39 (m, 1H), 3.02 (s, 3H).

Example 56: Synthesis of 59 (2-(2,4-difluorophenylsulfonyl)-3-methyl-2H-benzo[g]indazol-4,5-dione)

Using 3-methyl-1H-benzo[g]indazol-4,5-dione (0.71 mmol, Compound 43) and 2,4-difluorobenzenesulfonyl chloride (0.85 mmol) as a starting material and a reactant, the title compound was synthesized according to the procedure described in (1) of Example 41.

Yield: 14.6%, Yellow solid.

$^1$H NMR (300 MHz, $CDCl_3$) δ: 8.29-8.23 (m, 1H), 8.19-8.15 (m, 1H), 8.07-8.01 (m, 1H), 7.73-7.65 (m, 1H), 7.59-7.52 (m, 1H), 7.19-7.15 (m, 1H), 7.04-6.96 (m, 1H), 3.08 (s, 3H).

Example 57: Synthesis of Compound 60 (3-methyl-2-(quinolin-8-ylsulfonyl)-2H-benzo[g]indazol-4,5-dione)

Using 3-methyl-1H-benzo[g]indazol-4,5-dione (0.71 mmol, Compound 43) and quinoline-8-sulfonyl chloride (0.85 mmol) as a starting material and a reactant, the title compound was synthesized according to the procedure described in (1) of Example 41.

Yield: 30%, Yellow solid.

$^1$H NMR (300 MHz, $CDCl_3$) δ: 8.90-8.89 (m, 1H), 8.82-8.80 (m, 1H), 8.25-8.19 (m, 2H), 8.10-8.08 (m, 1H), 7.93-7.91 (m, 1H), 7.81-7.77 (m, 1H), 7.56-7.50 (m, 2H), 7.46-7.44 (m, 1H), 3.40 (s, 3H).

Example 58: Synthesis of Compound 61 (3-methyl-2-(1-methyl-1H-imidazol-2-ylsulfonyl)-2H-benzo[g]indazol-4,5-dione)

Using 3-methyl-1H-benzo[g]indazol-4,5-dione (0.71 mmol, Compound 43) and 1-methylimidazole-2-sulfonyl chloride (0.85 mmol) as a starting material and a reactant, the title compound was synthesized according to the procedure described in (1) of Example 41.

Yield: 16%, Yellow solid.

$^1$H NMR (300 MHz, $CDCl_3$) δ: 8.18-8.16 (m, 1H), 8.09-8.03 (m, 1H), 7.73-7.69 (m, 1H), 7.58-7.52 (m, 1H), 7.23 (s, 1H), 7.14 (s, 1H), 4.22 (s, 3H), 3.10 (s, 3H).

Example 59: Synthesis of Compound 62 (3-methyl-2-(morpholinosulfonyl)-2H-benzo[g]indazol-4,5-dione)

Using 3-methyl-1H-benzo[g]indazol-4,5-dione (0.71 mmol, Compound 43) and morpholine-4-sulfonyl chloride (0.85 mmol) as a starting material and a reactant, the title compound was synthesized according to the procedure described in (1) of Example 41.

Yield: 23.5%, Yellow solid.

$^1$H NMR (300 MHz, $CDCl_3$) δ: 8.20-8.18 (m, 1H), 8.10-8.08 (m, 1H), 7.75-7.72 (m, 1H), 7.58-7.55 (m, 1H), 3.86-3.84 (m, 4H), 3.62-3.60 (m, 4H), 2.93 (s, 3H).

Example 60: Synthesis of Compound 63 (1-benzyl-3-methyl-1H-benzo[g]indazol-4,5-dione)

(1) Synthesis of 1-benzyl-5-methoxy-3-methyl-1H-benzo[g]indazole

Using 5-methoxy-3-methyl-1H-benzo[g]indazole (2.1 mmol, Intermediate 8) and benzyl bromide (4.2 mmol) as a starting material and a reactant, the title compound was synthesized according to the procedure described in (1) of Example 20.

Yield: 45%, Gray solid.

$^1$H NMR (300 MHz, $CDCl_3$) δ: 8.38-8.36 (m, 1H), 8.26-8.24 (m, 1H), 7.54-7.43 (m, 2H), 7.29-7.21 (m, 3H), 7.11-7.09 (m, 2H), 6.88 (s, 1H), 5.98 (s, 2H), 4.05 (s, 3H), 2.64 (s, 3H).

(2) Synthesis of 1-benzyl-3-methyl-1H-benzo[g]indazol-5-ol

Using 1-benzyl-5-methoxy-3-methyl-1H-benzo[g]indazole as a starting material, the title compound was synthesized according to the procedure described in (2) of Example 1, and obtained product was used for next step without further purification.

(3) Synthesis of Compound 63 (1-benzyl-3-methyl-1H-benzo[g]indazol-4,5-dione)

Using 1-benzyl-3-methyl-1H-benzo[g]indazol-5-ol as a starting material, the title compound was synthesized according to the procedure described in (3) of Example 1.

Yield: 59%, Yellow solid.

$^1$H NMR (300 MHz, $CDCl_3$) δ: 8.14-8.12 (m, 1H), 7.52-7.50 (m, 2H), 7.45-7.30 (m, 4H), 7.15-7.13 (m, 2H), 5.73 (s, 2H), 2.57 (s, 3H).

Example 61: Synthesis of 64 (3-methyl-1-phenethyl-1H-benzo[g]inidazol-4,5-dione)

(1) Synthesis of 5-methoxy-3-methyl-1-phenethyl-1H-benzo[g]indazole

Using 5-methoxy-3-methyl-1H-benzo[g]indazole (2 mmol, Intermediate 8) and phenethyl bromide (4 mmol) as a starting material and a reactant, the title compound was synthesized according to the procedure described in (1) of Example 20, and obtained product was used for next step without further purification.

(2) Synthesis of 3-methyl-1-phenethyl-1H-benzo[g]indazol-5-ol

Using 5-methoxy-3-methyl-1-phenethyl-1H-benzo[g]indazole as a starting material, the title compound was synthesized according to the procedure described in (2) of Example 1, and obtained product was used for next step without further purification.

(3) Synthesis of Compound 64 (3-methyl-1-phenethyl-1H-benzo[g]indazol-4,5-dione)

Using 3-methyl-1-phenethyl-1H-benzo[g]indazol-5-ol as a starting material, the title compound was synthesized according to the procedure described in (3) of Example 1.

Yield: 20%, Yellow solid.

$^1$H NMR (300 MHz, $CDCl_3$) δ: 8.21-8.19 (m, 1H), 7.66-7.61 (m, 2H), 7.52-7.48 (m, 1H), 7.34-7.30 (m, 2H), 7.25-7.21 (m, 3H), 4.72-4.68 (m, 2H), 3.30-3.27 (m, 2H), 2.55 (s, 3H).

Example 62: Synthesis of Compound 65 (1-(4-fluorophenethyl)-3-methyl-1H-benzo[g]indazol-4,5-dione) and Compound 66 (2-(4-fluorophenethyl)-3-methyl-2H-benzo[g]indazol-4,5-dione)

(1) Synthesis of a mixture of 1-(4-fluorophenethyl)-5-methoxy-3-methyl-1H-benzo[g]indazole and 2-(4-fluorophenethyl)-5-methoxy-3-methyl-2H-benzo[g]indazole Using 5-methoxy-3-methyl-1H-benzo[g]indazole (2 mmol, Intermediate 8) and 4-fluorophenethyl bromide (4 mmol) as a starting material and a reactant, a mixture of 1-(4-fluorophenethyl)-5-methoxy-3-methyl-1H-benzo[g]indazole and 2-(4-fluorophenethyl)-5-methoxy-3-methyl-2H-benzo[g]indazole was synthesized according to the procedure described in (1) of Example 20, and obtained mixture was used in the next step without further purification.

(2) Synthesis of a mixture of 1-(4-fluorophenethyl)-3-methyl-1H-benzo[g]indazol-5-ol and 2-(4-fluorophenethyl)-3-methyl-2H-benzo[g]indazol-5-ol Using the mixture of 1-(4-fluorophenethyl)-5-methoxy-3-methyl-1H-benzo[g]indazole and 2-(4-fluorophenethyl)-5-methoxy-3-methyl-2H-benzo[g]indazole as a starting material, a mixture of the title compounds was synthesized according to the procedure described in (2) of Example 1, and obtained mixture was used for next step without further purification.

(3) Synthesis of Compound 65 (1-(4-fluorophenethyl)-3-methyl-1H-benzo[g]indazol-4,5-dione) and Compound 66 (2-(4-fluorophenethyl)-3-methyl-2H-benzo[g]indazol-4,5-dione)

Using the mixture of 1-(4-fluorophenethyl)-3-methyl-1H-benzo[g]indazol-5-ol and 2-(4-fluorophenethyl)-3-methyl-2H-benzo[g]indazol-5-ol as a starting material, a mixture of the title compound was synthesized according to the procedure described in (3) of Example 1, from which Compound 65 and compound 66 were separated.

(Compound 65) Yield: 3%, Yellow solid.

$^1$H NMR (300 MHz, $CDCl_3$) δ: 8.23-8.21 (m, 1H), 7.67-7.59 (m, 2H), 7.54-7.50 (m, 1H), 7.18-7.15 (m, 2H), 7.02-6.98 (m, 2H), 4.70-4.66 (m, 2H), 3.8-3.25 (m, 2H), 2.55 (s, 3H).

(Compound 66) Yield: 2%, Yellow solid.

$^1$H NMR (300 MHz, $CDCl_3$) δ: 8.15-8.13 (m, 1H), 8.06-8.04 (m, 1H), 7.70-7.66 (m, 1H), 7.49-7.45 (m, 1H), 7.04-6.94 (m, 4H), 4.30-4.27 (m, 2H), 3.22-3.19 (m, 2H), 2.22 (s, 3H).

Example 63: Synthesis of Compound 67 (3-methyl-1-(3-phenylpropyl)-1H-benzo[g]indazol-4,5-dione)

(1) Synthesis of 5-methoxy-3-methyl-1-(3-phenylpropyl)-1H-benzo[g]indazole

Using 5-methoxy-3-methyl-1H-benzo[g]indazole (2 mmol, Intermediate 8) and 1-bromo-3-phenylpropane (4 mmol) as a starting material and a reactant, the title compound was synthesized according to the procedure described in (1) of Example 20, and obtained product was used for next step without further purification.

(2) Synthesis of 3-methyl-1-(3-phenylpropyl)-1H-benzo[g]indazol-5-ol

Using 5-methoxy-3-methyl-1-(3-phenylpropyl)-1H-benzo[g]indazole as a starting material, the title compound was synthesized according to the procedure described in (2) of Example 1, and obtained product was used for next step without further purification.

(3) Synthesis of Compound 67 (3-methyl-1-(3-phenylpropyl)-1H-benzo[g]indazol-4,5-dione)

Using 3-methyl-1-(3-phenylpropyl)-1H-benzo[g]indazol-5-ol as a starting material, the title compound was synthesized according to the procedure described in (3) of Example 1.

Yield: 32%, Yellow solid.

$^1$H NMR (300 MHz, $CDCl_3$) δ: 8.13-8.11 (m, 1H), 7.45-7.43 (m, 2H), 7.36-7.33 (m, 2H), 7.29-7.20 (m, 4H), 4.46-4.40 (m, 2H), 2.84-2.80 (m, 2H), 2.50 (s, 3H), 2.31-2.27 (m, 2H).

Example 64: Synthesis of Compound 68 (3-methyl-1-(4-methylphenethyl)-1H-benzo[g]indazol-4,5-dione) and Compound 69 (3-methyl-2-(4-methylphenethyl)-2H-benzo[g]indazol-4,5-dione)

(1) Synthesis of a mixture of 5-methoxy-3-methyl-1-(4-methylphenethyl)-1H-benzo[g]indazole and 5-methoxy-3-methyl-2-(4-methylphenethyl)-2H-benzo[g]indazole Using 5-methoxy-3-methyl-1H-benzo[g]indazole (2 mmol, Intermediate 8) and 4-methylphenethyl bromide (4 mmol) as a starting material and a reactant, a mixture of 5-methoxy-3-methyl-1-(4-methylphenethyl)-1H-benzo[g]indazole and 5-methoxy-3-methyl-2-(4-methylphenethyl)-2H-benzo[g]indazole was synthesized according to the procedure described in (1) of Example 20, and obtained mixture was used in the next reaction without further purification.

(2) Synthesis of a mixture of 3-methyl-1-(4-methylphenethyl)-1H-benzo[g]indazol-5-ol and 3-methyl-2-(4-methylphenethyl)-2H-benzo[g]indazol-5-ol Using the mixture of 5-methoxy-3-methyl-1-(4-methylphenethyl)-1H-benzo[g]indazole and 5-methoxy-3-methyl-2-(4-methylphenethyl)-2H-benzo[g]indazole as a starting material, a mixture of the title compounds was synthesized according to the procedure described in (2) of Example 1, and obtained mixture was used for next step without further purification.

(3) Synthesis of Compound 68 (3-methyl-1-(4-methylphenethyl)-1H-benzo[g]indazol-4,5-dione) and compound 69 (3-methyl-2-(4-methylphenethyl)-2H-benzo[g]indazol-4,5-dione)

Using the mixture of 3-methyl-1-(4-methylphenethyl)-1H-benzo[g]indazol-5-ol and 3-methyl-2-(4-methylphenethyl)-2H-benzo[g]indazol-5-ol as a starting material, a mixture of the title compounds was synthesized according to the procedure described in (3) of Example 1, from which Compound 68 and Compound 69 were separated.

(Compound 68) Yield: 10%, Yellow solid $^1$H NMR (300 MHz, $CDCl_3$) δ: 8.21-8.19 (m, 1H), 7.63 (s, 2H), 7.52-7.50 (m, 1H), 7.11 (s, 4H), 4.69-4.65 (m, 2H), 3.26-3.22 (m, 2H), 2.56 (s, 2H), 2.31 (s, 3H).

(Compound 69) Yield: 9%, Yellow solid.

$^1$H NMR (300 MHz, $CDCl_3$) δ: 8.16-8.13 (m, 1H), 8.07-8.05 (m, 1H), 7.69-7.67 (m, 1H), 7.46-7.44 (m, 1H), 7.08-7.05 (m, 2H), 6.95-6.92 (m, 2H), 4.30-4.26 (m, 2H), 3.19-3.15 (m, 2H), 2.31 (s, 3H), 2.16 (s, 3H).

Example 65: Synthesis of Compound 70 (2-(2-fluorophenethyl)-3-methyl-2H-benzo[g]indazol-4,5-dione)

(1) Synthesis of 2-(2-fluorophenethyl)-5-methoxy-3-methyl-2H-benzo[g]indazole

Using 5-methoxy-3-methyl-1H-benzo[g]indazole (2 mmol, Intermediate 8) and 2-fluorophenethyl bromide (4 mmol) as a starting material and a reactant, the title compound was synthesized according to the procedure described in (1) of Example 20, and obtained product was used for next step without further purification.

(2) Synthesis of 2-(2-fluorophenethyl)-3-methyl-2H-benzo[g]indazol-5-ol

Using 2-(2-fluorophenethyl)-5-methoxy-3-methyl-2H-benzo[g]indazole as a starting material, the title compound was synthesized according to the procedure described in (2) of Example 1, and obtained product was used for next step without further purification.

(3) Synthesis of Compound 70 (2-(2-fluorophenethyl)-3-methyl-2H-benzo[g]indazol-4,5-dione)

Using 2-(2-fluorophenethyl)-3-methyl-2H-benzo[g]indazol-5-ol as a starting material, the title compound was synthesized according to the procedure described in (3) of Example 1.

Yield: 3%, Yellow solid.

$^1$H NMR (300 MHz, $CDCl_3$) δ: 8.14-8.12 (m, 1H), 8.05-8.03 (m, 1H), 7.69-7.65 (m, 1H), 7.48-7.44 (m, 1H), 7.25-7.23 (m, 1H), 7.08-6.96 (m, 3H), 4.36-4.33 (m, 2H), 3.28-3.25 (m, 2H), 2.27 (s, 3H).

EXPERIMENTAL EXAMPLES

Experimental Example 1: In Vitro NQO1 Enzyme Activity Assay

In order to evaluate the activity of the synthesized compound in NQO1, the experiments were performed as follows:

The synthesized compound was dissolved in DMSO to make a 10 mM stock solution, which was further diluted with DMSO to 250 μM so as to prepare a working solution. For experimental groups, the working solution of the compound was added to an enzyme reaction solution in which 50 μL of 1.54 mM Cytochrome C solution was added to 900 μL of 50 mM Tris-HCl (pH7.5) containing 0.14% BSA. For negative control groups, DMSO not containing the compound of the invention was added to the enzyme reaction solution as above. For each experimental and control group, 20 μL of 100 ng/mL NQO1 protein was added, and then 10

μL of 20 mM NADH was added to bring up the total volume to 1 mL. The change of absorbance was measured at 550 nm for 10 minutes using 1 mL cuvette. The kinetics of reaction was measured by the increase of absorbance as the cytochrome C was reduced at 550 nm over 10 minutes. The activity of NQO1 was measured by the amount of cytochrome C that is being reduced (nmol cytochrome C that was reduced/min/ug NQO1 protein).

Absorption coefficient of Cytochrome C: 21.1 (μmol/mL)$^{-1}$cm$^{-1}$

BSA: Bovine Serum Albumin

Tris-HCN: Tris(hydroxymethyl)aminomethane hydrochloride (buffer solution)

Equipment=Cary 100 UV-Vis Spectrophotometer

The results are shown in Tables 1 to 8.

TABLE 1

| Compound Nos. | NQO1 activity assay Cytochrome C reduced/min/μg NQO1 protein, NQO1 2 ng, 10 nM Compound |
|---|---|
| Control | 31 |
| 1 | 658 |
| 2 | 455 |
| 3 | 755 |
| 4 | 170 |
| 5 | 816 |
| 6 | 916 |
| 7 | 96 |
| 8 | 112 |
| 9 | 932 |
| 10 | 138 |
| 11 | 203 |
| 12 | 225 |
| 13 | 198 |
| 14 | 156 |
| 15 | 190 |
| 16 | 596 |
| 17 | 254 |
| 18 | 189 |
| 19 | 106 |
| 20 | 918 |
| 21 | 925 |
| 22 | 481 |
| 23 | 477 |
| 24 | 596 |
| 25 | 463 |
| 26 | 465 |
| 27 | 415 |
| 28 | 745 |
| 29 | 668 |
| 30 | 494 |
| 31 | 900 |
| 32 | 839 |
| 33 | 436 |
| 34 | 716 |
| 35 | 694 |

TABLE 2

| Compound Nos. | NQO1 activity assay Cytochrome C reduced/min/μg NQO1 protein, NQO1 2 ng, 50 nM Compound |
|---|---|
| 9 | 2093 |
| 36 | 1873 |
| 37 | 1034 |
| 43 | 1008 |
| 63 | 1567 |
| 64 | 2081 |

TABLE 3

| Compound Nos. | NQO1 activity assay Cytochrome C reduced/min/μg NQO1 protein, NQO1 2 ng, 50 nM Compound |
|---|---|
| 9 | 3089 |
| 40 | 2041 |
| 41 | 1617 |
| 42 | 3212 |
| 44 | 2169 |

TABLE 4

| Compound Nos. | NQO1 activity assay Cytochrome C reduced/min/μg NQO1 protein, NQO1 2 ng, 50 nM Compound |
|---|---|
| 9 | 3864 |
| 38 | 2696 |
| 39 | 3285 |
| 65 | 3714 |
| 66 | 3001 |

TABLE 5

| Compound Nos. | NQO1 activity assay Cytochrome C reduced/min/μg NQO1 protein, NQO1 2 ng, 50 nM Compound |
|---|---|
| 9 | 3091 |
| 45 | 2092 |
| 46 | 1522 |
| 47 | 1277 |
| 48 | 1749 |

TABLE 6

| Compound Nos. | NQO1 activity assay Cytochrome C reduced/min/μg NQO1 protein, NQO1 2 ng, 50 nM Compound |
|---|---|
| 9 | 2885 |
| 49 | 2171 |
| 50 | 1542 |
| 51 | 1288 |

TABLE 7

| Compound Nos. | NQO1 activity assay Cytochrome C reduced/min/μg NQO1 protein, NQO1 2 ng, 50 nM Compound |
|---|---|
| 9 | 2892 |
| 52 | 2179 |
| 53 | 1549 |
| 54 | 1295 |
| 55 | 1892 |
| 56 | 1839 |
| 57 | 1868 |

TABLE 8

| Compound Nos. | NQO1 activity assay Cytochrome C reduced/min/μg NQO1 protein, NQO1 2 ng, 50 nM Compound |
|---|---|
| 9 | 2709 |
| 58 | 1913 |
| 59 | 1923 |

TABLE 8-continued

| Compound Nos. | NQO1 activity assay Cytochrome C reduced/min/μg NQO1 protein, NQO1 2 ng, 50 nM Compound |
|---|---|
| 60 | 2692 |
| 61 | 2289 |
| 62 | 1916 |
| 67 | 1836 |
| 68 | 1865 |
| 69 | 2460 |
| 70 | 1611 |

As shown in Tables 1 to 8, the amount of cytochrome C being reduced was increased when treated with the compound of the invention, compared with the control not treated with the compound. Thereby it was found and confirmed from these results that the compound of the invention was used as a substrate for NQO1 to activate redox reaction of NQO1.

The invention claimed is:

1. A compound represented by Chemical Formula 1, or a pharmaceutically acceptable salt, hydrate, solvate, enantiomer, diastereomer or tautomer thereof:

Chemical Formula 1

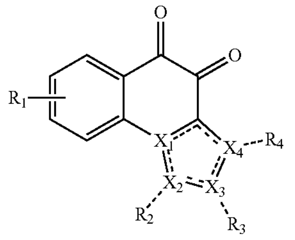

wherein, $R_1$ is H or halo;

$R_2$ is not present, or selected from the group consisting of H, substituted or unsubstituted $C_{1-10}$ alkyl, substituted or unsubstituted $C_{6-10}$ aryl, and substituted or unsubstituted heteroaryl;

$R_3$ is not present, or selected from the group consisting of substituted or unsubstituted $C_{1-10}$ alkyl, unsubstituted heteroaryl, and —S(O)(O)$R_5$;

provided that $R_2$ and $R_3$ cannot simultaneously be not present, alkyl or heteroaryl;

$R_4$ is selected from the group consisting of H, substituted or unsubstituted $C_{1-10}$ alkyl, and substituted or unsubstituted $C_{6-10}$ aryl;

$X_1$ and $X_4$ are carbon atoms, and $X_2$ and $X_3$ are nitrogen atoms;

═ ═ is a single or double bond depending on $R_1$, $R_2$, $R_3$, $X_1$, $X_2$, $X_3$ and $X_4$; and ▪ ▪ ▪ is not present or a single bond depending on $X_1$, $X_2$, $X_3$ and $X_4$, wherein the alkyl is a linear, branched or cyclic hydrocarbon and may contain at least one double bond or triple bond in the hydrocarbyl chain, wherein when the alkyl is substituted, its substituent is selected from the group consisting of halo, $C_{1-6}$ alkyloxy, substituted or unsubstituted $C_{6-10}$ aryl, substituted or unsubstituted heteroaryl, and —N$R_6R_7$, when the aryl or heteroaryl is substituted, its substituent is independently selected from the group consisting of $C_{1-6}$ alkyl, $C_{1-6}$ alkyloxy, halo, cyano, nitro, —C(O)O$R_5$, and $C_{1-6}$ alkyl substituted with 1, 2 or 3 halos, $R_5$ is selected from the group consisting of H, $C_{1-6}$ alkyl, unsubstituted $C_{3-6}$ cycloalkyl, unsubstituted $C_{2-5}$ heterocyclyl, substituted or unsubstituted aryl, and substituted or unsubstituted heteroaryl, wherein when the aryl or heteroaryl is substituted, its substituent is selected from the group consisting of $C_{1-6}$ alkyl, $C_{1-6}$ alkyloxy, halo, cyano, nitro, carboxyl, and $C_{1-6}$ alkyl substituted with 1, 2 or 3 halos, $R_6$ and $R_7$ are each independently H or $C_{1-6}$ alkyl, and in $R_2$ to $R_5$, the aryl is $C_{6-10}$ aromatic ring, the heterocyclyl is a 3- to 7-membered hetero cyclic group containing at least one hetero atom selected from N, O and S in ring structure, and the heteroaryl is a 5- to 10-membered hetero aromatic ring containing at least one hetero atom selected from N, O and S in ring structure.

2. The compound as claimed in claim 1, or a pharmaceutically acceptable salt, hydrate, solvate, enantiomer, diastereomer or tautomer thereof, wherein $R_2$ is not present, or selected from the group consisting of H, unsubstituted $C_{1-10}$ alkyl, substituted or unsubstituted $C_{6-10}$ aryl, and substituted or unsubstituted heteroaryl, wherein when the aryl or heteroaryl is substituted, its substituent is independently selected from the group consisting of $C_{1-6}$ alkyl, and —C(O)O$R_5$;

$R_3$ is not present, or unsubstituted $C_{1-10}$ alkyl or unsubstituted heteroaryl;

provided that $R_2$ and $R_3$ cannot simultaneously be not present, alkyl or $_2$heteroaryl;

$R_4$ is selected from the group consisting of H, substituted or unsubstituted $C_{1-10}$ alkyl, and substituted or unsubstituted $C_{6-10}$ aryl, wherein when the alkyl is substituted, its substituent is selected from the group consisting of halo, $C_{1-6}$ alkyloxy, unsubstituted $C_{6-10}$ aryl, unsubstituted heteroaryl, and —N$R_6R_7$, and when the aryl is substituted, its substituent is halo; and $R_5$, $R_6$ and $R_7$ are each independently H or $C_{1-6}$ alkyl.

3. The compound as claimed in claim 2, or a pharmaceutically acceptable salt, hydrate, solvate, enantiomer, diastereomer or tautomer thereof, wherein the aryl is phenyl or naphthyl, and the heteroaryl is pyridinyl, pyridazinyl, pyrrolyl, pyrazolyl, imadazolyl, oxazolyl, thiazolyl or furanyl.

4. The compound as claimed in claim 3, or a pharmaceutically acceptable salt, hydrate, solvate, enantiomer, diastereomer or tautomer thereof, wherein the compound is selected from the group consisting of the following:

3-methyl-1-phenyl-1H-benzo[g]indazol-4,5-dione;
3-isopropyl-1-phenyl-1H-benzo[g]indazol-4,5-dione;
3-heptyl-1-phenyl-1H-benzo[g]indazol-4,5-dione;
3-phenethyl-1-phenyl-1H-benzo[g]indazol-4,5-dione;
1,3-diphenyl-1H-benzo[g]indazol-4,5-dione;
3-(4-fluorophenyl)-1-phenyl-1H-benzo[g]indazol-4,5-dione;
3-(3,4-difluorophenyl)-1-phenyl-1H-benzo[g]indazol-4,5-dione;
8.1-phenyl-1H-benzo[g]indazol-4,5-dione;
9.methyl)-1-phenyl-1H-benzo[g]indazol-4,5-dione;
10.1-phenyl-1H-benzo[g]indazol-4,5-dione;
7.1-phenyl-1H-benzo[g]indazol-4,5-dione;
1-isopropyl-3-methyl-1H-benzo[g]indazol-4,5-dione;
2-isopropyl-3-methyl-2H-benzo[g]indazol-4,5-dione;
1,3-dimethyl-1H-benzo[g]indazol-4,5-dione;
2,3-dimethyl-2H-benzo[g]indazol-4,5-dione;
3-((1H-imidazol-1-yl)methyl)-1-phenyl-1H-benzo[g]indazol-4,5-dione;

1-(4-fluorophenyl)-3-methyl-1H-benzo[g]indazol-4,5-dione;

1-(4-chlorophenyl)-3-methyl-1H-benzo[g]indazol-4,5-dione;

1-(3,5-difluorophenyl)-3-methyl-1H-benzo[g]indazol-4,5-dione;

1-(2,4-dichlorophenyl)-3-methyl-1H-benzo[g]indazol-4,5-dione;

3-methyl-1-p-tolyl-1H-benzo[g]indazol-4,5-dione;

3-methyl-1-(pyridin-2-yl)-1H-benzo[g]indazol-4,5-dione;

3-methyl-1-(pyridin-3-yl)-1H-benzo[g]indazol-4,5-dione;

1-(2,4-difluorophenyl)-3-methyl-1H-benzo[g]indazol-4,5-dione;

1-phenyl-1H-benzo[g]indazol-4,5-dione;

1-phenyl-3-(trifluoromethyl)-1H-benzo[g]indazol-4,5-dione;

7-fluoro-3-methyl-1-phenyl-1H-benzo[g]indazol-4,5-dione;

1-(3,5-dichlorophenyl)-3-methyl-1H-benzo[g]indazol-4,5-dione;

4-(3-methyl-4,5-dioxo-4,5-dihydro-1H-benzo[g]indazol-1-yl)benzoic acid;

3-methyl-1-(naphthalen-1-yl)-1H-benzo[g]indazol-4,5-dione;

1-(5-chloropyridin-3-yl)-3-methyl-1H-benzo[g]indazol-4,5-dione;

3-methyl-1-(thiazol-2-yl)-1H-benzo[g]indazol-4,5-dione;

3-methyl-1-(pyridin-4-yl)-1H-benzo[g]indazol-4,5-dione;

3-methyl-2-(pyridin-4-yl)-2H-benzo[g]indazol-4,5-dione; and 3-methyl-1H-benzo[g]indazol-4,5-dione.

5. The compound as claimed in claim 1, or a pharmaceutically acceptable salt, hydrate, solvate, enantiomer, diastereomer or tautomer thereof, wherein $R_2$ and $R_3$ are each independently not present or substituted alkyl, provided that $R_2$ and $R_3$ cannot simultaneously be not present or alkyl, the substituent of the alkyl is unsubstituted $C_{6-10}$ aryl, or $C_{6-10}$ aryl substituted with $C_{1-6}$ alkyl or halo; and $R_4$ is unsubstituted $C_{1-10}$ alkyl.

6. The compound as claimed in claim 5, or a pharmaceutically acceptable salt, hydrate, solvate, enantiomer, diastereomer or tautomer thereof, wherein the aryl is phenyl or naphthyl.

7. The compound as claimed in claim 6, or a pharmaceutically acceptable salt, hydrate, solvate, enantiomer, diastereomer or tautomer thereof, wherein the compound is selected from the group consisting of the following:

1-benzyl-3-methyl-1H-benzo[g]indazol-4,5-dione;

3-methyl-1-phenethyl-1H-benzo[g]indazol-4,5-dione;

1-(4-fluorophenethyl)-3-methyl-1H-benzo[g]indazol-4,5-dione;

2-(4-fluorophenethyl)-3-methyl-2H-benzo[g]indazol-4,5-dione;

3-methyl-1-(3-phenylpropyl)-1H-benzo[g]indazol-4,5-dione;

3-methyl-1-(4-methylphenethyl)-1H-benzo[g]indazol-4,5-dione;

3-methyl-2-(4-methylphenethyl)-2H-benzo[g]indazol-4,5-dione; and 2-(2-fluorophenethyl)-3-methyl-2H-benzo[g]indazol-4,5-dione.

8. The compound as claimed in claim 1, or a pharmaceutically acceptable salt, hydrate, solvate, enantiomer, diastereomer or tautomer thereof, wherein $R_2$ is not present;

$R_3$ is —S(O)(O) $R_5$;

$R_4$ is unsubstituted $C_{1-10}$ alkyl; and $R_5$ is selected from the group consisting of $C_{1-6}$ alkyl, substituted of unsubstituted $C_{3-6}$ cycloalkyl, unsubstituted $C_{2-5}$ heterocyclyl, substituted or unsubstituted aryl, and substituted or unsubstituted heteroaryl, wherein the aryl or heteroaryl is substituted, its substituent is independently selected from the group consisting of $C_{1-6}$ alkyl, $C_{1-6}$ alkyloxy, halo, nitro, cyano, —C(O)$OR_9$, and $C_{1-6}$ alkyl substituted with 1, 2 or 3 halos, wherein $R_9$ is $C_{1-6}$ alkyl.

9. The compound as claimed in claim 8, or a pharmaceutically acceptable salt, hydrate, solvate, enantiomer, diastereomer or tautomer thereof, wherein the aryl is phenyl or naphthyl, the heteroaryl is pyridinyl, pyridazinyl, pyrrolyl, pyrazolyl, imadazolyl, oxazolyl, thiazolyl or furanyl, and the heterocyclyl is aziridinyl, azetidinyl, pyrrolidinyl, piperidinyl, piperazinyl or morpholinyl.

10. The compound as claimed in claim 9, or a pharmaceutically acceptable salt, hydrate, solvate, enantiomer, diastereomer or tautomer thereof, wherein the compound is selected from the group consisting of the following:

3-methyl-2-(phenylsulfonyl)-2H-benzo[g]indazol-4,5-dione;

3-methyl-2-(4-fluorophenylsulfonyl)-2H-benzo[g]indazol-4,5-dione;

2-(2-chlorophenylsulfonyl)-3-methyl-2H-benzo[g]indazol-4,5-dione;

2-(3-chlorophenylsulfonyl)-3-methyl-2H-benzo[g]indazol-4,5-dione;

3-methyl-2-(pyridin-3-ylsulfonyl)-2H-benzo[g]indazol-4,5-dione;

2-(4-chlorophenylsulfonyl)-3-methyl-2H-benzo[g]indazol-4,5-dione;

3-methyl-2-tosyl-2H-benzo[g]indazol-4,5-dione;

2-(4-methoxyphenylsulfonyl)-3-methyl-2H-benzo[g]indazol-4,5-dione;

methyl 4-(3-methyl-4,5-dioxo-4,5-dihydro-2H-benzo[g]indazol-2-ylsulfonyl)benzoate;

20.3-methyl-2H-benzo[g]indazol-4,5-dione;

21.3-methyl-2H-benzo[g]indazol-4,5-dione;

4-(3-methyl-4,5-dioxo-4,5-dihydro-2H-benzo[g]indazol-2-ylsulfonyl)benzonitrile;

3-methyl-2-(4-nitrophenylsulfonyl)-2H-benzo[g]indazol-4,5-dione;

3-methyl-2-(4-(trifluoromethyl)phenylsulfonyl)-2H-benzo[g]indazol-4,5-dione;

2-(3,4-difluorophenylsulfonyl)-3-methyl-2H-benzo[g]indazol-4,5-dione;

2-(2,4-difluorophenylsulfonyl)-3-methyl-2H-benzo[g]indazol-4,5-dione;

3-methyl-2-(quinolin-8-ylsulfonyl)-2H-benzo[g]indazol-4,5-dione;

3-methyl-2-(1-methyl-1H-imidazol-2-ylsulfonyl)-2H-benzo[g]indazol-4,5-dione; and 3-methyl-2-(morpholinosulfonyl)-2H-benzo[g]indazol-4,5-dione.

11. A compound represented by Chemical Formula 2, or a salt, enantiomer, diastereomer or tautomer thereof:

Chemical Formula 2

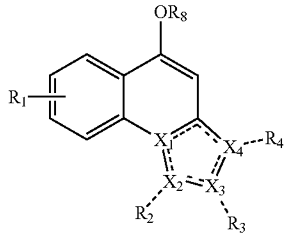

wherein, $R_1$ is H or halo;

$R_2$ is not present, or selected from the group consisting of H, substituted or unsubstituted $C_{1-10}$ alkyl, substituted or unsubstituted $C_{6-10}$ aryl, and substituted or unsubstituted heteroaryl;

$R_3$ is not present, or selected from the group consisting of substituted or unsubstituted $C_{1-10}$ alkyl, unsubstituted heteroaryl, and —S(O)(O)$R_5$;

provided that $R_2$ and $R_3$ cannot simultaneously be not present, alkyl or heteroaryl;

$R_4$ is selected from the group consisting of H, substituted or unsubstituted $C_{1-10}$ alkyl, and substituted or unsubstituted $C_{6-10}$ aryl;

$X_1$ and $X_4$ are carbon atoms, and $X_2$ and $X_3$ are nitrogen atoms;

- - - is a single or double bond depending on $R_1$, $R_2$, $R_3$, $X_1$, $X_2$, $X_3$ and $X_4$;

▪ ▪ ▪ is not present or a single bond depending on $X_1$, $X_2$, $X_3$ and $X_4$;

the alkyl is a linear, branched or cyclic hydrocarbyl and may include at least one double bond or triple bond in hydrocarbyl chain, and when the alkyl is substituted, its substituent is selected from the group consisting of halo, $C_{1-6}$ alkyloxy, substituted or unsubstituted $C_{6-10}$ aryl, unsubstituted heteroaryl, and —$NR_6R_7$;

when the aryl or heteroaryl is substituted, its substituent is independently selected from the group consisting of $C_{1-6}$ alkyl, $C_{1-6}$ alkyloxy, halo, cyano, nitro, —C(O)$OR_5$, and $C_{1-6}$ alkyl substituted with 1, 2 or 3 halos;

$R_5$ is selected from the group consisting of H, $C_{1-6}$ alkyl, unsubstituted $C_{3-6}$ cycloalkyl, or unsubstituted $C_{2-5}$ heterocyclyl, substituted or unsubstituted aryl, and substituted or unsubstituted heteroaryl, wherein when the aryl or heteroaryl is substituted, its substituent is selected from the group consisting of $C_{1-6}$ alkyl, $C_{1-6}$ alkyloxy, halo, cyano, nitro, carboxyl, and $C_{1-6}$ alkyl substituted with 1, 2 or 3 halos;

$R_6$ and $R_7$ are each independently H or $C_{1-6}$ alkyl;

$R_8$ is $C_{1-6}$ alkyl, or $C_{1-6}$ alkyl substituted with $C_{1-6}$ alkyloxy; and in $R_2$ to $R_5$, the aryl is $C_{6-10}$ aromatic ring, the heterocyclyl is a 3- to 7-membered hetero cyclic group containing at least one hetero atom selected from N, O and S in ring structure, and the heteroaryl is a 5- to 10-membered hetero aromatic ring containing at least one hetero atom selected from N, O and S in ring structure.

12. The compound as claimed in claim 11, or a salt, enantiomer, diastereomer or tautomer thereof, wherein the compound is selected from the group consisting of the following:

5-Methoxy-3-methyl-1-phenyl-1H-benzo[g]indazole;

(5-Methoxy-1-phenyl-1H-benzo[g]indazol-3-yl) methanol;

24.5-(methoxymethoxy)-1-phenyl-1H-benzo[g]indazole;

5-Methoxy-3-methyl-1H-benzo[g]indazole;

1-(4-Fluorophenyl)-5-methoxy-3-methyl-1H-benzo[g]indazole;

1-(4-Chlorophenyl)-5-methoxy-3-methyl-1H-benzo[g]indazole;

1-(3,5-Difluorophenyl)-5-methoxy-3-methyl-1H-benzo[g]indazole;

1-(2,4-Dichlorophenyl)-5-methoxy-3-methyl-1H-benzo[g]indazole;

5-Methoxy-3-methyl-1-p-tolyl-1H-benzo[g]indazole;

5-Methoxy-3-methyl-1-(pyridin-2-yl)-1H-benzo[g]indazole;

5-Methoxy-3-methyl-1-(pyridin-3-yl)-1H-benzo[g]indazole;

1-(2,4-Difluorophenyl)-5-methoxy-3-methyl-1H-benzo[g]indazole;

5-Methoxy-1-phenyl-1H-benzo[g]indazole;

5-Methoxy-1-phenyl-3-(trifluoromethyl)-1H-benzo[g]indazole;

7-Fluoro-5-methoxy-3-methyl-1-phenyl-1H-benzo[g]indazole;

1-(3,5-Dichlorophenyl)-5-methoxy-3-methyl-1H-benzo[g]indazole;

Methyl 4-(5-methoxy-3-methyl-1H-benzo[g]indazol-1-yl)benzoate;

5-Methoxy-3-methyl-1-(naphthalen-1-yl)-1H-benzo[g]indazole; and 1-(5-Chloropyridin-3-yl)-5-methoxy-3-methyl-1H-benzo[g]indazole.

* * * * *